US011628144B2

(12) United States Patent
White et al.

(10) Patent No.: US 11,628,144 B2
(45) Date of Patent: Apr. 18, 2023

(54) INIPARIB FORMULATIONS AND USES THEREOF

(71) Applicant: TriAct Therapeutics, Inc., San Francisco, CA (US)

(72) Inventors: Thomas F. White, San Francisco, CA (US); Stephen M. Nava, San Francisco, CA (US)

(73) Assignee: TRIACT THERAPEUTICS, INC., San Francisco, CA (US)

( * ) Notice: Subject to any disclaimer, the term of this patent is extended or adjusted under 35 U.S.C. 154(b) by 0 days.

(21) Appl. No.: 16/652,387

(22) PCT Filed: Sep. 28, 2018

(86) PCT No.: PCT/US2018/053558
§ 371 (c)(1),
(2) Date: Mar. 30, 2020

(87) PCT Pub. No.: WO2019/067991
PCT Pub. Date: Apr. 4, 2019

(65) Prior Publication Data
US 2020/0297644 A1 Sep. 24, 2020

Related U.S. Application Data

(60) Provisional application No. 62/566,122, filed on Sep. 29, 2017.

(51) Int. Cl.
A61K 9/28 (2006.01)
A61K 9/00 (2006.01)
A61K 9/08 (2006.01)
A61K 9/20 (2006.01)
A61K 9/48 (2006.01)
A61K 31/166 (2006.01)
A61K 47/10 (2017.01)
A61K 47/12 (2006.01)
A61K 47/14 (2017.01)
A61K 47/20 (2006.01)
A61K 47/32 (2006.01)
A61K 47/34 (2017.01)
A61K 47/38 (2006.01)
A61K 31/495 (2006.01)

(52) U.S. Cl.
CPC ............ A61K 9/28 (2013.01); A61K 9/0053 (2013.01); A61K 9/08 (2013.01); A61K 9/2018 (2013.01); A61K 9/2027 (2013.01); A61K 9/2036 (2013.01); A61K 9/2054 (2013.01); A61K 9/2059 (2013.01); A61K 9/4858 (2013.01); A61K 9/4866 (2013.01); A61K 31/166 (2013.01); A61K 47/10 (2013.01); A61K 47/12 (2013.01); A61K 47/14 (2013.01); A61K 47/20 (2013.01); A61K 47/32 (2013.01); A61K 47/34 (2013.01); A61K 47/38 (2013.01); A61K 31/495 (2013.01)

(58) Field of Classification Search
CPC .......... A61K 9/28; A61K 9/0053; A61K 9/08; A61K 9/2018; A61K 9/2027; A61K 9/2036; A61K 9/2054; A61K 9/2059; A61K 9/4858; A61K 9/4866; A61K 31/166; A61K 47/10; A61K 47/12; A61K 47/14; A61K 47/20; A61K 47/32; A61K 47/34; A61K 47/38; A61K 31/495
See application file for complete search history.

(56) References Cited

U.S. PATENT DOCUMENTS

| 4,683,202 A | 7/1987 | Mullis |
| 4,739,044 A | 4/1988 | Stabinsky |
| 4,757,141 A | 7/1988 | Fung et al. |
| 4,843,155 A | 6/1989 | Chomczynski |
| 5,262,564 A | 11/1993 | Kun et al. |
| 5,348,853 A | 9/1994 | Wang et al. |
| 5,384,261 A | 1/1995 | Winkler et al. |
| 5,445,934 A | 8/1995 | Fodor et al. |
| 5,464,871 A | 11/1995 | Kun et al. |
| 5,473,074 A | 12/1995 | Kun et al. |
| 5,482,975 A | 1/1996 | Kun et al. |
| 5,484,951 A | 1/1996 | Kun et al. |
| 5,516,941 A | 5/1996 | Kun et al. |
| 5,519,053 A | 5/1996 | Kun et al. |
| 5,567,583 A | 10/1996 | Wang et al. |
| 5,568,583 A | 10/1996 | Akasaka et al. |
| 5,583,155 A | 12/1996 | Kun et al. |
| 5,652,260 A | 7/1997 | Kun et al. |

(Continued)

FOREIGN PATENT DOCUMENTS

| WO | WO-9104663 A1 | 4/1991 |
| WO | WO-9206687 A1 | 4/1992 |

(Continued)

OTHER PUBLICATIONS

A Guidebook To Particle Size Analysis. Ed. Horiba Instruments Inc., 2017, 34 pages. (Year: 2017).*
Webb. Interpretation of Particle Size Reported by Different Analytical Techniques. Ed. Micromeritics Instrument Corp, 2006, 10 pages. (Year: 2006).*
Ayhan et al.: Neoadjuvant Chemotherapy in Gynecological Cancers. Eur J Gynaecol Oncol. 27(1): 11-15 (2006).
Ayhan et al.: Topotecan as a Second-Line Therapy in Patients With Ovarian and Primary Peritoneal Cancer: Initial Response and Long-Term Follow-Up. Eur J Gynaecol Oncol. 27(6): 603-606 (2006).
Berge et al. Pharmaceutical Salts. Journal of Pharmaceutical Sciences 66(1): 1-19 (Jan. 1977).

(Continued)

Primary Examiner — Robert A Wax
Assistant Examiner — Olga V. Tcherkasskaya
(74) Attorney, Agent, or Firm — Wilson Sonsini Goodrich & Rosati

(57) ABSTRACT

Disclosed herein are pharmaceutical compositions, formulations, and dosage forms and their use in the treatment of a cancer. Also disclosed herein are methods of treating a cancer in a subject in need thereof.

20 Claims, 1 Drawing Sheet

(56) References Cited

U.S. PATENT DOCUMENTS

| | | |
|---|---|---|
| 5,652,367 A | 7/1997 | Kun et al. |
| 5,670,518 A | 9/1997 | Kun et al. |
| 5,677,195 A | 10/1997 | Winkler et al. |
| 5,708,153 A | 1/1998 | Dower et al. |
| 5,736,576 A | 4/1998 | Kun et al. |
| 5,744,305 A | 4/1998 | Fodor et al. |
| 5,753,674 A | 5/1998 | Kun et al. |
| 5,770,358 A | 6/1998 | Dower et al. |
| 5,770,722 A | 6/1998 | Lockhart et al. |
| 5,783,599 A | 7/1998 | Kun et al. |
| 5,786,146 A | 7/1998 | Herman et al. |
| 5,789,162 A | 8/1998 | Dower et al. |
| 5,800,992 A | 9/1998 | Fodor et al. |
| 5,854,033 A | 12/1998 | Lizardi |
| 5,869,717 A | 2/1999 | Frame et al. |
| 5,874,219 A | 2/1999 | Rava et al. |
| 5,877,185 A | 3/1999 | Kun et al. |
| 5,908,861 A | 6/1999 | Kun |
| 5,922,775 A | 7/1999 | Kun et al. |
| 5,994,056 A | 11/1999 | Higuchi |
| 6,004,978 A | 12/1999 | Kun et al. |
| 6,017,704 A | 1/2000 | Herman et al. |
| 6,017,958 A | 1/2000 | Kun et al. |
| 6,020,135 A | 2/2000 | Levine et al. |
| 6,033,854 A | 3/2000 | Kurnit et al. |
| 6,033,860 A | 3/2000 | Lockhart et al. |
| 6,040,138 A | 3/2000 | Lockhart et al. |
| 6,040,193 A | 3/2000 | Winkler et al. |
| 6,169,104 B1 | 1/2001 | Tuse et al. |
| 6,171,785 B1 | 1/2001 | Higuchi |
| 6,200,756 B1 | 3/2001 | Herman et al. |
| 6,265,171 B1 | 7/2001 | Herman et al. |
| 6,303,621 B1 | 10/2001 | Kun |
| 6,303,629 B1 | 10/2001 | Kun |
| 6,316,495 B1 | 11/2001 | Kun et al. |
| 6,326,402 B1 | 12/2001 | Kun et al. |
| 6,331,393 B1 | 12/2001 | Laird et al. |
| 6,344,316 B1 | 2/2002 | Lockhart et al. |
| 7,179,484 B2 | 2/2007 | Singh |
| 7,186,512 B2 | 3/2007 | Martienssen et al. |
| 7,405,227 B2 | 7/2008 | Kun et al. |
| 7,459,274 B2 | 12/2008 | Lakey et al. |
| 7,538,252 B2 | 5/2009 | Ossovskaya et al. |
| 7,553,627 B2 | 6/2009 | Laird et al. |
| 7,611,869 B2 | 11/2009 | Fan |
| 7,700,324 B1 | 4/2010 | Issa et al. |
| 7,732,491 B2 | 6/2010 | Sherman et al. |
| 7,901,880 B2 | 3/2011 | Jeddeloh et al. |
| 7,910,296 B2 | 3/2011 | Jeddeloh et al. |
| 7,994,222 B2 | 8/2011 | Ossovskaya et al. |
| 8,143,447 B2 | 3/2012 | Moore et al. |
| 8,377,985 B2 | 2/2013 | Kun et al. |
| 8,507,000 B2 | 8/2013 | Mulye |
| 11,433,075 B2 | 9/2022 | White |
| 2005/0069879 A1 | 3/2005 | Berlin |
| 2006/0088840 A1 | 4/2006 | Giesing et al. |
| 2007/0015814 A1 | 1/2007 | Kun et al. |
| 2007/0036859 A1 | 2/2007 | Perry et al. |
| 2007/0292883 A1 | 12/2007 | Ossovskaya et al. |
| 2008/0076778 A1 | 3/2008 | Ossovskaya et al. |
| 2008/0103104 A1 | 5/2008 | Moore et al. |
| 2008/0176946 A1 | 7/2008 | Ossovskaya et al. |
| 2008/0262062 A1 | 10/2008 | Ossovskaya et al. |
| 2008/0319054 A1 | 12/2008 | Kun et al. |
| 2009/0048344 A1 | 2/2009 | Forenzo et al. |
| 2009/0076122 A1 | 3/2009 | Kun et al. |
| 2009/0123419 A1 | 5/2009 | Sherman et al. |
| 2009/0149397 A1 | 6/2009 | Ossovskaya et al. |
| 2009/0149417 A1 | 6/2009 | Ossovskaya et al. |
| 2009/0155791 A1 | 6/2009 | Wojdacz et al. |
| 2009/0275608 A1 | 11/2009 | Ossovskaya et al. |
| 2009/0291924 A1 | 11/2009 | Ossovskaya et al. |
| 2010/0003192 A1 | 1/2010 | Sherman et al. |
| 2010/0144836 A1 | 6/2010 | Van Engeland et al. |
| 2010/0160442 A1 | 6/2010 | Ossovskaya et al. |
| 2010/0279327 A1 | 11/2010 | Ossovskaya et al. |
| 2012/0004260 A1 | 1/2012 | Ossovskaya et al. |
| 2012/0130144 A1 | 5/2012 | Sherman et al. |
| 2012/0208706 A1 | 8/2012 | Downing et al. |
| 2012/0238601 A1 | 9/2012 | Moore et al. |
| 2012/0269861 A1 | 10/2012 | Sherman et al. |
| 2013/0274281 A1 | 10/2013 | Bradley |
| 2013/0331457 A1 | 12/2013 | Kun et al. |
| 2014/0044788 A1 | 2/2014 | Verma et al. |
| 2016/0032368 A1 | 2/2016 | Vlassenbroeck et al. |
| 2017/0112809 A1 | 4/2017 | Orwar et al. |
| 2020/0113852 A1 | 4/2020 | White |
| 2020/0113909 A1 | 4/2020 | White |

FOREIGN PATENT DOCUMENTS

| | | |
|---|---|---|
| WO | WO-9218123 A2 | 10/1992 |
| WO | WO-9307868 A1 | 4/1993 |
| WO | WO-9409776 A1 | 5/1994 |
| WO | WO-9426730 A2 | 11/1994 |
| WO | WO-9622791 A1 | 8/1996 |
| WO | WO-9746228 A1 | 12/1997 |
| WO | WO-9842328 A1 | 10/1998 |
| WO | WO-9851307 A1 | 11/1998 |
| WO | WO-9851308 A1 | 11/1998 |
| WO | WO-9920263 A1 | 4/1999 |
| WO | WO-0009114 A1 | 2/2000 |
| WO | WO-2005012578 A1 | 2/2005 |
| WO | WO-2006056480 A2 | 6/2006 |
| WO | WO-2006135873 A2 | 12/2006 |
| WO | WO-2007011962 A2 | 1/2007 |
| WO | WO-2008030883 A2 | 3/2008 |
| WO | WO-2008030887 A2 | 3/2008 |
| WO | WO-2008030891 A2 | 3/2008 |
| WO | WO-2008030892 A2 | 3/2008 |
| WO | WO-2008089272 A1 | 7/2008 |
| WO | WO-2008147418 A1 | 12/2008 |
| WO | WO-2008154590 A2 | 12/2008 |
| WO | WO-2009021141 A1 | 2/2009 |
| WO | WO-2009049916 A2 | 4/2009 |
| WO | WO-2009050738 A2 | 4/2009 |
| WO | WO-2009051815 A1 | 4/2009 |
| WO | WO-2009064444 A2 | 5/2009 |
| WO | WO-2009064738 A2 | 5/2009 |
| WO | WO-2009073869 A1 | 6/2009 |
| WO | WO-2009100159 A2 | 8/2009 |
| WO | WO-2018237327 A1 | 12/2018 |
| WO | WO-2018237344 A1 | 12/2018 |
| WO | WO-2019067991 A1 | 4/2019 |

OTHER PUBLICATIONS

Blakeley et al. Phase I study of iniparib concurrent with monthly or continuous temozolomide dosing schedules in patients with newly diagnosed malignant gliomas. J Neurooncol 125(1):123-131 (2015).
Bundgaard. Design and Application of Prodrugs. Textbook of Drug Design and Development. Krosgaard-Larsen and Bundgaard. Chapter 5. pp. 113-191 (1991).
Bundgaard. Design of Prodrugs. Elsevier, 1985.
Bundgaard. Means to Enhance Penetration: Prodrugs as a Means to Improve the Delivery of Peptide Drugs. Advanced Drug Delivery Review 8:1-38 (1992).
Chen et al.: Potential for Selective Modulation of Glutathione in Cancer Chemotherapy. Chem Biol Interact 111-112: 263-275 (1998).
Domingo-Musibay et al. What next for newly diagnosed glioblastoma? Future Oncol. 11(24):3273-3283 (2015).
International Application No. PCT/US2018/039126 International Search Report and Written Opinion dated Nov. 26, 2018.
Khalid, et al. Long Circulating Poly(Ethylene Glycol)-Decorated Lipid Nanocapsules Deliver Docetaxel to Solid Tumors. Pharmaceutical Research. 2006;23(4):752-758.
Lincoln, DT et al.: Thioredoxin and Thioredoxin Reductase Expression in Thyroid Cancer Depends on Tumour Aggressiveness. Anticancer Research. vol. 30, No. 3, 767-776 (2010).
Llombart-Cussac et al.: SOLTI NeoPARP: a phase II randomized study of two schedules of iniparib plus paclitaxel versus paclitaxel

(56) References Cited

OTHER PUBLICATIONS alone as neoadjuvant therapy in patients with triplenegative breast cancer. Breast Cancer Research and Treatment. vol. 154, No. 2, 351-357 (2015).
Mendeleyev et al.: Potential Chemotherapeutic Activity of 4-iodo-3-nitrobenzamide. Metabolic Reduction to the 3-nitroso Derivative and Induction of Cell Death in Tumor Cells in Culture. Biochem Pharmacol 50(5): 705-714 (1995).
Nabors et al. A Safety Run-In and Randomized Phase 2 Study of Cilengitide Combined With Chemoradiation for Newly Diagnosed Glioblastoma (NABTT 0306). Cancer 118(22):5601-5607 (2012).
O'Shaughnessy et al.: Iniparib plus Chemotherapy in Metastatic Triple-Negative Breast Cancer. The New England Journal of Medicine. vol. 365, No. 3, 205-214 (2011).
PCT/US2018/039103 International Search Report and Written Opinion dated Sep. 19, 2018.
PCT/US2018/053558 International Search Report and Written Opinion dated Dec. 4, 2018.
Rice et al.: Induction of endonuclease-mediated apoptosis in tumor cells by C-nitroso-substituted ligands of poly (ADP-ribose) polymerase. Proc. Natl. Acad. Sci. USA 89: 7703-7707 (1992).
Saba et al., A comparative oncology study of iniparib defines Its pharmacokinetic profile and biological activity in a naturally-occurring canine cancer model. PLoS One 11(2):e0149194 (2016).
Widder et al. Section III: Prodrugs Kinetics. Method in Enzymology. 112:309-396 (1985).
Acevedo et al. Analysis of the mechanisms mediating tumor-specific changes in gene expression in human liver tumors. Cancer Res. 68:2641-2651 (2008).
Agrawal, et al. Site-specific functionalization of oligodeoxynucleotides for non-radioactive labelling. Tetrahedron Letters. 1990 31:1543-1546.
Aliferis et al., Glioblastoma multiforme: Pathogenesis and treatment. Pharmacology and Therapeutics 152: 63-82 (2015).
Balic et al. High quality assessment of DNA methylation in archival tissues from colorectal cancer patients using quantitative high-resolution melting analysis. J. Mol. Diagn. 11:102-108 (2009).
Bangham et al. Diffusion of univalent ions across the lamellae of swollen phospholipids. J. Mol. Biol. 1965;13:238-252.
Barany. Genetic disease detection and DNA amplification using cloned thermostable ligase. PNAS USA 88:189-193 (1991).
Candiloro et al. Assessing combined methylation-sensitive high resolution melting and pyrosequencing for the analysis of heterogeneous DNA methylation. Epigenetics 6(4):500-507 (2011).
Caruthers. Gene synthesis machines: DNA chemistry and its uses. Science 230(4723):281-285 (1985).
Chinot et al. A Bevacizumab plus Radiotherapy-Temozolomide for Newly Diagnosed Glioblastoma. The New England Journal of Medicine 370 (8): 709-722 (2014).
Costello et al., Restriction Landmark Genome Scanning. Methods in Molecular Biology 200: 53-70 (2002).
Cottrell et al. A real-time PCR assay for DNA-methylation using methylation-specific blockers. Nucleic Acids Res. 32:e10 (2004).
Cottrell et al. Discovery and validation of 3 novel DNA methylation markers of prostate cancer prognosis. J. Urology 177:1753-1758 (2007).
Deng et al., Targeted bisulfite sequencing reveals changes in DNA methylation associated with nuclear reprogramming. Nat Biotechnol. (4):353-360 (2009).
Drmanac et al., Sequencing by hybridization: towards an automated sequencing of one million M13 clones arrayed on membranes, Elctrophoresis 13:566-573 (1992).
Eads, et al. Methylight: a high-throughput assay to measure DNA methylation. Nucleic Acids Research, 2000, pp. e32 (i-viii), vol. 28.
EP Application No. 18820978 Search Report dated Apr. 21, 2021.
EP Application No. 18860672.7 Extended European Search report dated May 27, 2021.
European Application No. 18820013 Search Report dated Apr. 30, 2021.

Fackler et al., Quantitative Multiplex Methylation-Specific PCR Analysis Doubles Detection of Tumor Cells in Breast Ductal Fluid. Clinical Cancer Research 12(11 Pt 1) 3306-3310(2006).
"Fackler, et al. Quantitative multiplex methylation-specific PCR assay for the detection of promoter hypermethylation in multiple genes in breast cancer. Cancer Res. Jul. 1, 2004; 64(13): 4442-4452. doi: 10.1158/0008-5472.CAN-03-3341".
Frommer et al. A genomic sequencing protocol that yields a positive display of 5-methylcytosine residues in individual DNA strands. PNAS USA 89:1827-1831 (1992).
Furnari et al., Malignant astrocytic glioma: genetics, biology, and paths to treatment. Genes Dev 21(21):2683-2710 (2007).
Gebhard et al., Genome-Wide Profiling of CpG Methylation Identifies Novel Targets of Aberrant Hypermethylation in Myeloid Leukemia. < span style="font-size: 12px;" > Cancer Res. 66:6118-6128(2006).
Gebhard et al., Rapid and sensitive detection of CpG-methylation using methyl-binding (MB)-PCR. Nucleic Acids Res. 34(11):e82 (2006).
GenBank: CAG38738.1 IDH1 [*Homo sapiens*] (2008).
Gilbert et al., A Randomized Trial of Bevacizumab for Newly Diagnosed Glioblastoma. The New England Journal of Medicine 370 (8): 699-708 (2014).
Giusti et al. Synthesis and characterization of 5'-fluorescent-dye-labeled oligonucleotides. PCR Methods Appl. 2(3):223-227 (1993).
Gonzalgo et al., Rapid quantitation of methylation differences at specific sites using methylation-sensitive single nucleotide primer extension (Ms-SNuPE). Nucleic Acids Res. 25(12):2529-2531 (1997).
Guatelli et al. Isothermal, in vitro amplification of nucleic acids by a multienzyme reaction modeled after retroviral replication. PNAS USA 87(5):1874-1878 (1990).
Gupta et al. A general method for the synthesis of 3'-sulfhydryl and phosphate group containing oligonucleotides. Nucleic Acids Res. 19(11):3019-3025 (1191).
Hegi et al., Correlation of 06-methylguanine methyltransferase (MGMT) promoter methylation with clinical outcomes in glioblastoma and clinical strategies to modulate MGMT activity. Journal of Clinical Oncology 26(25): 4189-4199 (2008).
Hegi et al., MGMT Gene Silencing and Benefit from Temozolomide in Glioblastoma. The New England Journal of Medicine 352(10): 997-1003 (2005).
Heid et al. Real time quantitative PCR. Genome Res. 6(10):986-994 (1996).
Herman, J.G., et al., "Methylation-Specific PCR: A Novel PCR Assay for Methylation Status of CpG Islands." Proceedings of the National Academy of Science USA 93:9821-9826, Sep. 1996.
Horak et al. ChIP-chip: a genomic approach for identifying transcription factor binding sites. Methods Enzymol 350:469-483 (2002).
Johnston, S.A., Biolistic transformation: microbes to mice, Nature, 346: 776-777 (1990).
Kambara et al. Optimization of Parameters in a DNA Sequenator Using Fluorescence Detection. Nat Biotech 6:816-821 (1988).
Khosla et al., Concurrent therapy to enhance radiotherapeutic outcomes in glioblastoma. Ann Transl Med 4(3):54 (2016).
Koga et al. Genome-wide screen of promoter methylation identifies novel markers in melanoma. Genome Res. 19:1462-1470 (2009).
Kwoh et al. Transcription-based amplification system and detection of amplified human immunodeficiency virus type 1 with a bead-based sandwich hybridization format. PNAS USA 86:1173-1177 (1989).
Lieb, Genome-wide mapping of protein-DNA interactions by chromatin immunoprecipitation and DNA microarray hybridization. Methods Mol Biol 224:99-109 (2003).
Lizardi et al., "Exponential amplification of recombinant-RNA hybridization probes," Biotechnology 6:1197-1202 (1988).
Ma, H. et al. Application of Real-time Polymerase Chain Reaction (RT-PCR), The Journal of American Science, 2 (3):1-15 (Aug. 10, 2006).
Malvern Instruments Limited: A basic guide to particle characterization. White Paper, pp. 1-26 (2015) www.cif.iastate.edu/sites/default/files/uploads/Other_Inst/Particle%20Size/Particle%20Characterization%20Guide.pdf.

(56) References Cited

OTHER PUBLICATIONS

McClelland et al., Effect of site-specific modification on restriction endonucleases and DNA modification methyltransferases.. Nucleic Acids Res. 22(17): 3640-3659 (1994).
National Cancer Institute Clinical Trials and Translational Research Advisory Committee (CTAC) Glioblastoma (GBM) Working Group. Working Group Report Jul. 17, 2019. 27 pages.
Nelson et al. Bifunctional oligonucleotide probes synthesized using a novel CPG support are able to detect single base pair mutations. Nucleic Acids Res. 17(18):7187-7194 (1989).
O'Geen et al. Comparison of sample preparation methods for ChIP-chip assays. BioTechniques 41(5):577-580 (2006).
Olek et al., The pre-implantation ontogeny of the H19 methylation imprint. Nature Genetics 17(3):275-276 (1997).
Ostrom et al., CBTRUS Statistical Report: Primary Brain and Other Central Nervous System Tumors Diagnosed in the United States 2013-2017. Neuro-Oncology 22(S1): 1-96 (2020).
Pelizzola et al. MEDME: an experimental and analytical methodology for the estimation of DNA methylation levels based on microarray derived MeDIP-enrichment. Genome Res. 18:1652-1659 (2008).
Ploem. Chapter 1: Fluorescence Microscopy. Fluorescent and Luminescent Probes for Biological Activity Mason, T. G. Ed., Academic Press, Landon, pp. 1-11 (1993).
Rauch et al., High-resolution mapping of DNA hypermethylation and hypomethylation in lung cancer. Proc Natl Acad Sci USA. 105(1):252-257 (2008).
Rein et al., Identifying 5-methylcytosine and related modifications in DNA genomes. Nucleic Acids Res. 26(10):2255-2264 (1998).
Sadri et al. Rapid analysis of DNA methylation using new restriction enzyme sites created by bisulfite modification. Nucleic Acids Res. 24:5058-5059 (1996).
Shiraishi et al., Isolation of DNA fragments associated with methylated CpG islands in human adenocarcinomas of the lung using a methylated DNA binding column and denaturing gradient gel electrophoresis. PNAS 96(6):2913-2918 (1999).
Smith et al. Fluorescence detection in automated DNA sequence analysis, Nature 321:674-679 (1986).
Smith et al. The synthesis of oligonucleotides containing an aliphatic amino group at the 5' terminus: synthesis of fluorescent DNA primers for use in DNA sequence analysis. Nucl. Acid Res. 13:2399-2412 ( 1985).
Smrdel et al., Long-term survival in glioblastoma: methyl guanine methyl transferase (MGMT) promoter methylation as independent favourable prognostic factor. Radiology and Oncology 50(4): 394-401 (2016).
Sproat, et al. The synthesis of protected 5'-mercapto-2',5'-dideoxyribonucleoside-3'-O-phosphoramidites; uses of 5'-mercapto-oligodeoxyribonucleotides. Nucleic Acids Res. Jun. 25, 1987;15(12):4837-48.
Stupp et al., Cilengitide combined with standard treatment for patients with newly diagnosed glioblastoma with methylated MGMT promoter (Centric EORTC 26071-22072 study): a multicentre, randomised, open-label, phase 3 trial. University of Zurich (2014). 45 pages.
Sulman et al., Radiation Therapy for Glioblastoma: American Society of Clinical Oncology Clinical Practice Guideline Endorsement of the American Society for Radiation Oncology Guideline. Journal of Clinical Oncology 35(3): 361-369 (2016).
Szoka et al. Procedure for preparation of liposomes with large internal aqueous space and high capture by reverse-phase evaporation. PNAS. 1978;75:4194-4198.
Toyota, et al. Identification of differentially methylated sequences in colorectal cancer by methylated CpG island amplification. Cancer Research. May 1999. 50(10).
U.S. Appl. No. 16/626,282 Non-Final Office Action dated Nov. 10, 2021.
U.S. Appl. No. 16/652,387 Final Office Action dated Mar. 10, 2022.
U.S. Appl. No. 17/152,506 Final Office Action dated Aug. 19, 2021.
U.S. Appl. No. 17/152,506 Non-Final Office Action dated Apr. 2, 2021.
Ushijima et al. Methylation-Sensitive Representational Difference Analysis (MS-RDA). Methods Mol Biol 507:117-130 (2009).
Weber et al. Chromosome-wide and promoter-specific analyses identify sites of differential DNA methylation in normal and transformed human cells. Nat. Genet. 37:853-862 (2005).
Wojdacz et al., Methylation-sensitive high resolution melting (MS-HRM): a new approach for sensitive and high-throughput assessment of methylation. Nucleic Acids Res 35(6):e41 (2007).
Wojdacz et al., Methylation-sensitive high-resolution melting. Nature Protocols 3(12): 1903-1908 (2008).
Xiong et al. COBRA: a sensitive and quantitative DNA methylation assay. Nucleic Acids Res. 25:2532-2534 (1997).
Yershov et al. DNA analysis and diagnostics on oligonucleotide microchips. PNAS USA 93(10):4913-4918 (1996).
Zhang et al., Temozolomide Mechanisms of Action, Repair and Resistance. Current Molecular Pharmacology 5(1): 102-114 (2012).
Zuckermann, et al. Efficient methods for attachment of thiol specific probes to the 3'-ends of synthetic oligodeoxyribonucleotides. Nucleic Acids Res. 15(13):5305-21 (1987).

\* cited by examiner

|  | $D_v$ (0.1) (μm) | $D_v$ (0.5) (μm) | $D_v$ (0.9) (μm) | Span (μm) |
|---|---|---|---|---|
| Non-micronised API | 189.6 | 402.3 | 687.2 | 1.2 |
| Micronised API | 6.4 | 18.3 | 40.5 | 1.9 |

INIPARIB FORMULATIONS AND USES THEREOF

CROSS-REFERENCE

This application is a U.S. National Phase of International Application No. PCT/US2018/053558 claims the benefit of U.S. Provisional Application No. 62/566,122, filed Sep. 29, 2017, which application is incorporated herein by reference in its entirety.

BACKGROUND

Malignant cancerous growths, due to their unique characteristics, pose serious challenges for modern medicine. In some instances, their characteristics include uncontrollable cell proliferation resulting in unregulated growth of malignant tissue, an ability to invade local and even remote tissues, lack of differentiation, lack of detectable symptoms and the lack of effective therapy and prevention.

SUMMARY

Included herein are compositions, methods and processes for treating malignant cancerous growths including iniparib or a pharmaceutically acceptable salt, solvate, metabolite, or prodrug thereof. The compositions, methods and processes disclosed herein provide improved dosage and administration, enabling enhanced bioavailability and efficacy to subjects in need thereof. The compositions, methods and processes disclosed herein also provide improved storage capabilities of the iniparib compositions.

In one aspect, described herein is an oral solid formulation, comprising:
 (i) iniparib or a pharmaceutically acceptable salt, solvate, metabolite, or prodrug thereof;
 (ii) at least one pharmaceutically acceptable excipient; and
 (iii) optionally one or more agents selected from the group consisting of surfactants, preservatives, flavoring agents, sweetening agents, and antifoaming agents;
 wherein a median particle size of iniparib or a pharmaceutically acceptable salt, solvate, metabolite, or prodrug thereof is from about 20 μm to about 400 μm; and wherein the formulation is stable at about 5±5° C. to about 25±5° C. for at least 12 months.

In another aspect, described herein is an oral dosage form comprising an immediate-release top layer and a controlled-release core, wherein said immediate-release layer comprises at least one of the stimulant, antihistamine, or antiemetic; and the controlled-release layer comprising a therapeutically effective amount of a formulation, comprising:
 (i) iniparib or a pharmaceutically acceptable salt, solvate, metabolite, or prodrug thereof;
 (ii) at least one pharmaceutically acceptable excipient; and
 (iii) optionally one or more agents selected from the group consisting of surfactants, preservatives, flavoring agents, sweetening agents, and antifoaming agents;
 wherein a median particle size of iniparib or a pharmaceutically acceptable salt, solvate, metabolite, or prodrug thereof is from about 20 μm to about 400 μm; and wherein the formulation is stable at about 5±5° C. to about 25±5° C. for at least 12 months.

In another aspect, described herein is an oral dosage form comprising an immediate-release top layer and a controlled-release core, wherein said immediate-release layer comprises at least one of the stimulant, antihistamine, or antiemetic; and the controlled-release layer comprising a therapeutically effective amount of a formulation, comprising:
 (i) a pharmaceutically acceptable salt of iniparib or a solvate, metabolite, or prodrug thereof;
 (ii) a buffer;
 (iii) a surfactant;
 (iv) water; and
 (v) optionally one or more agents selected from the group consisting of preservatives, flavoring agents, sweetening agents, antifoaming agent, and suspensions aids;
 wherein said formulation is an oral liquid formulation, and wherein said formulation is stable at about 5±5° C. to about 25±5° C. for at least 6 months.

In another aspect, described herein is a controlled-release iniparib formulation comprising a controlled-release matrix and from about 30 mg to about 400 mg of iniparib or a pharmaceutically acceptable salt, solvate, or prodrug thereof, wherein a median particle size of iniparib or a pharmaceutically acceptable salt, solvate, metabolite, or prodrug thereof is from about 20 n to about 400 μm; and wherein said formulation provides a maximum mean blood concentration of iniparib of between about 200 ng/ml and about 6000 ng/ml upon oral administration to a subject in need thereof.

In another aspect, described herein is a liquid formulation comprising:
 (i) a pharmaceutically acceptable salt of iniparib or a solvate, metabolite, or prodrug thereof;
 (ii) a buffer;
 (iii) a surfactant;
 (iv) water; and
 (v) optionally one or more agents selected from the group consisting of preservatives, flavoring agents, sweetening agents, antifoaming agent, and suspensions aids;
 wherein said formulation is an oral liquid formulation, and wherein said formulation is stable at about 5±5° C. to about 25±5° C. for at least 6 months.

In another aspect, described herein is an aqueous composition comprising a pharmaceutically acceptable salt of iniparib or a solvate, metabolite, or prodrug thereof, a pharmaceutically acceptable delivery vehicle, and a mucoadhesive agent, wherein the aqueous composition is formulated for transmucosal administration.

Yet, in another aspect, described herein is a method of treating cancer in a subject in need thereof comprising administering to the subject in need thereof a therapeutically effective amount of:
 (a) iniparib, or a pharmaceutically acceptable salt, solvate, metabolite, or prodrug thereof formulated as:
  (A1) an oral solid formulation comprising:
   (i) iniparib or a pharmaceutically acceptable salt, solvate, metabolite, or prodrug thereof;
   (ii) at least one pharmaceutically acceptable excipient; and
   (iii) optionally one or more agents selected from the group consisting of surfactants, preservatives, flavoring agents, sweetening agents, and antifoaming agents;
   wherein a median particle size of iniparib or a pharmaceutically acceptable salt, solvate, metabolite, or prodrug thereof is from about 20 μm to about 400 μm; and wherein the formulation is stable at about 5±5° C. to about 25±5° C. for at least 12 months;

(A2) an oral dosage form comprising an immediate-release top layer and a controlled-release core, wherein said immediate-release layer comprises at least one of the stimulant, antihistamine, or anti-emetic; and the controlled-release layer comprising a therapeutically effective amount of a formulation, comprising:
  (i) iniparib or a pharmaceutically acceptable salt, solvate, metabolite, or prodrug thereof;
  (ii) at least one pharmaceutically acceptable excipient; and
  (iii) optionally one or more agents selected from the group consisting of surfactants, preservatives, flavoring agents, sweetening agents, and antifoaming agents;
  wherein a median particle size of iniparib or a pharmaceutically acceptable salt, solvate, metabolite, or prodrug thereof is from about 20 μm to about 400 μm; and wherein the formulation is stable at about 5±5° C. to about 25±5° C. for at least 12 months;
(A3) an oral dosage form comprising an immediate-release top layer and a controlled-release core, wherein said immediate-release layer comprises at least one of the stimulant, antihistamine, or anti-emetic; and the controlled-release layer comprising a therapeutically effective amount of a formulation, comprising:
  (i) a pharmaceutically acceptable salt of iniparib or a solvate, metabolite, or prodrug thereof;
  (ii) a buffer;
  (iii) a surfactant;
  (iv) water; and
  (v) optionally one or more agents selected from the group consisting of preservatives, flavoring agents, sweetening agents, antifoaming agent, and suspensions aids;
  wherein said formulation is an oral liquid formulation, and wherein said formulation is stable at about 5±5° C. to about 25±5° C. for at least 6 months;
(A4) a controlled-release iniparib formulation comprising a controlled-release matrix and from about 30 mg to about 400 mg of iniparib or a pharmaceutically acceptable salt, solvate, or prodrug thereof, wherein a median particle size of iniparib or a pharmaceutically acceptable salt, solvate, metabolite, or prodrug thereof is from about 20 μm to about 400 μm; and wherein said formulation provides a maximum mean blood concentration of iniparib of between about 200 ng/ml and about 6000 ng/ml upon oral administration to a subject in need thereof; or
(A5) an oral liquid formulation comprising
  (i) a pharmaceutically acceptable salt of iniparib or a solvate, metabolite, or prodrug thereof;
  (ii) a buffer;
  (iii) a surfactant;
  (iv) water; and
  (v) optionally one or more agents selected from the group consisting of preservatives, flavoring agents, sweetening agents, antifoaming agent, and suspensions aids;
  wherein said formulation is an oral liquid formulation, and wherein said formulation is stable at about 5±5° C. to about 25±5° C. for at least 6 months;
(A6) an aqueous composition comprising a pharmaceutically acceptable salt of iniparib or a solvate, metabolite, or prodrug thereof, a pharmaceutically acceptable delivery vehicle, and a mucoadhesive agent, wherein the aqueous composition is formulated for transmucosal administration;
(b) about 0 mg/m$^2$ to about 90 mg/m$^2$ of temozolomide; and
(c) optionally radiation.

DETAILED DESCRIPTION

Figures 1, 2:
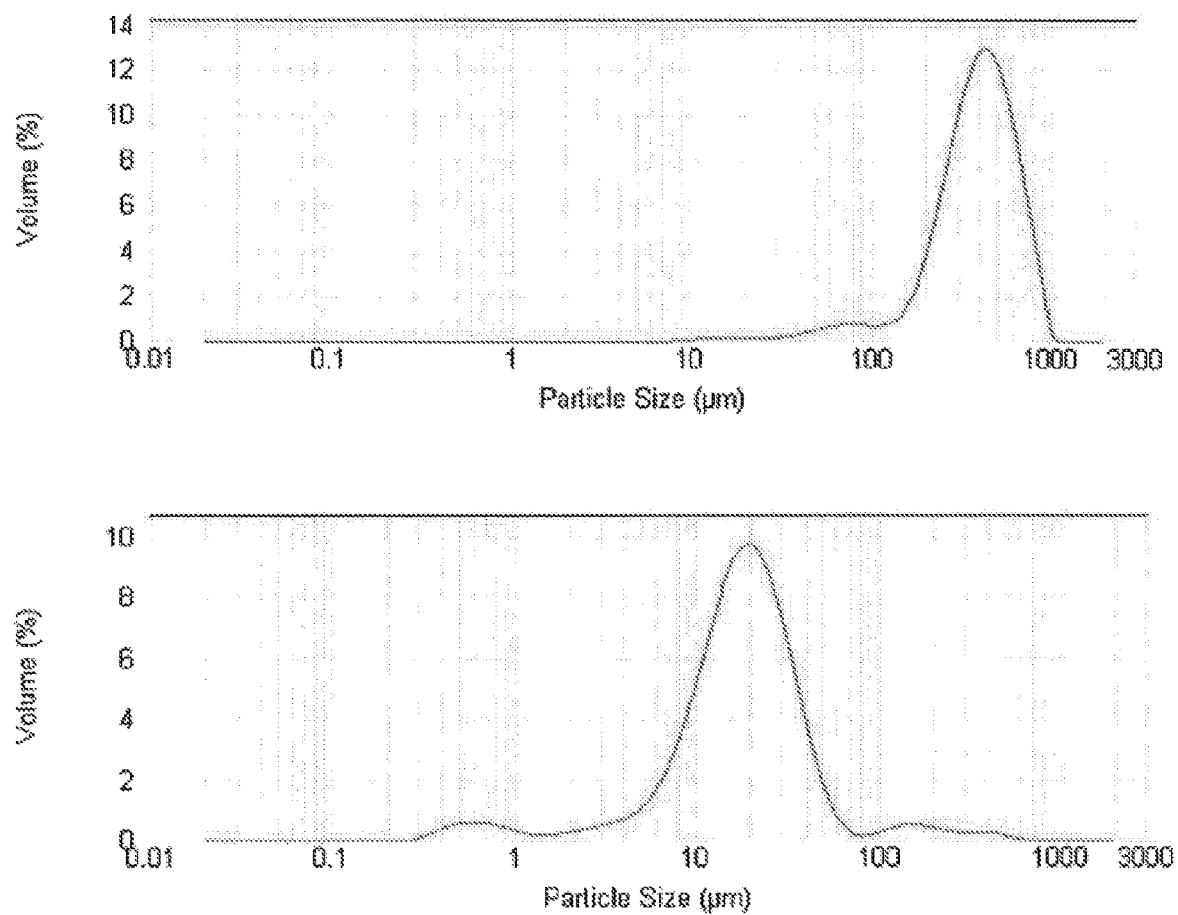
FIG. 1 illustrates median particle size results for non-micronized and micronized iniparib.
FIG. 2 illustrates representative particle size distribution for non-micronized iniparib (top) and representative particle size distribution for micronized iniparib (bottom).

Iniparib (4-iodo-3-nitrobenzamide, BA, BSI 201) is a small molecule that acts on tumor cells. In some instances, iniparib achieves its anti-neoplastic effect by inhibition of the DNA repair enzyme, poly [ADP-ribose] polymerase 1 (PARP1), leading to tumor cell apoptosis. In some cases, a low potency of iniparib against PARP1 is also observed in several studies, suggesting the presence of additional mechanisms of activity. Iniparib is lipophilic and distributes rapidly and widely into tissues, including the brain and cerebrospinal fluid (CSF). In some cases, iniparib is observed to be active against a broad range of cancer cells in vitro, including, e.g., against drug resistant cell lines.

Iniparib has a low solubility in purified water with a solubility of about 0.182 mg/mL. In some instances, the low solubility of iniparib poses a challenge in developing suitable formulations for cancer treatment. Formulations comprising iniparib with improved solubility enables enhanced bioavailability and efficacy, a lower administration dose, lower cytotoxicity, and decreased side effects.

In certain embodiments, described herein are pharmaceutical formulations of iniparib or a pharmaceutically acceptable salt, solvate, metabolite, or prodrug thereof, that have enhanced solubility in water. In some instances, the pharmaceutical formulations of iniparib or a pharmaceutically acceptable salt, solvate, metabolite, or prodrug thereof, have enhanced bioavailability and efficacy, have a lower administration dose, a lower cytotoxicity, and have decreased side effects. In some cases, iniparib or a pharmaceutically acceptable salt, solvate, metabolite, or prodrug thereof, is formulated as a solid formulation. In other cases, iniparib or a pharmaceutically acceptable salt, solvate, metabolite, or prodrug thereof, is formulated as a liquid formulation. In additional cases, iniparib or a pharmaceutically acceptable salt, solvate, metabolite, or prodrug thereof is formulated as an aerosol formulation.

In some embodiments, iniparib or a pharmaceutically acceptable salt, solvate, metabolite, or prodrug thereof disclosed herein is 4-iodo-3-nitrobenzamide. In some instances, 4-iodo-3-nitrobenzamide has the structure:

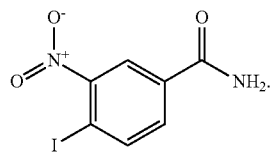 [SMILES: NC(=O)c1ccc(I)c([N+](=O)[O-])c1]

In some embodiments, the antitumor activity of iniparib in tumor cell lines is achieved using iniparib metabolites. In some embodiments, disclosed herein is a pharmaceutical formulation comprising iniparib metabolite derived from iniparib or a salt, solvate, or prodrug thereof. In some embodiments, the iniparib metabolite is selected from the group consisting of:
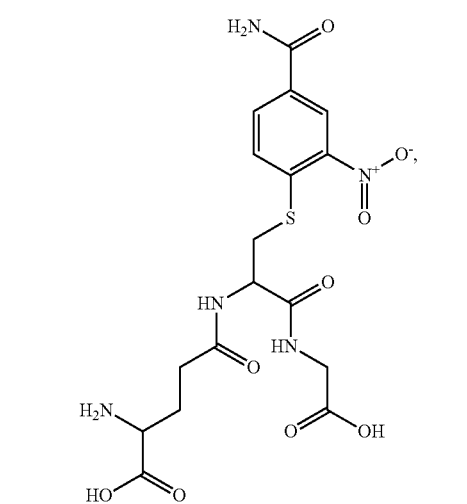
MS472
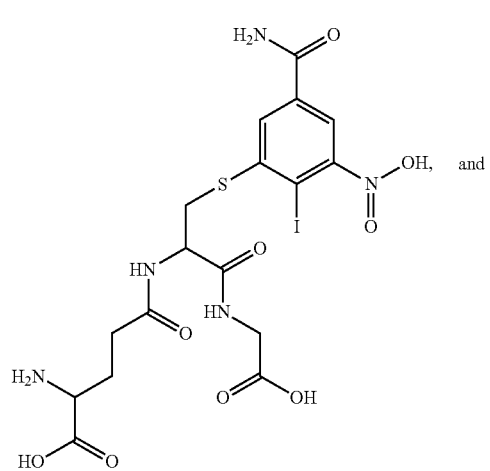
MS601
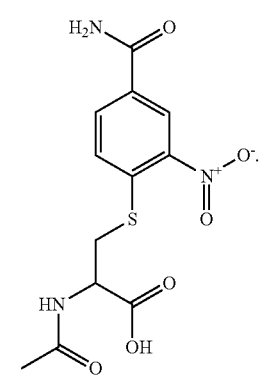
MS328
In some embodiments, the iniparib metabolite is selected from the group consisting of:
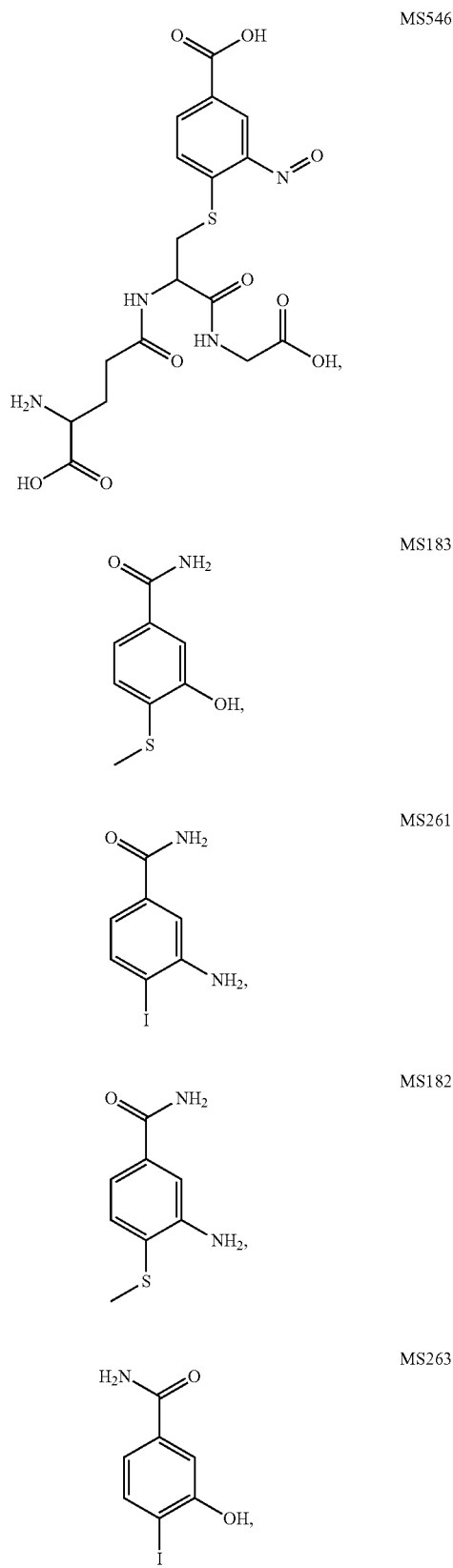

MS276
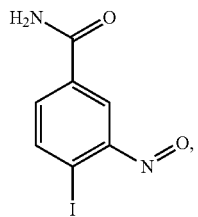

MS278
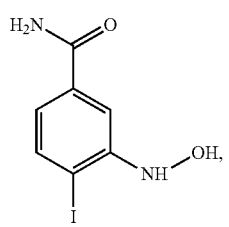

MS635a
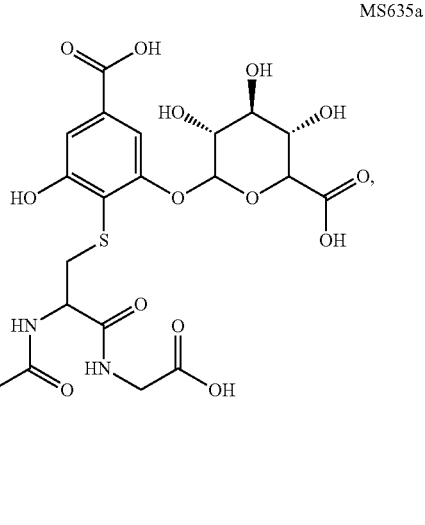

MS635b
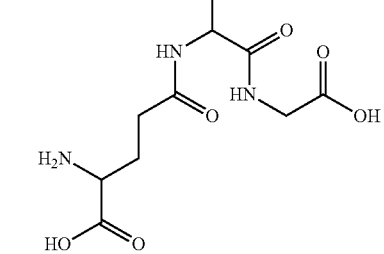

MS471
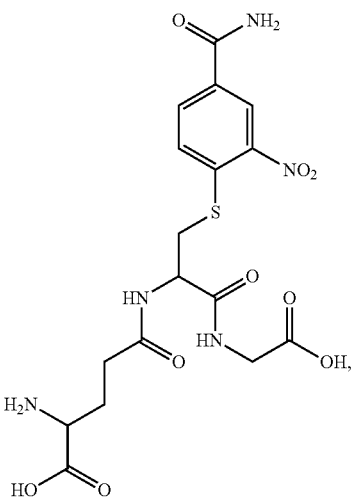

MS414
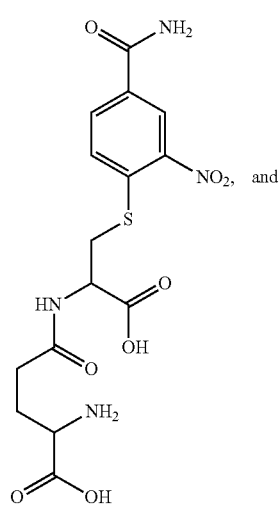

and

MS692
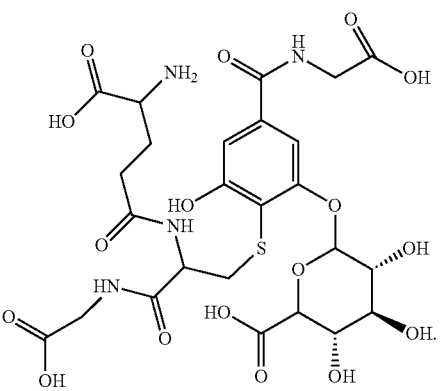

One wax to improve bioavailability of iniparib is to reduce a median particle size of iniparib or a pharmaceutically acceptable salt, solvate, metabolite, or prodrug thereof in a solid formulation. In some embodiments, disclosed herein are pharmaceutical formulations of iniparib or a pharmaceutically acceptable salt, solvate, metabolite, or prodrug thereof, having a reduced median particle size of the iniparib active ingredient.

Oral Solid Formulations

In some embodiments, described herein are solid formulations comprising an iniparib active ingredient. In some instances, the solid formulation comprising iniparib or a pharmaceutically acceptable salt, solvate, metabolite, or prodrug thereof, has an enhanced bioavailability and efficacy, has a lower administration dose, a lower cytotoxicity, and has decreased side effects. In some instances, the solid formulation comprising iniparib or a pharmaceutically acceptable salt, solvate, metabolite, or prodrug thereof, has a reduced median particle size of the iniparib active ingredient, for improving bioavailability.

In some embodiments, the solid formulation is an oral solid formulation. In some instances, the oral solid formulation comprising iniparib or a pharmaceutically acceptable salt, solvate, metabolite, or prodrug thereof, has an enhanced bioavailability and efficacy, has a lower administration dose, a lower cytotoxicity, and has decreased side effects. In some instances, the oral solid formulation comprising iniparib or a pharmaceutically acceptable salt, solvate, metabolite, or prodrug thereof, has a reduced median particle size of the iniparib active ingredient, for improving bioavailability.

In some embodiments, the oral solid formulation comprises:
(i) iniparib or a pharmaceutically acceptable salt, solvate, metabolite, or prodrug thereof;
(ii) at least one pharmaceutically acceptable excipient; and
(iii) optionally one or more agents selected from the group consisting of surfactants, preservatives, flavoring agents, sweetening agents, and antifoaming agents;
wherein median particle size of iniparib or a pharmaceutically acceptable salt, solvate, metabolite, or prodrug thereof is from about 20 µm to about 400 µm; and
wherein the formulation is stable at about 5±5° C. to about 25±5° C. for at least 12 months.

In some embodiments, the metabolite of iniparib is selected from the group consisting of: 4-iodo-3-nitrosobenzamide, 3-(hydroxyamino)-4-iodobenzamide, 3-hydroxy-4-iodobenzamide, 4-(methylthio)-3-nitrobenzamide, and N5-(3-((4-carbamoyl-2-nitrophenyl)thio)-1-((carboxymethyl)amino)-1-oxopropan-2-yl)glutamine. In some embodiments, the metabolite of iniparib is 4-iodo-3-nitrosobenzamide. In some embodiments, the metabolite of iniparib is 3-(hydroxyamino)-4-iodobenzamide. In some embodiments, the metabolite of iniparib is 3-hydroxy-4-iodobenzamide. In some embodiments, the metabolite of iniparib is 4-(methylthio)-3-nitrobenzamide. In some embodiments, the metabolite of iniparib is N5-(3-((4-carbamoyl-2-nitrophenyl)thio)-1-((carboxymethyl)amino)-1-oxopropan-2-yl)glutamine.

In some embodiments, the pharmaceutically acceptable excipient is selected from the group consisting of fillers, binders, suspending agents, disintegrants, lubricants, and combinations thereof.

In some embodiments, the oral solid formulation comprises a filler. In some embodiments, the filler is pregelatinized starch. In some embodiments, the amount of pregelatinized starch is from about 20% to about 40% by weight. In some embodiments, the amount of pregelatinized starch is about 20% w/w, about 21% w/w, about 22% w/w, about 23% w/w, about 24% w/w, about 25% w/w, about 26% w/w, about 27% w/w, about 28% w/w, about 29% w/w, about 30% w/w, about 31% w/w, about 32% w/w, about 33% w/w, about 34% w/w, about 35% w/w, about 36% w/w, about 37% w/w, about 38% w/w, about 39% w/w, or about 40% w/w.

In some embodiments, the oral solid formulation comprises a binder. In some embodiments, the binder is microcrystalline cellulose. In some embodiments, the amount of microcrystalline cellulose is from about 15% to about 25% by weight. In some embodiments, the amount of microcrystalline cellulose is about 15% w/w, about 16% w/w, about 17% w/w, about 18% w/w, about 19% w/w, about 20% w/w, about 21% w/w, about 22% w/w, about 23% w/w, about 24% w/w, or about 25% w/w.

In some embodiments, the oral solid formulation comprises a suspending agent. In some embodiments, the suspending agent is polyvinylpyrrolidone. In some embodiments, the amount of polyvinylpyrrolidone is from about 1% to about 4% by weight. In some embodiments, the amount of polyvinylpyrrolidone is about 1% w/w, about 1.1% w/w, about 1.2% w/w, about 1.3% w/w, about 1.4% w/w, about 1.5% w/w, about 1.6% w/w, about 1.7% w/w, about 1.8% w/w, about 1.9% w/w, about 2% w/w, about 2.1% w/w, about 2.2% w/w, about 2.3% w/w, about 2.4% w/w, about 2.5% w/w, about 2.6% w/w, about 2.7% w/w, about 2.8% w/w, about 2.9% w/w, about 3% w/w, about 3.1% w/w, about 3.2% w/w, about 3.3% w/w, about 3.4% w/w, about 3.5% w/w, about 3.6% w/w, about 3.7% w/w, about 3.8% w/w, about 3.9% w/w, or about 4% w/w.

In some embodiments, the oral solid formulation comprises a disintegrant. In some embodiments, the disintegrant is sodium starch glycollate. In some embodiments, the amount of sodium starch glycollate is from about 1% to about 6% by weight. In some embodiments, the amount of sodium starch glycollate is about 1% w/w, about 1.1% w/w, about 1.2% w/w, about 1.3% w/w, about 1.4% w/w, about 1.5% w/w, about 1.6% w/w, about 1.7% w/w, about 1.8% w/w, about 1.9% w/w, about 2% w/w, about 2.1% w/w, about 2.2% w/w, about 2.3% w/w, about 2.4% w/w, about 2.5% w/w, about 2.6% w/w, about 2.7% w/w, about 2.8% w/w, about 2.9% w/w, about 3% w/w, about 3.1% w/w, about 3.2% w/w, about 3.3% w/w, about 3.4% w/w, about 3.5% w/w, about 3.6% w/w, about 3.7% w/w, about 3.8% w/w, about 3.9% w/w, about 4% w/w, about 4.1% w/w, about 4.2% w/w, about 4.3% w/w, about 4.4% w/w, about 4.5% w/w, about 4.6% w/w, about 4.7% w/w, about 4.8% w/w, about 4.9% w/w, about 5% w/w, about 5.1% w/w, about 5.2% w/w, about 5.3% w/w, about 5.4% w/w, about 5.5% w/w, about 5.6% w/w, about 5.7% w/w, about 5.8% w/w, about 5.9% w/w, or about 6% w/w.

In some embodiments, the oral solid formulation comprises a lubricant. In some embodiments, the lubricant is magnesium stearate. In some embodiments, the amount of magnesium stearate is from about 1% to about 3% by weight. In some embodiments, the amount of magnesium stearate is from about 1% w/w, about 1.1% w/w, about 1.2% w/w, about 1.3% w/w, about 1.4% w/w, about 1.5% w/w, about 1.6% w/w, about 1.7% w/w, about 1.8% w/w, about 1.9% w/w, about 2% w/w, about 2.1% w/w, about 2.2% w/w, about 2.3% w/w, about 2.4% w/w, about 2.5% w/w, about 2.6% w/w, about 2.7% w/w, about 2.8% w/w, about 2.9% w/w, or about 3% w/w.

In some embodiments, the oral formulation comprises a surfactant. In some embodiments, the amount of the surfactant is from about 0.5% to about 10% by weight. In some embodiments, the amount of the surfactant is about 0.5%, about 0.6%, about 0.7%, about 0.8%, about 0.9%, about 1.0%, about 1.1%, about 1.2%, about 1.3%, about 1.4%, about 1.5%, about 1.6%, about 1.7%, about 1.8%, about 1.9%, about 2.0%, about 2.1%, about 2.2%, about 2.3%, about 2.4%, about 2.5%, about 2.6%, about 2.7%, about 2.8%, about 2.9%, about 3.0%, about 3.1%, about 3.2%, about 3.3%, about 3.4%, about 3.5%, about 3.6%, about 3.7%, about 3.8%, about 3.9%, about 4.0%, about 4.1%, about 4.2%, about 4.3%, about 4.4%, about 4.5%, about 4.6%, about 4.7%, about 4.8%, about 4.9%, or about 5.0% by weight.

In some embodiments, the surfactant is sodium lauryl sulfate. In some embodiments, the amount of sodium lauryl sulfate is from about 0.5% to about 5% by weight. In some embodiments, the amount of sodium lauryl sulfate is about 0.5% by weight. In some embodiments, the amount of sodium lauryl sulfate is about 1.0% by weight. In some embodiments, the amount of sodium lauryl sulfate is about 2.0% by weight. In some embodiments, the amount of sodium lauryl sulfate is about 3.0% by weight. In some embodiments, the amount of sodium lauryl sulfate is about 4.0% by weight. In some embodiments, the surfactant is poloxamer 188. In some embodiments, the amount of poloxamer 188 is from about 7% to about 15% by weight. In some embodiments, the surfactant is polysorbate 80. In some embodiments, the amount of polysorbate 80 is from about 0.5% to about 2% by weight.

In some embodiments, the median particle size of iniparib or a pharmaceutically acceptable salt, solvate, metabolite, or prodrug thereof is about 20 μm or more. In some embodiments, the median particle size of iniparib or a pharmaceutically acceptable salt, solvate, metabolite, or prodrug thereof is about 50 μm or more. In some embodiments, the median particle size of iniparib or a pharmaceutically acceptable salt, solvate, metabolite, or prodrug thereof is about 100 μm or more. In some embodiments, the median particle size of iniparib or a pharmaceutically acceptable salt, solvate, metabolite, or prodrug thereof is about 150 μm or more. In some embodiments, the median particle size of iniparib or a pharmaceutically acceptable salt, solvate, metabolite, or prodrug thereof is about 200 μm or more. In some embodiments, the median particle size of iniparib or a pharmaceutically acceptable salt, solvate, metabolite, or prodrug thereof is about 250 μm or more. In some embodiments, the median particle size of iniparib or a pharmaceutically acceptable salt, solvate, metabolite, or prodrug thereof is about 300 μm or more. In some embodiments, the median particle size of iniparib or a pharmaceutically acceptable salt, solvate, metabolite, or prodrug thereof is about 350 μm or more. In some embodiments, the median particle size of iniparib or a pharmaceutically acceptable salt, solvate, metabolite, or prodrug thereof is about 400 μm or more.

In some embodiments, the median particle size of iniparib or a pharmaceutically acceptable salt, solvate, metabolite, or prodrug thereof is about 15 μm or more, about 16 μm or more, about 17 μm or more, about 18 μm or more, about 19 μm or more, about 20 μm or more, about 21 μm or more, about 22 μm or more, about 23 μm or more, about 24 μm or more, about 25 μm or more, about 26 μm or more, about 27 μm or more, about 28 μm or more, about 29 μm or more, about 30 μm or more, about 31 μm or more, about 32 μm or more, about 33 μm or more, about 34 μm or more, about 35 μm or more, about 36 μm or more, about 37 μm or more, about 38 μm or more, about 39 μm or more, about 40 μm or more, about 41 μm or more, about 42 μm or more, about 43 μm or more, about 44 μm or more, about 45 μm or more, about 46 μm or more, about 47 μm or more, about 48 μm or more, about 49 μm or more, about 50 μm or more, about 51 μm or more, about 52 μm or more, about 53 μm or more, about 54 μm or more, about 55 μm or more, about 56 μm or more, about 57 μm or more, about 58 μm or more, about 59 μm or more, about 60 μm or more, about 61 μm or more, about 62 μm or more, about 63 μm or more, about 64 μm or more, about 65 μm or more, about 66 μm or more, about 67 μm or more, about 68 μm or more, about 69 μm or more, about 70 μm or more, about 71 μm or more, about 72 μm or more, about 73 μm or more, about 74 μm or more, about 75 μm or more, about 76 μm or more, about 77 μm or more, about 78 μm or more, about 79 μm or more, about 80 μm or more, about 81 μm or more, about 82 μm or more, about 83 μm or more, about 84 μm or more, about 85 μm or more, about 86 μm or more, about 87 μm or more, about 88 μm or more, about 89 μm or more, or about 90 μm or more.

In some embodiments, the median particle size of iniparib or a pharmaceutically acceptable salt, solvate, metabolite, or prodrug thereof is about 15 μm, about 16 μm, about 17 μm, about 18 μm, about 19 μm, about 20 μm, about 21 μm, about 22 μm, about 23 μm, about 24 μm, about 25 μm, about 26 μm, about 27 μm, about 28 μm, about 29 μm, about 30 μm, about 31 μm, about 32 μm, about 33 μm, about 34 μm, about 35 μm, about 36 μm, about 37 μm, about 38 μm, about 39 μm, about 40 μm, about 41 μm, about 42 μm, about 43 μm, about 44 μm, about 45 μm, about 46 μm, about 47 μm, about 48 μm, about 49 μm, about 50 μm, about 51 μm, about 52 μm, about 53 μm, about 54 μm, about 55 μm, about 56 μm, about 57 μm, about 58 μm, about 59 μm, about 60 μm, about 61 μm, about 62 μm, about 63 μm, about 64 μm, about 65 μm, about 66 μm, about 67 μm, about 68 μm, about 69 μm, about 70 μm, about 71 μm, about 72 μm, about 73 μm, about 74 μm, about 75 μm, about 76 μm, about 77 μm, about 78 μm, about 79 μm, about 80 μm, about 81 μm, about 82 μm, about 83 μm, about 84 μm, about 85 μm, about 86 μm, about 87 μm, about 88 μm, about 89 μm, or about 90 μm.

In some embodiments, the oral formulation is a tablet or capsule. In some embodiments, the oral formulation is a capsule. In some embodiments, the oral formulation is a tablet.

In some embodiments, iniparib or a pharmaceutically acceptable salt, solvate, metabolite, or prodrug thereof is present in an amount of at least about 10 mg. In some embodiments, the amount of iniparib or a pharmaceutically acceptable salt, solvate, metabolite, or prodrug thereof is from about 10 mg to about 400 mg. In some embodiments, the amount of iniparib or a pharmaceutically acceptable salt, solvate, metabolite, or prodrug thereof is from about 20 mg to about 300 mg. In some embodiments, the amount of iniparib or a pharmaceutically acceptable salt, solvate, metabolite, or prodrug thereof is from about 30 mg to about 200 mg. In some embodiments, the amount of iniparib or a pharmaceutically acceptable salt, solvate, metabolite, or prodrug thereof is about 10 mg, about 20 mg, about 30 mg, about 33.3 mg, about 40 mg, about 50 mg, about 66.6 mg, about 75 mg, about 100 mg, about 150 mg, or about 200 mg.

In some embodiments, the oral solid formulation comprises a preservative. In some embodiments, the preservative is selected from the group consisting of sodium benzoate, a paraben or paraben salt, and combinations thereof. In some embodiments, the amount of preservative is about 0.1% to about 2% by weight.

In some embodiments, the oral liquid formulation comprises an antifoaming agent. In some embodiments, the antifoaming agent is simethicone. In some embodiments, the amount of simethicone is from about 0.1% to about 1% by weight.

In some embodiments, the formulation comprises a flavoring agent.

In some embodiments, the oral liquid formulation comprises a sweetener.

In some embodiments, the formulation is stable at about 5±5° C. for at least 2 months. In some embodiments, the formulation is stable at about 5±5° C. for at least 4 months. In some embodiments, the formulation is stable at about 5±5° C. for at least 6 months. In some embodiments, the formulation is stable at about 5±5° C. for at least 9 months. In some embodiments, the formulation is stable at about 5±5° C. for at least 12 months. In some embodiments, the formulation is stable at about 5±5° C. for at least 15 months. In some embodiments, the formulation is stable at about 5±5° C. for at least 18 months. In some embodiments, the formulation is stable at about 5±5° C. for at least 24 months. In some embodiments, the formulation is stable at about 5±5° C. for at least 30 months. In some embodiments, the formulation is stable at about 5±5° C. for at least 36 months.

In some embodiments, the formulation is stable at about 25±5° C. for at least 2 months. In some embodiments, the formulation is stable at about 25±5° C. for at least 4 months. In some embodiments, the formulation is stable at about 25±5° C. for at least 6 months. In some embodiments, the formulation is stable at about 25±5° C. for at least 9 months. In some embodiments, the formulation is stable at about 25±5° C. for at least 12 months. In some embodiments, the formulation is stable at about 25±5° C. for at least 15 months. In some embodiments, the formulation is stable at about 25±5° C. for at least 18 months. In some embodiments, the formulation is stable at about 25±5° C. for at least 24 months.

Bi-Layer Formulations

In some embodiments, the solid formulation is a bi-layer formulation. In some instances, the bi-layer formulation comprising iniparib or a pharmaceutically acceptable salt, solvate, metabolite, or prodrug thereof, has an enhanced bioavailability and efficacy, has a lower administration dose, a lower cytotoxicity, and has decreased side effects. In some instances, the bi-layer formulation comprising iniparib or a pharmaceutically acceptable salt, solvate, metabolite, or prodrug thereof, has a reduced median particle size of the iniparib active ingredient, for improving bioavailability.

In some embodiments, the bi-layer formulation is an oral dosage form comprising an immediate-release top layer and a controlled-release core, wherein said immediate-release layer comprises at least one of the stimulant, antihistamine, or antiemetic; and the controlled-release layer comprising a therapeutically effective amount of a formulation, comprising:
  (i) iniparib or a pharmaceutically acceptable salt, solvate, metabolite, or prodrug thereof;
  (ii) at least one pharmaceutically acceptable excipient; and
  (iii) optionally one or more agents selected from the group consisting of surfactants, preservatives, flavoring agents, sweetening agents, and antifoaming agents;
  wherein median particle size of iniparib or a pharmaceutically acceptable salt, solvate, metabolite, or prodrug thereof is from about 20 μm to about 400 μm; and
  wherein the formulation is stable at about 5±5° C. to about 25±5° C. for at least 12 months.

In other embodiments, the bi-layer formulation is an oral dosage form comprising an immediate-release top layer and a controlled-release core, wherein said immediate-release layer comprises at least one of the stimulant, antihistamine, or antiemetic; and the controlled-release layer comprising a therapeutically effective amount of a formulation, comprising:
  (i) a pharmaceutically acceptable salt of iniparib or a solvate, metabolite, or prodrug thereof;
  (ii) a buffer;
  (iii) a surfactant;
  (iv) water; and
  (v) optionally one or more agents selected from the group consisting of preservatives, flavoring agents, sweetening agents, antifoaming agent, and suspensions aids;
  wherein said formulation is an oral liquid formulation, and
  wherein said formulation is stable at about 5±5° C. to about 25±5° C. for at least 6 months.

In some embodiments, the stimulant is selected from the group consisting of aminophylline, caffeine, dyphlline, oxitriphylline, theophhylline, amphetamine, benzphetamine, dextroamphetamine, diethylpropion, mazindol, methamphetamine, methylphenidate, dexmethylphenidate, pemoline, sibutramine, modafinil, atomoxetine, phendimetrizine, phenteramine, adrafinil, phenylpropanolamine, psuedoephedrine, synephrine, amphetaminil, furfenorex, or a combination thereof.

In some embodiments, the antiemetic is selected from the group consisting of aprepitant, dronabinol, perphenazine, palonosetron, trimethobenzamide, metoclopromide, domperidone, prochlorperazine, promethazine, chlorpromazine, trimethobenzamide, ondansetron, granisetron, hydroxyzine, acetylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxyperndyl, pipamazine, scopolamine, sulpiride, tetrahydrocannabinol, thiethylperazine, thioproperazine, tropisetron, droperidol, haloperidol, prochloperazine, metoclopramide, diphenhydramine, *cannabis*, midazolam, lorazepam, hyoscine, dexamethasone, emetrol, propofol and mixtures thereof.

In some embodiments, the antihistamine is selected from the group consisting of 2-(m-fluorophenyl)-histamine, chlorpheniramine, mepyramine, terfenadine, astemizole, triprolidine, ethanolamines carbinoxamine, diphenhydramine, doxylamine, pyrilamine, tripelennamine, hydroxyzine, fexofenadine, brompheniramine chlorpheniramine, cyproheptadine, loratadine, cetirizine, dimaprit, impromidine, amthamine, cimetidine, ranitidine, nizatidine, famotidine, R-alpha-methylhistamine, imetit, immepip, thioperamide, iodophenpropit, clobenpropit, clobenpropit, imetit, clozapine, thioperamide, azelastine, brompheniramine, carbinoxamine, cetrizine, chlorpheniramine, clemastine, cyclizine, cyproheptadine, desloratidine, dimenhydrinate, diphenhydramine, emedastine, fexofenadine, ketotifen, levocabastine, loratadine, meclizine, olopatadine, phenindamine, promethazine, or a combination thereof.

In some embodiments, the dosage form comprises an additional controlled-release layer comprising a therapeutically effective amount of an anticancer agent. In some embodiments, the anticancer agent is selected from the group consisting of carboplatin, gefitinib, gemcitabine, irinotecan, paclitaxel, picropodophyllin, topotecan, temozolomide, or a combination thereof.

Controlled-Release Coating Formulations

In some embodiments, at least one controlled-release coating surrounds the core of the oral dosage form. In certain embodiments the controlled-release coating is a stable controlled-release monolithic coating that is formed by a process that comprises coating the core with a coating composition to form a coated core with an intermediate coating, and curing the coated core to form the stable controlled-release coating. In at least one embodiment the coating composition comprises an aqueous dispersion of a neutral ester copolymer without any functional groups, a poly glycol having a melting point of at least 55° C., and one or more second pharmaceutically acceptable excipients. The curing is conducted at a temperature at least equal to or greater than the melting point of the poly glycol. In at least one embodiment the stable controlled-release coating comprises a neutral ester copolymer without any functional groups, a poly glycol having a melting point of at least 55° C., and one or more second pharmaceutically acceptable excipients.

The coating composition comprises an aqueous dispersion of a neutral ester copolymer without any functional groups. The aqueous dispersion of a neutral ester copolymer without any functional groups might be an ethyl acrylate and methyl methacrylate copolymer dispersion. Non-limiting examples of ethyl acrylate and methyl methacrylate copolymer dispersions include a 30% aqueous dispersion of a neutral copolymer based on ethyl acrylate and methyl methacrylate (e.g. Eudragit® NE30D), a 40% aqueous dispersion of a neutral copolymer based on ethyl acrylate and methyl methacrylate (e.g. Eudragit® NE40D), Eudragit® NM30D, Kollicoat® EMM30D, and combinations thereof. In at least one embodiment the neutral ester copolymer without any functional groups used in the controlled-release coating composition is Eudragit® NE30D, Eudragit® NE40D, or a mixture thereof. The neutral ester copolymer without any functional groups might be present in certain embodiments in an amount of from about 1% to about 35% by weight of the coating composition, depending on the therapeutically active agent used and the controlled-release profile desired. In certain embodiments the neutral ester copolymer without any functional groups is present in an amount from about 20% to about 99.5% by dry weight of the coat. In other embodiments the neutral ester copolymer without any functional groups is present in an amount from about 25% to about 60% by dry weight of the coat. In still other embodiments the neutral ester copolymer without any functional groups is present in an amount from about 37% to about 50% by dry weight of the coat. In some embodiments, the neutral ester copolymer without any functional groups is present in an amount of about 38%, about 39%, about 40%, about 41%, about 42%, about 43%, about 44%, about 45%, about 46%, about 47%, about 48%, and about 49% by dry weight of the coat. In certain embodiments, the neutral ester copolymer without any functional groups is present in the coating composition in an amount of from about 0.4% to about 39.8% by dry weight of the tablet. in other embodiments in an amount of from about 0.8% to about 24.0% by dry weight of the tablet. In some other embodiments, the neutral ester copolymer without any functional groups is present in the coating composition in an amount of from about 2.0% to about 5.5% by dry weight of the tablet, for example, about 2.1%, about 2.2%, about 2.3%, about 2.4%, about 2.5%, about 2.6%, about 2.7%, about 2.8%, about 2.9%, about 3.0%, about 3.1%, about 3.2%, about 3.3%, about 3.4%, about 3.5%, about 3.6%, about 3.7%, about 3.8%, about 3.9%, about 4.0%, about 4.1%, about 4.2%, about 4.3%, about 4.4%, about 4.5%, about 4.6%, about 4.7%, about 4.8%, about 4.9%, about 5.0%, about 5.1%, about 5.2%, about 5.3%, about 5.4% by dry weight of the tablet.

In some embodiments, the controlled-release dosage form does not swell in a dimensionally unrestricted manner upon imbibition of water. In certain embodiments there is some swelling of the controlled-release dosage form in a dimensionally restricted manner upon imbibition of water. In certain embodiments the controlled-release coating restricts the swelling of the dosage form upon imbibition of water.

The coating composition also comprises a poly glycol with a melting point of at least about 55° C. The poly glycol with a melting point of at least about 55° C. might be a polyethylene glycol with an average molecular weight ranging from about 4,000 Daltons to about 35,000 Daltons. Non-limiting examples of a poly glycol with a melting point of at least about 55° C. that might be used with the coating compositions include polyethylene glycol 4000, polyethylene glycol 4600, polyethylene glycol 6000, polyethylene glycol 8000, polyethylene glycol 10000, polyethylene glycol 12000, polyethylene glycol 20000, polyethylene glycol 35000, and mixtures thereof. In certain embodiments, the poly glycol is selected from the group consisting of polyethylene glycol 6000, polyethylene glycol 8000, polyethylene glycol 10000, polyethylene glycol 12000, and mixtures thereof. In at least one embodiment the poly glycol used in the coating composition is polyethylene glycol 8000. The poly glycol might be present in certain embodiments in an amount of from about 0.1% to about 10% by weight of the coating composition. In certain embodiments the poly glycol is present in an amount of from about 0.5% to about 28% by dry weight of the coat. In other embodiments the poly glycol is present in an amount from about 4% to about 17% by dry weight of the coat. In still other embodiments the poly glycol is present in an amount from about 7.2% to about 15.2% by dry weight of the coat, for example, about 7.3%, about 7.4%, about 7.5%, about 7.6%, about 7.7%, about 7.8%, about 7.9%, about 8.0%, about 8.1%, about 8.2%, about 8.3%, about 8.4%, about 8.5%, about 8.6%, about 8.7%, about 8.8%, about 8.9%, about 9.0%, about 9.1%, about 9.2%, about 9.3%, about 9.4%, about 9.5%, about 9.6%, about 9.7%, about 9.8%, about 9.9%, about 10.0%, about 10.1%, about 10.2%, about 10.3%, about 10.4%, about 10.5%, about 10.6%, about 10.7%, about 10.8%, about 10.9%, about 11.0%, about 11.1%, about 11.2%, about 11.3%, about 11.4%, about 11.5%, about 11.6%, about 11.7%, about 11.8%, about 11.9%, about 12.0%, about 12.1%, about 12.2%, about 12.3%, about 12.4%, about 12.5%, about 12.6%, about 12.7%, about 12.8%, about 12.9%, about 13.0%, about 13.1%, about 13.2%, about 13.3%, about 13.4%, about 13.5%, about 13.6%, about 13.7%, about 13.8%, about 13.9%, about 14.0%, about 14.1%, about 14.2%, about 14.3%, about 14.4%, about 14.5%, about 14.6%, about 14.7%, about 14.8%, about 14.9%, about 15.0%, and about 15.1% by dry weight of the coat. In certain embodiments the poly glycol is present in the coating composition in an amount of from about 0.1% to about 11.2% by dry weight of the tablet. In other embodiments the poly glycol is present in the coating composition in an amount of from about 0.1% to about 8.0% by dry weight of the tablet. In still other embodiments the poly glycol is present in the coating composition in an amount of from about 0.2% to about 2.8% by dry weight of the tablet, for example, about 0.3%, about 0.4%, about 0.5%, about 0.6%, about 0.7%, about 0.8%, about 0.9%, about 1.0%, about 1.1%, about 1.2%, about 1.3%, about 1.4%, about 1.5%, about 1.6%, about 1.7%, about 1.8%, about 1.9%, about 2.0%, about 2.1%, about 2.2%, about 2.3%, about 2.4%, about 2.5%, about 2.6%, and about 2.7% by dry weight of the tablet. Other suitable polyglycol derivatives having a melting point of at least about 55° C. might be, but are not limited to, Poloxamer 188, Poloxamer 338, Poloxamer 407, Polyethylene Oxides, Polyoxyethylene Alkyl Ethers, Polyoxyethylene Stearates, and mixtures thereof.

In addition to the copolymers and the poly glycol, the coating composition comprises one or more other pharmaceutically acceptable excipients. The excipients can include, but not limited to, anti-tacking agents, emulsifying agents, antifoaming agents, hydrophilic agents, flavorings, colorants, sweeteners etc, and any combination thereof. In some embodiments, excipients might affect the properties of the coat in a series of ways, and many substances used in coat formulations might thus be described as multifunctional. A skilled worker will know, based on his technical knowledge, which pharmaceutically acceptable excipients are suitable for the desired controlled-release coating composition.

Hydrophilic agents might be included in the coat to promote wetting of the coat when in contact with gastrointestinal fluids. Such hydrophilic agents include hydrophilic water soluble polymers such as hydroxypropyl methylcellulose (HPMC) (e.g. Pharmacoat® 606 or Hypromellose), hydroxypropyl cellulose (HPC), methyl cellulose, hydroxyethyl cellulose, hydroxyethyl methylcellulose, polyvinylpyrrolidone (Povidone® or Kollidon®), polyvinyl alcohol, polyethylene oxide, vinylpyrrolidone-vinyl acetate copolymer (Kollidon® VA64), polyethylene glycol-polyvinyl alcohol copolymer (Kollicoat® IR), copolymers thereof, and combinations thereof. In at least one embodiment, HPMC is the hydrophilic agent used in the coating composition. In certain embodiments, the hydrophilic agent comprises a pH-dependent polymer, non-limiting examples of which include: Cellulose Acetate Phthalate (e.g. Aquacoat® CPD); Cellulose Acetate Trimellitate, Poly(methacrylic acid, ethyl acrylate) 1:1 (e.g. Eudragit® L30D-55); Kollicoat® MAE 30 D; Poly(methacrylic acid, ethyl acrylate) 1:1 (e.g. Eudragit® L100-55); Kollicoat® MAE 30 DP; Eudragit® FS 30D; Hypromellose Acetate Succinate LF, MF, HF grades (e.g. AQOAT®), Polyvinyl Acetate Phthalate, and mixtures thereof. If hydrophilic agents are to be included in the coat composition the agents might be present in certain embodiments in an amount from about 0.1% to about 10% by weight of the coating composition. In other embodiments from about 0.1% to about 5% by weight of the coating composition, and in still other embodiments from about 0.1% to about 3% by weight of the coating composition. In certain embodiments the hydrophilic agent is present in an amount of from greater than about 0% to about 35% by dry weight of the coat. In other embodiments the hydrophilic agent is present in an amount from about 8% to about 30% by dry weight of the coat. In still other embodiments the hydrophilic agent is present in an amount from about 12% to about 26% by dry weight of the coat, for example, about 13%, about 14%, about 15%, about 16%, about 17%, about 18%, about 19%, about 20%, about 21%, about 22%, about 23%, about 24%, and about 25% by dry weight of the coat. In certain embodiments the hydrophilic agent is present in the coating formulation in an amount of from about 0% to about 14.0% by dry weight of the tablet; in other embodiments in an amount of from about 0.2% to about 6.0% by dry weight of the tablet; and in still other embodiments in an amount of from about 0.8% to about 2.5% by dry weight of the tablet; for example, about 0.9%, about 1.0%, about 1.1%, about 1.2%, about 1.3%, about 1.4%, about 1.5%, about 1.6%, about 1.7%, about 1.8%, about 1.9%, about 2.0%, about 2.1%, about 2.2%, about 2.3%, and about 2.4% by dry weight of the tablet.

The tackiness of polymeric films is important for the coating of solid dosage forms and for the subsequent curing step (post coating thermal treatment). During coating with either cellulosic or acrylic polymers, an unwanted, and sometimes irreversible agglomeration of several granules or beads or, in the worst case, of the complete batch, might occur, especially at higher product processing temperatures. Accordingly, the addition of anti-tacking agents to coating formulations is desirable. The anti-tacking agents which can be used include but are not limited to adipic acid, magnesium stearate, calcium stearate, zinc stearate, hydrogenated vegetable oils, sterotex, glyceryl monostearate, talc (e.g. Talc 400), sodium benzoate, sodium lauryl sulfate, magnesium lauryl sulfate, and mixtures thereof. In at least one embodiment talc (e.g. Talc 400) is used as the anti-tacking agent. Talc can also function as a wetting agent. Mixtures of the anti-tacking agents are operable. The amount of anti-tacking agent in the coating composition of certain embodiments can be in the range of from about 1% to about 15% by weight of the coating dispersion, and in certain embodiments from about 1% to about 7% by weight of the coating dispersion. In certain embodiments the anti-tacking agent is present in an amount of from greater than about 0% to about 50% by dry weight of the coat. In other embodiments the anti-tacking agent is present in an amount from about 2% to about 40% by dry weight of the coat. In still other embodiments the anti-tacking agent is present in an amount from about 10% to about 30% by dry weight of the coat; for example, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, and about 29% by dry weight of the coat. In certain embodiments the anti-tacking agent is present in the coating formulation in an amount of from about 0% to about 20.0% by dry weight of the tablet; in other embodiments in an amount of from about 0% to about 12.0% by dry weight of the tablet; and in still other embodiments in an amount of from about 0.6% to about 7.0% by dry weight of the tablet; for example, about 0.7%, about 0.8%, about 0.9%, about 1.0%, about 1.1%, about 1.2%, about 1.3%, about 1.4%, about 1.5%, about 1.6%, about 1.7%, about 1.8%, about 1.9%, about 2.0%, about 2.1%, about 2.2%, about 2.3%, about 2.4%, about 2.5%, about 2.6%, about 2.7%, about 2.8%, about 2.9%, about 3.0%, about 3.1%, about 3.2%, about 3.3%, about 3.4%, about 3.5%, about 3.6%, about 3.7%, about 3.8%, about 3.9%, about 4.0%, about 4.1%, about 4.2%, about 4.3%, about 4.4%, about 4.5%, about 4.6%, about 4.7%, about 4.8%, about 4.9%, about 5.0%, about 5.1%, about 5.2%, about 5.3%, about 5.4%, about 5.5%, about 5.6%, about 5.7%, about 5.8%, about 5.9%, about 6.0%, about 6.1%, about 6.2%, about 6.3%, about 6.4%, about 6.5%, about 6.6%, about 6.7%, about 6.8%, and about 6.9% by dry weight of the tablet.

The anti-foaming agents, which might be included in the coating composition include silicon oil, simethicone (e.g. simethicone emulsion), and mixtures thereof. In at least one embodiment the anti-foaming agent is simethicone. The anti-foaming agent, if present, might be present in certain embodiments in an amount of up to about 0.5% by weight of the coat composition, and in certain other embodiments from about 0.1% to about 0.4% by weight of the coating composition. In certain embodiments the anti-foaming agent is present in an amount of from greater than about 0% to about 3% by dry weight of the coat. In other embodiments the anti-foaming agent is present in an amount from about 0.4% to about 2% by dry weight of the coat. In still other embodiments the anti-foaming agent is present in an amount from about 0.8% to about 1.5% by dry weight of the coat; for example, about 0.9%, about 1.0%, about 1.1%, about 1.2%, about 1.3%, and about 1.4% by dry weight of the coat. In certain embodiments the anti-foaming agent is present in the coating formulation in an amount of from about 0% to about 1.2% by dry weight of the tablet; in other embodiments in an amount of from about 0% to about 0.8% by dry weight of the tablet; and in still other embodiments in an amount of from about 0% to about 0.2% by dry weight of the tablet; for example, about 0.01%, about 0.02%, about 0.03%, about 0.04%, about 0.05%, about 0.06%, about 0.07%, about 0.08%, about 0.09%, about 0.10%, about 0.11%, about 0.12%, about 0.13%, about 0.14%, about 0.15%, about 0.16%, about 0.17%, about 0.18%, and about 0.19% by dry weight of the tablet.

The inclusion of an emulsifying agent (also called emulsifiers or emulgents) might be used to facilitate actual emulsification during manufacture of the coat, and also to provide emulsion stability during the shelf-life of the product. Emulsifying agents useful for the coat composition include, but are not limited to naturally occurring materials and their semi synthetic derivatives, such as the polysaccharides, as well as glycerol esters, cellulose ethers, sorbitan esters and polysorbates. Mixtures are operable. In at least one embodiment the emulsifying agent used is Polysorbate 80 (polyoxyethylene sorbitan mono-oleate), (e.g. Tween® 80). The emulsifying agent or agents, if present, might be present in certain embodiments in an amount of from greater than 0% to about 0.5% by weight of the coat composition. In at least one embodiment the emulsifying agent is present in an amount of from about 0.1% to about 0.3% by weight of the coat composition. In certain embodiments the emulsifying agent is present in an amount of from greater than about 0% to about 2% by dry weight of the coat. In other embodiments the emulsifying agent is present in an amount from about 0.1% to about 1% by dry weight of the coat. In still other embodiments the emulsifying agent is present in an amount from about 0.25% to about 0.75% by dry weight of the coat; for example, including about 0.30%, about 0.35%, about 0.40%, about 0.45%, about 0.50%, about 0.55%, about 0.60%, about 0.65%, and about 0.70% by dry weight of the coat. In certain embodiments the emulsifying agent is present in the coating formulation in an amount of from greater than about 0% to about 0.8% by dry weight of the tablet; in other embodiments in an amount of from greater than about 0% to about 0.4% by dry weight of the tablet; and in still other embodiments in an amount of from greater than about 0% to about 0.2% by dry weight of the tablet; for example, about 0.01%, about 0.02%, about 0.03%, about 0.04%, about 0.05%, about 0.06%, about 0.07%, about 0.08%, about 0.09%, about 0.10%, about 0.11%, about 0.12%, about 0.13%, about 0.14%, about 0.15%, about 0.16%, about 0.17%, about 0.18%, and about 0.19% by dry weight of the tablet.

Any permitted colorants in a film coat formula are invariably water-insoluble colors (pigments). Pigments have certain advantages over water-soluble colors in that they tend to be more chemically stable towards light, provide better opacity and covering power, and optimize the impermeability of a given film to water vapor. Examples of suitable colorants include, but are not limited to iron oxide pigments, titanium dioxide, and aluminum Lakes. Mixtures are operable. In at least one embodiment the pigment or colorant used is titanium dioxide. The pigment or colorant, if present, might be present in certain embodiments in an amount of from about 0.1% to about 10% by weight of the coat composition. In at least one embodiment the colorant is present in an amount of from about 0.1% to about 5% by weight of the coat composition. In at least one other embodiment the colorant is present in an amount of from about 0.1% to about 2% by weight of the coat composition. In certain embodiments the colorant is present in an amount of from greater than about 0% to about 20% by dry weight of the coat. In other embodiments the colorant is present in an amount from greater than about 0% to about 10% by dry weight of the coat. In still other embodiments the colorant is present in an amount from about 2.2% to about 6.2% by dry weight of the coat; for example, including about 2.3%, about 2.4%, about 2.5%, about 2.6%, about 2.7%, about 2.8%, about 2.9%, about 3.0%, about 3.1%, about 3.2%, about 3.3%, about 3.4%, about 3.5%, about 3.6%, about 3.7%, about 3.8%, about 3.9%, about 4.0%, about 4.1%, about 4.2%, about 4.3%, about 4.4%, about 4.5%, about 4.6%, about 4.7%, about 4.8%, about 4.9%, about 5.0%, about 5.1%, about 5.2%, about 5.3%, about 5.4%, about 5.5%, about 5.6%, about 5.7%, about 5.8%, about 5.9%, about 6.0%, and about 6.1% by dry weight of the coat. In certain embodiments the colorant is present in the coating formulation in an amount of from greater than about 0% to about 8.0% by dry weight of the tablet; in other embodiments in an amount of from greater than about 0% to about 5.0% by dry weight of the tablet; and in still other embodiments in an amount of from greater than about 0% to about 1.0% by dry weight of the tablet; for example, including about 0.1%, about 0.2%, about 0.3%, about 0.4%, about 0.5%, about 0.6%, about 0.7%, about 0.8%, and about 0.9% by dry weight of the tablet.

In at least one embodiment the second pharmaceutically acceptable excipients in the controlled-release coating comprises at least one of a neutral ester copolymer without any functional groups (e.g. Eudragit® NE30D, Eudragit® NE40D, Eudragit® NM30D, Kollicoat® EMM30D, or a mixture thereof), HPMC (e.g. Pharmacoat®606), talc (e.g. Talc 400), polyethylene glycol (e.g. polyethylene glycol 4000, polyethylene glycol 4600, polyethylene glycol 6000, polyethylene glycol 8000, polyethylene glycol 10000, polyethylene glycol 12000, polyethylene glycol 20000, polyethylene glycol 35000, or a mixture thereof), simethicone, polysorbate 80, titanium dioxide, and mixtures thereof.

In at least one embodiment, the stable controlled-release coating hydrates when placed into water. In at least one embodiment the dosage form that is coated with the controlled-release coating floats in water. In at least one embodiment, the controlled-release dosage form, upon oral administration to a patient, provides controlled-release of an effective amount of the active drug to at least one region of the patient's upper gastrointestinal tract (e.g. the stomach).

In some embodiments, the controlled-release coating is formed by a process that does not involve the use of an organic solvent. In such embodiments the controlled-release coating composition is aqueous based and not solvent based (termed "AQ" in certain examples of dosage forms coated with the aqueous based controlled-release coating). In some embodiments, the controlled-release coating is formed by a process that are solvent based (e.g. "PharmaPASS™" composition).

The coating composition can be applied onto a core comprising an effective amount of the therapeutically active agent by a process, which involves the atomization (spraying) of the coating composition (solution or suspension) onto a bed of the tablet cores. Some examples of equipment suitable for film coating include: ACCELA COTA® (Manesty Machines, Liverpool, UK), HI-COATER® (Freund Company, Japan), DRIACOATER™ (Driam Metallprodukt GmbH, Germany), HTF/150™ (GS, Italy), and IDA™ (Dumoulin, France). Examples of units that function on a fluidized-bed principle include: AEROMATIC™

(Fielder, Switzerland and UK) and GLATT AG™ (Switzerland). In at least one embodiment the apparatus used is the ACCELA COTA®.

The coating composition is delivered to the coating apparatus from a peristaltic pump at the desired rate and sprayed onto the rotating or fluidizing tablet cores. The tablet cores are pre-warmed to about 30° C. During the coating process, the product temperature range is maintained between about 25° C. and about 35° C. by adjusting the flow rate of the inlet and outlet air, temperature of the inlet air and spray rate. A single layer of the coating composition is applied and once spraying is complete, the coated tablet cores are dried between about 30° C. to about 40° C. for about 3 to about 5 minutes at a low pan speed and low air flow. The pan is readjusted to jog speed, and drying continued for about 12 to about 15 minutes.

The coated tablet cores are placed onto a tray and cured (post coating thermal treatment) in an electrical or steam oven at a temperature above the temperature of the melting point of the polyethylene glycol or derivative thereof. In at least one embodiment the curing temperature is greater than the melting point of the polyethylene glycol or derivative thereof. In at least one embodiment the curing time is from about 2 to about 7 hours. The cured coated tablets are subsequently cooled to about room temperature.

In certain other embodiments, the coated tablet cores are placed onto a coating pan and cured at two-stages. During the first stage, the coated tablets are cured at a first curing temperature (for example, in certain embodiments from between about 50° C. to about 59° C.) for a period of time (for example, in certain embodiments from about 15 minutes to about 90 minutes; and in at least one embodiment for about 60 minutes). During the second stage, the coated tablets are cured at a second curing temperature that is at least equal to or greater than the melting point of the poly glycol (for example, in certain embodiments from between about 60° C. to about 70° C.) for an additional period of time (for example, in certain embodiments from about 30 minutes to about 180 minutes; and in at least one embodiment for about 120 minutes). In at least one embodiment the two-stage curing of the coated tablets reduces non-functional defects on the tablet caused by the curing process. In at least one embodiment the two-stage curing process substantially eliminates non-functional defects on the tablet caused by the curing process. Non-functional defects on the dosage form caused by the curing process can include visual defects in the coating (e.g. poor color uniformity, and/or dull appearance), defects in the surface of the coating (e.g. roughness in the surface of the coating, and/or wrinkles in the coating), and sticking of the tablets to each other and/or to the coating pan. In addition, the reduced defects in color and smoothness of the tablets allows for improved printing of the tablets In some embodiments, the coating formulation is used to coat a variety of iniparib cores and might be adjusted to obtain a desired drug release profile. The length and time for the delay is controlled by rate of hydration and the thickness of the coat. The drug release rate subsequent to the delay is determined by the thickness and permeability of the hydrated coat. Thus, it is possible to regulate the rate of hydration and permeability of the coat so that the desired controlled-release drug profile might be achieved. There is no preferred coat thickness, as this will depend on the drug being used in the core and also the controlled-release profile desired. Other parameters in combination with the thickness of the coat include varying the concentrations of some of the ingredients of the stable coat composition and/or varying the curing temperature and length of curing the coated tablet cores. The skilled artisan will know which parameters or combination of parameters to change for a desired controlled-release profile.

Immediate-Release Coating Formulations

The immediate-release active agent reduces, abates or eliminates adverse side effects associated with administration of iniparib. In some embodiments, the immediate-release agent is antihistamine or antiemetic. In some embodiments, the immediate-release agent is a stimulant. In some embodiments, a portion of the antiemetic or antihistamine ingredient is formulated in immediate-release form.

In some embodiments, an effective amount of the immediate-release active agent in immediate-release form is coated onto the formulations described herein. For example, where the extended release of iniparib from the formulation is due to a controlled-release coating, the immediate-release layer of antihistamine or antiemetic would be overcoated on top of the controlled-release coating. In some embodiments, the immediate-release layer of antihistamine or antiemetic is coated onto the surface of substrates wherein the iniparib is incorporated in a controlled-release matrix. Where a plurality of the sustained release substrates comprising an effective unit dose of the iniparib (e.g., multiparticulate systems including pellets, spheres, beads and the like) are incorporated into a hard gelatin capsule, the side-effect-reducing compound might be incorporated into the gelatin capsule via inclusion of the sufficient amount of immediate-release antihistamine or antiemetic as a powder or granulate within the capsule. Alternatively, the gelatin capsule itself might be coated with an immediate-release layer of antihistamine or antiemetic. One skilled in the art would recognize still other alternative manners of incorporating the immediate-release side-effect-reducing compound into the unit dose. Such alternatives are deemed to be encompassed by the current claims. By including such an effective amount of immediate-release side-effect-reducing compound such as antihistamine or antiemetic in the unit dose, the experience of side effects including nausea, vomiting, and skin rashes in patients might be significantly reduced.

A coating containing the immediate-release of side-effect-reducing compounds such as antihistamine or antiemetic might be added to the outside of the controlled-release tablet cores to produce a final dosage form. Such a coating might be prepared by mixing compounds like promethazine with polyvinylpyrrolidone 29/32 (PVP 29/32) or hydroxypropyl methylcellulose (HPMC) and water/isopropyl alcohol and triethyl acetate. Such an immediate-release coating might be spray coated onto the tablet cores. The immediate-release coating might also be applied using a press-coating process with a blend consisting of 80% by weight of promethazine and 20% by weight of lactose and hydroxypropyl methylcellulose type 2910 (Hypromellose, Substitution Type 2910).

In some embodiments, the immediate-release/controlled-release dosage forms described herein form bi-layered tablets, which comprise a first layer and a second layer. In some embodiments of the bi-layered tablet, the first layer is an immediate-release layer and/or the second layer is a controlled-release layer. The first top layer comprises a first drug which is selected from analgesics, antitussives, antihistamines, antiemetics, and stimulants. The second layer comprises a second drug. In some embodiments, the second drug is iniparib. In some embodiments, the second drug is a formulation of iniparib described herein. The bi-layered tablet provides a plasma concentration within the therapeutic range of the second drug over a period which is coextensive with at least about 70% of the period (i.e. 12 hours) within which the bi-layered tablet provides a plasma concentration within the therapeutic range of the first drug.

In some embodiments, the first immediate-release layer comprises a stimulant. In some embodiments, the stimulant is selected from the group consisting of aminophylline, caffeine, dyphlline, oxitriphylline, theophhylline, amphetamine, benzphetamine, dextroamphetamine, diethylpropion, mazindol, methamphetamine, methylphenidate, dexmethylphenidate, pemoline, sibutramine, modafinil, atomoxetine, phendimetrizine, phenteramine, adrafinil, phenylpropanolamine, psuedoephedrine, synephrine, amphetaminil, furfenorex, or a combination thereof.

In some embodiments, the first immediate-release layer comprises an antiemetic. In some embodiments, the antiemetic is selected from the group consisting of aprepitant, dronabinol, perphenazine, palonosetron, trimethobenzamide, metoclopromide, domperidone, prochlorperazine, promethazine, chlorpromazine, trimethobenzamide, ondansetron, granisetron, hydroxyzine, acetylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxyperndyl, pipamazine, scopolamine, sulpiride, tetrahydrocannabinol, thiethylperazine, thioproperazine, tropisetron, droperidol, haloperidol, prochloperazine, metoclopramide, diphenhydramine, *cannabis*, midazolam, lorazepam, hyoscine, dexamethasone, emetrol, propofol, or a combination thereof.

In some embodiments, the first immediate-release layer comprises an antihistamine. In some embodiments, the antihistamine is selected from the group consisting of 2-(m-fluorophenyl)-histamine, chlorpheniramine, mepyramine, terfenadine, astemizole, triprolidine, ethanolamines carbinoxamine, diphenhydramine, doxylamine, pyrilamine, tripelennamine, hydroxyzine, fexofenadine, brompheniramine chlorpheniramine, cyproheptadine, loratadine, cetirizine, dimaprit, impromidine, amthamine, cimetidine, ranitidine, nizatidine, famotidine, R-alpha-methylhistamine, imetit, immepip, thioperamide, iodophenpropit, clobenpropit, clobenpropit, imetit, clozapine, thioperamide, azelastine, brompheniramine, carbinoxamine, cetrizine, chlorpheniramine, clemastine, cyclizine, cyproheptadine, desloratidine, dimenhydrinate, diphenhydramine, emedastine, fexofenadine, ketotifen, levocabastine, loratadine, meclizine, olopatadine, phenindamine, promethazine, or a combination thereof.

Controlled-Release Matrix Formulations

In another aspect, described herein is a controlled-release iniparib formulation comprising a controlled-release matrix and from about 30 mg to about 400 mg of iniparib or a pharmaceutically acceptable salt, solvate, or prodrug thereof, wherein a median particle size of iniparib or a pharmaceutically acceptable salt, solvate, metabolite, or prodrug thereof is from about 20 µm to about 400 µm; and wherein the formulation provides a maximum mean blood concentration of iniparib of between about 200 ng/ml and about 6000 ng/ml upon oral administration to a subject in need thereof.

In some embodiments, the controlled-release iniparib formulation comprises from about 30 mg to about 400 mg of iniparib or a pharmaceutically acceptable salt, solvate, or prodrug thereof. In some embodiments, the controlled-release iniparib formulation comprises about 30 mg, about 33.3 mg, about 40 mg, about 50 mg, about 60 mg, about 66.6 mg, about 70 mg, about 80 mg, about 90 mg, about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, about 300 mg, about 310 mg, about 320 mg, about 330 mg, about 340 mg, about 350 mg, about 360 mg, about 370 mg, about 380 mg, about 390 mg, or about 400 mg of iniparib or a pharmaceutically acceptable salt, solvate, or prodrug thereof.

In some embodiments, the controlled-release iniparib formulation provides a maximum mean blood concentration of iniparib of between about 200 ng/ml and about 6000 ng/ml upon oral administration to a subject in need thereof. In some embodiments, the controlled-release iniparib formulation provides a maximum mean blood concentration of iniparib of about 200 ng/ml, about 210 ng/ml, about 220 ng/ml, about 230 ng/ml, about 240 ng/ml, about 250 ng/ml, about 260 ng/ml, about 270 ng/ml, about 280 ng/ml, about 290 ng/ml, about 300 ng/ml, about 310 ng/ml, about 320 ng/ml, about 330 ng/ml, about 340 ng/ml, about 350 ng/ml, about 360 ng/ml, about 370 ng/ml, about 380 ng/ml, about 390 ng/ml, about 400 ng/ml, about 410 ng/ml, about 420 ng/ml, about 430 ng/ml, about 440 ng/ml, about 450 ng/ml, about 460 ng/ml, about 470 ng/ml, about 480 ng/ml, about 490 ng/ml, about 500 ng/ml, about 510 ng/ml, about 520 ng/ml, about 530 ng/ml, about 540 ng/ml, about 550 ng/ml, about 560 ng/ml, about 570 ng/ml, about 580 ng/ml, about 590 ng/ml, about 600 ng/ml, about 610 ng/ml, about 620 ng/ml, about 630 ng/ml, about 640 ng/ml, about 650 ng/ml, about 660 ng/ml, about 670 ng/ml, about 680 ng/ml, about 690 ng/ml, about 700 ng/ml, about 710 ng/ml, about 720 ng/ml, about 730 ng/ml, about 740 ng/ml, about 750 ng/ml, about 760 ng/ml, about 770 ng/ml, about 780 ng/ml, about 790 ng/ml, about 800 ng/ml, about 810 ng/ml, about 820 ng/ml, about 830 ng/ml, about 840 ng/ml, about 850 ng/ml, about 860 ng/ml, about 870 ng/ml, about 880 ng/ml, about 890 ng/ml, about 900 ng/ml, about 910 ng/ml, about 920 ng/ml, about 930 ng/ml, about 940 ng/ml, about 950 ng/ml, about 960 ng/ml, about 970 ng/ml, about 980 ng/ml, about 990 ng/ml, about 1000 ng/ml, about 1100 ng/ml, about 1200 ng/ml, about 1300 ng/ml, about 1400 ng/ml, about 1500 ng/ml, about 1600 ng/ml, about 1700 ng/ml, about 1800 ng/ml, about 1900 ng/ml, about 2000 ng/ml, about 2100 ng/ml, about 2200 ng/ml, about 2300 ng/ml, about 2400 ng/ml, about 2500 ng/ml, about 2600 ng/ml, about 2700 ng/ml, about 2800 ng/ml, about 2900 ng/ml, about 3000 ng/ml, about 3100 ng/ml, about 3200 ng/ml, about 3300 ng/ml, about 3400 ng/ml, about 3500 ng/ml, about 3600 ng/ml, about 3700 ng/ml, about 3800 ng/ml, about 3900 ng/ml, about 4000 ng/ml, about 4100 ng/ml, about 4200 ng/ml, about 4300 ng/ml, about 4400 ng/ml, about 4500 ng/ml, about 4600 ng/ml, about 4700 ng/ml, about 4800 ng/ml, about 4900 ng/ml, about 5000 ng/ml, about 5100 ng/ml, about 5200 ng/ml, about 5300 ng/ml, about 5400 ng/ml, about 5500 ng/ml, about 5600 ng/ml, about 5700 ng/ml, about 5800 ng/ml, about 5900 ng/ml, or about 6000 ng/ml, upon oral administration to a subject in need thereof.

In some embodiments, the controlled-release iniparib formulation provides a maximum mean blood concentration of 4-iodo-3-aminobenzoic acid of between about 4 ng/ml and about 60 ng/ml upon oral administration to a subject in need thereof. In some embodiments, the maximum mean blood concentration of 4-iodo-3-aminobenzoic acid is about 4 ng/ml, about 5 ng/ml, about 6 ng/ml, about 7 ng/ml, about 8 ng/ml, about 9 ng/ml, about 10 ng/ml, about 11 ng/ml, about 12 ng/ml, about 13 ng/ml, about 14 ng/ml, about 15 ng/ml, about 16 ng/ml, about 17 ng/ml, about 18 ng/ml, about 19 ng/ml, about 20 ng/ml, about 21 ng/ml, about 22 ng/ml, about 23 ng/ml, about 24 ng/ml, about 25 ng/ml, about 26 ng/ml, about 27 ng/ml, about 28 ng/ml, about 29 ng/ml, about 30 ng/ml, about 31 ng/ml, about 32 ng/ml, about 33 ng/ml, about 34 ng/ml, about 35 ng/ml, about 36 ng/ml, about 37 ng/ml, about 38 ng/ml, about 39 ng/ml, about 40 ng/ml, about 41 ng/ml, about 42 ng/ml, about 43 ng/ml, about 44 ng/ml, about 45 ng/ml, about 46 ng/ml, about 47 ng/ml, about 48 ng/ml, about 49 ng/ml, about 50 ng/ml, about 51 ng/ml, about 52 ng/ml, about 53 ng/ml, about 54 ng/ml, about 55 ng/ml, about 56 ng/ml, about 57 ng/ml, about 58 ng/ml, about 59 ng/ml, or about 60 ng/ml, upon oral administration to a subject in need thereof.

In some embodiments, the controlled-release iniparib formulation provides a maximum mean blood concentration of 4-iodo-3-aminobenzamide of between about 1 ng/ml and about 15 ng/ml upon oral administration to a subject in need thereof. In some embodiments, the maximum mean blood concentration of 4-iodo-3-aminobenzamide is about 1 ng/ml, about 2 ng/ml, about 3 ng/ml, about 4 ng/ml, about 5 ng/ml, about 6 ng/ml, about 7 ng/ml, about 8 ng/ml, about 9 ng/ml, about 10 ng/ml, about 11 ng/ml, about 12 ng/ml, about 13 ng/ml, about 14 ng/ml, or about 15 ng/ml, upon oral administration to a subject in need thereof.

In some embodiments, the controlled-release iniparib formulation comprises at least about 30 mg of iniparib and wherein said formulation is repeatedly administered to a subject in need thereof about every 8 hours, about every 12 hours, about every 24 hours, about every other day, about twice a week, about once a week, about once every two weeks, or about once a month.

In some embodiments, the controlled-release iniparib formulation comprises at least about 100 mg of iniparib and wherein said formulation is repeatedly administered to a subject in need thereof about every 8 hours, about every 12 hours, about every 24 hours, about every other day, about twice a week, about once a week, about once every two weeks, or about once a month.

In some embodiments, the controlled-release iniparib formulation comprises at least about 200 mg of iniparib and wherein said formulation is repeatedly administered to a subject in need thereof about every 8 hours, about every 12 hours, about every 24 hours, about every other day, about twice a week, about once a week, about once every two weeks, or about once a month.

In some embodiments, the controlled-release iniparib formulation comprises at least about 400 mg of iniparib and wherein said formulation is repeatedly administered to a subject in need thereof about every 8 hours, about every 12 hours, about every 24 hours, about every other day, about twice a week, about once a week, about once every two weeks, or about once a month.

In some embodiments, multiple doses of the controlled-release iniparib formulation are administered to a subject in need thereof to provide a maximum mean blood concentration of iniparib of between about 200 ng/ml and about 6000 ng/ml upon oral administration to the subject in need thereof.

In some embodiments, the number of doses of the controlled-release iniparib formulation to be administered to a subject in need thereof is at least 1, 2, 3, 4, 5, 6, 7, 8, 9, or 10 doses in order to provide a maximum mean blood concentration of iniparib of between about 200 ng/ml and about 6000 ng/ml upon oral administration.

Controlled-Release Matrix

There are many mechanisms by which a bioactive agent might be released from a controlled-release matrix. Two mechanisms include diffusion and/or degradation. Diffusion occurs when the bioactive agent is released either through pores in the polymer matrix or by passing between polymer chains of the matrix. In a diffusion system, the bioactive agent might be dispersed throughout the matrix, or localized within a reservoir adjacent to or within the matrix. In a reservoir system, a reservoir of bioactive agent, for example, solid drug, dilute solution, or highly concentrated drug solution within a polymer matrix is surrounded by a controlled-release material through which the bioactive agent is able to diffuse. In a degradable system, the bioactive agent is released as the matrix is degraded in vivo. Bioactive agent might also be released by a combination of the two mechanisms. In some embodiment of the controlled-release matrix described herein, the release of the bioactive agent is driven by a combination of both diffusion and degradation. The release rate might be controlled by varying the drug to polymer ratio (e.g., a higher drug concentration tends to result in a faster rate of release), by varying the chemistry of polymeric matrix (e.g., inclusion of polymers having a Tg of less than about 40° C. or less than about 0° C. would tend to result in a faster elution rate than polymers with Tgs greater than 40° C., polymers that absorb water tend to elute drug more quickly than more hydrophobic polymers that do not absorb water. These variables might be controlled by the selection of materials used in the manufacturing process.

In some embodiments, the controlled-release matrix is configured to release at least about 40% and up to about 60%, or at least 50% of the bioactive agent within 24 hours of administration. In another embodiment, the controlled-release matrix is configured to release at least about 80% or up to about 100%, or at least 90% of the bioactive agent within 7 days after administration.

In some embodiments, the controlled-release matrix is biodegradable. In some embodiments, the controlled-release matrix includes a biodegradable polyester. Examples of biodegradable polyesters include, but are not limited to: polycaprolactone (PCL), polylactic acid (PLA), polyglycolide (PGA), and copolymers thereof, such as poly(lactic-co-glycolic acid) polymers (PLGA) and poly(glycolide-co-caprolactone) (PGC). Polycaprolactone (PCL) refers to a biodegradable polyester prepared by ring opening polymerization of ε-caprolactone using a catalyst such as stannous octanoate. Polycaprolactone has a melting point of about 60° C. and is degraded by hydrolysis of its ester linkages under physiological conditions.

Polylactic acid (PLA) is a biodegradable, thermoplastic polyester that can be produced by bacterial fermentation of renewable resources such as corn, starch or sugarcane and has a melting temperature between about 173° C. and about 178° C.

Polyglycolide (PGA) is a biodegradable, thermoplastic polyester prepared from glycolic acid by polycondensation or ring-opening polymerization. It has a melting point of between about 225° C. to about 230° C.

Poly(lactic-co-glycolic acid) polymers (PLGA) refers to a biodegradable copolymer of lactic and glycolic acid formed by random ring-opening co-polymerization of monomers of glycolic acid and lactic acid. During polymerization, the monomeric units are linked together by ester linkages, thus yielding an aliphatic polyester. PLGAs are amorphous and have a glass transition temperature between about 40° C. and 60° C. In general, the PLGA copolymer has a weight average molecular weight between about 1000 Da to about 50,000 Da, or between about 5000 Da and 25,000 Da. The ratio of lactic acid to glycolic acid might vary. In general and increase in the amount of lactic acid results in a polymer that degrades more slowly. An increase in glycolic acid results in a polymer that degrades more quickly. Additionally, an increase in glycolic acid tends to decrease the glass transition temperature (Tg) and water penetration into the polymer, which can result in a faster release of compounds. In general, the ratio of lactic acid to glycolic acid is between about 100:0 to about 25:75, or between about 60:40 and 40:60, or about 50:50.

Other suitable biodegradable polymers include, but are not limited to, poly(trimethylene carbonate) (PTMC), polydioxanone (PDO), poly(4-hydroxy butyrate) (PHB), and poly(butylene succinate) (PBS), poly(trimethylene carbonate) (PTMC), polydioxanone (PDO), poly(4-hydroxy butyrate) (PHB), and poly(butylene succinate) (PBS).

In some embodiments, the polymeric material or polymer is biostable. Examples of biostable polymers include, but are not limited to polyurethanes, silicone rubbers, styrene-isobutylene-styrene block copolymers, ether-ester block copolymers (e.g., 1500-40D from RTP Co.) and vinyl materials, including but not limited to poly(ethylene-co-vinyl acetate) (PEVA).

In some embodiments, the controlled-release matrix includes an elastomeric polymeric material that includes a copolymer with an elastomeric (or "soft") component and a non-elastomeric (or "hard") component. In another embodiment, the elastomeric polymeric material includes a polymeric blend having an elastomeric component and a non-elastomeric component.

In some embodiments, the compliant polymer or polymeric material is thermoplastic. As used herein, the term "thermoplastic" refers to a polymer or polymeric material that can be softened by heat, hardened by cooling and then softened by heat over and over again. In general, thermoplastic materials are not cross-linked. However, in another embodiment, the compliant polymer or polymeric material might be cross-linked.

The bioactive agent might be incorporated into the controlled-release matrix any of various techniques known to the skilled artisan. In one embodiment, the bioactive agent is dispersed throughout the controlled-release matrix. Techniques for preparing the controlled-release matrix include, but are not limited to, melt extrusion processes, injection molding, or spray casting.

In a melt extrusion process, a mixture that includes the polymeric material and bioactive agent is combined in an extruder, heated to a temperature at which the polymeric material melts and then discharged through an orifice of the desired cross-sectional shape. The extruded material is collected under controlled conditions (e.g., speed, temperature and humidity) to obtain a product with the desired dimensions. In one embodiment, the mass flow rate of the extrudate and the collection speed of the final extruded form might be controlled to achieve the desired physical dimensions. For example, if the final extruded form is a film, then the collection speed of the film might be increased relative to the mass flow rate of the extrudate to decrease the film thickness, and conversely to increase the film thickness. The extrudate is discharged through an orifice in the molten state, allowing elongation of the extrudate to its final dimension. The extrudate is subsequently cooled by exposure to ambient conditions, a chilled liquid or gas bath, or exposure to a temperature controlled surface such as a cooled roller in order to solidify the extrudate. In one embodiment, the melt extrusion process is used to form a film. In an alternate embodiment, the melt extrusion process is used to form pellets or beads that might be subsequently molded into the desired film or collar configuration. Some of the advantages of melt extrusion processes include: the absence of organic solvents and high throughput, continuous manufacturing. In general, the processing temperature is sufficient to melt the polymeric material without adversely affecting the biological activity of the bioactive agent. In general, the processing temperature is at least about 80° C. or about 100° C., and less than about 180° C., less than 160° C., or between about 110° C. and about 150° C. In some embodiments, the specific temperature is dependent on the melting and degradation temperatures of the polymeric materials and bioactive agent. Furthermore, melt-processing provides the ability for continuous operation, the ability to control operating parameters, and the ability to scale up manufacturing.

In an alternate embodiment, an injection molding process is used. In an injection molding process, a mixture that includes the polymeric material and bioactive agent is fed into a vessel where it heated to a temperature sufficient to melt the polymeric material and then forced into a mold cavity where it cools and hardens to the configuration of the mold cavity. The conditions (e.g., temperature and pressure) will depend upon the material being molded. In one embodiment, the injection molding process is used to form a film or a collar.

In yet another embodiment, a solvent casting technique might be used. In a solvent casting process, the polymeric material and bioactive agent are combined with a suitable solvent to form a polymeric solution which is then cast on a substrate. The solvent is then removed to form a film, for example, by evaporation. In one embodiment, the solvent is removed under a vacuum (e.g., between about 15 in Hg and about 28 in Hg, depending upon the volatility of the solvent). In another embodiment, the solvent is removed at an elevated temperature (e.g., between about 30° C. and about 80° C.). In an alternate embodiment, the polymeric solution is applied to the substrate by a spray coating process. In a spray coating process, the polymeric solution is fed to the spray nozzle, for example and ultrasonic spray nozzle, at a controlled rate by a positive displacement pump. The spray nozzle and substrate are moved in relative motion to each other at controlled speed to achieve the desired coating thickness. The spray nozzle is mounted on a three-axis motion control system (x-y-z) which is capable of controlling the speed and position of the spray head relative to the substrate. In addition, if the substrate is a rolled film, it is traversed below the spray head by a roll to roll unwinding and winding apparatus. The coating width is controlled by moving the spray nozzle in a specified path across the width of the substrate. In addition, the height (z) of the spray nozzle above the substrate might be increased to achieve a wider coating width.

The solvent might be one in which one or more components of the polymeric material form a true solution. The bioactive agent might either be soluble in the solvent or form a dispersion throughout the solvent. Suitable solvents include, but are not limited to, alcohols (e.g., methanol, butanol, propanol and isopropanol), alkanes (e.g., halogenated or unhalogenated alkanes such as hexane, cyclohexane, methylene chloride and chloroform), amides (e.g., dimethylformamide), ethers (e.g., tetrahydrofuran (THF), dioxolane, and dioxane), ketones (e.g., methyl ethyl ketone, acetone), aromatic compounds (e.g., toluene and xylene), nitriles (e.g., acetonitrile) and esters (e.g., ethyl acetate). THF and chloroform have been found to be suitable solvents due to their excellent solvency for a variety of polymers and bioactive agents.

Oral Liquid Formulations

Another way to improve bioavailability of iniparib is to use iniparib or a pharmaceutically acceptable salt, solvate, metabolite, or prodrug thereof in a form of a liquid formulation. In some embodiments, described herein are liquid formulations comprising an iniparib active ingredient for enhanced bioavailability, and efficacy, lower administration dose, lower cytotoxicity, and decreased side effects. In some embodiments, a liquid formulation is used for oral administration. In some embodiments, a liquid formulation is used for transmucosal administration, (e.g. in the form of an aerosol formulation).

In one aspect, described herein is a liquid iniparib formulation comprising:
(i) a pharmaceutically acceptable salt of iniparib or a solvate, metabolite, or prodrug thereof;
(ii) a buffer;
(iii) a surfactant;
(iv) water; and
(v) optionally one or more agents selected from the group consisting of preservatives, flavoring agents, sweetening agents, antifoaming agent, and suspensions aids; wherein said formulation is an oral liquid formulation, and
wherein said formulation is stable at about 5±5° C. to about 25±5° C. for at least 6 months.

In some embodiments, the metabolite of iniparib is selected from the group consisting of: 4-iodo-3-nitrosobenzamide, 3-(hydroxyamino)-4-iodobenzamide, 3-hydroxy-4-iodobenzamide, 4-(methylthio)-3-nitrobenzamide, and N5-(3-((4-carbamoyl-2-nitrophenyl)thio)-1-((carboxymethyl)amino)-1-oxopropan-2-yl)glutamine. In some embodiments, the metabolite of iniparib is 4-iodo-3-nitrosobenzamide. In some embodiments, the metabolite of iniparib is 3-(hydroxyamino)-4-iodobenzamide. In some embodiments, the metabolite of iniparib is 3-hydroxy-4-iodobenzamide. In some embodiments, the metabolite of iniparib is 4-(methylthio)-3-nitrobenzamide. In some embodiments, the metabolite of iniparib is N5-(3-((4-carbamoyl-2-nitrophenyl)thio)-1-((carboxymethyl)amino)-1-oxopropan-2-yl)glutamine.

In some embodiments, the pharmaceutically acceptable salt of iniparib is a salt selected from the group consisting of hydrochloride, hydrobromide, maleate, mesylate, tosylate, fumarate, tartrate, sulfate, and sulfonates. In some embodiments, the pharmaceutically acceptable salt of iniparib is hydrochloride. In some embodiments, the pharmaceutically acceptable salt of iniparib is a hydrobromide salt. In some embodiments, the pharmaceutically acceptable salt of iniparib is a maleate salt. In some embodiments, the pharmaceutically acceptable salt of iniparib is a mesylate salt. In some embodiments, the pharmaceutically acceptable salt of iniparib is a tosylate salt. In some embodiments, the pharmaceutically acceptable salt of iniparib is a fumarate salt. In some embodiments, the pharmaceutically acceptable salt of iniparib is a tartrate salt. In some embodiments, the pharmaceutically acceptable salt of iniparib is a sulfate salt. In some embodiments, the pharmaceutically acceptable salt of iniparib is a sulfonate salt.

In some embodiments, the molar ratio of iniparib moiety to anion is within the range from about 0.5:1 to about 1.5:1. In some embodiments, the molar ratio of iniparib moiety to anion is about 0.5:1, about 0.6:1, about 0.7:1, about 0.8:1, about 0.9:1, about 1:1, about 1.1:1, about 1.2:1, about 1.3:1, about 1.4:1, or about 1.5:1.

In some embodiments, the pharmaceutically acceptable salt of iniparib is a salt that is substantially free of bound water and organic solvent.

In some embodiments, the pharmaceutically acceptable salt of iniparib is selected from the group consisting of iniparib hydrogentartrate, iniparib hydrochloride, iniparib hydrobromide, iniparib mesylate, iniparib tosylate, and iniparib sulfate. In some embodiments, the pharmaceutically acceptable salt of iniparib is iniparib hydrogentartrate. In some embodiments, the pharmaceutically acceptable salt of iniparib is iniparib hydrochloride. In some embodiments, the pharmaceutically acceptable salt of iniparib is iniparib hydrobromide. In some embodiments, the pharmaceutically acceptable salt of iniparib is iniparib mesylate. In some embodiments, the pharmaceutically acceptable salt of iniparib is iniparib tosylate. In some embodiments, the pharmaceutically acceptable salt of iniparib is iniparib sulfate.

In some embodiments, the pharmaceutically acceptable salt of iniparib is an amorphous salt form. In some embodiments, the pharmaceutically acceptable salt of iniparib is a crystalline salt form.

In some embodiments, the surfactant is sodium lauryl sulfate. In some embodiments, the surfactant is poloxamer 188. In some embodiments, the surfactant is polysorbate 80. In some embodiments, the amount of a surfactant is from about 0.1 mg/mL to about 2 mg/mL. In some embodiments, the amount of the surfactant is about 0.1 mg/mL, about 0.2 mg/mL, about 0.3 mg/mL, about 0.4 mg/mL, about 0.5 mg/mL, about 0.6 mg/mL, about 0.7 mg/mL, 0.8 mg/ml, about 0.9 mg/ml, about 1.0 mg/ml, about 1.1 mg/ml, about 1.2 mg/ml, about 1.3 mg/ml, about 1.4 mg/ml, about 1.5 mg/ml, about 1.6 mg/ml, about 1.7 mg/ml, about 1.8 mg/ml, about 1.9 mg/ml, or about 2.0 mg/ml.

In some embodiments, the oral liquid formulation comprises a preservative. In some embodiments, the preservative is selected from the group consisting of sodium benzoate, a paraben or paraben salt, and combinations thereof.

In some embodiments, the amount of a preservative is from about 0.1 mg/mL to about 2 mg/mL. In some embodiments, the amount of the preservative is about 0.1 mg/mL, about 0.2 mg/mL, about 0.3 mg/mL, about 0.4 mg/mL, about 0.5 mg/mL, about 0.6 mg/mL, about 0.7 mg/mL, 0.8 mg/ml, about 0.9 mg/ml, about 1.0 mg/ml, about 1.1 mg/ml, about 1.2 mg/ml, about 1.3 mg/ml, about 1.4 mg/ml, about 1.5 mg/ml, about 1.6 mg/ml, about 1.7 mg/ml, about 1.8 mg/ml, about 1.9 mg/ml, or about 2.0 mg/ml.

In some embodiments, the buffer comprises an acetate buffer. In some embodiments, the acetate buffer concentration is about 3 mM to about 15 mM.

In some embodiments, the buffer comprises a phosphate buffer. In some embodiments, the phosphate buffer concentration is about 3 mM to about 15 mM.

In some embodiments, the oral liquid formulation comprises an antifoaming agent. In some embodiments, the antifoaming agent is simethicone. In some embodiments, the amount of an antifoaming agent is from about 0.1 mg/mL to about 2 mg/mL. In some embodiments, the amount of the antifoaming agent is about 0.1 mg/mL, about 0.2 mg/mL, about 0.3 mg/mL, about 0.4 mg/mL, about 0.5 mg/mL, about 0.6 mg/mL, about 0.7 mg/mL, 0.8 mg/ml, about 0.9 mg/ml, about 1.0 mg/ml, about 1.1 mg/ml, about 1.2 mg/ml, about 1.3 mg/ml, about 1.4 mg/ml, about 1.5 mg/ml, about 1.6 mg/ml, about 1.7 mg/ml, about 1.8 mg/ml, about 1.9 mg/ml, or about 2.0 mg/ml.

In some embodiments, the oral liquid formulation comprises a suspension aid. In some embodiments, the suspension aid comprises silicon dioxide, hydroxypropyl methylcellulose, methylcellulose, microcrystalline cellulose, polyvinylpyrrolidone, or combinations thereof.

In some embodiments, the suspension aid is silicon dioxide. In some embodiments, the amount of silicon dioxide is from about 0.1 mg/mL to about 5 mg/mL. In some embodiments, the amount of silicon dioxide is about 0.1 mg/mL, about 0.2 mg/mL, about 0.3 mg/mL, about 0.4 mg/mL, about 0.5 mg/mL, about 0.6 mg/mL, about 0.7 mg/mL, 0.8 mg/ml, about 0.9 mg/ml, about 1.0 mg/ml, about 1.1 mg/ml, about 1.2 mg/ml, about 1.3 mg/ml, about 1.4 mg/ml, about 1.5 mg/ml, about 1.6 mg/ml, about 1.7 mg/ml, about 1.8 mg/ml, about 1.9 mg/ml, about 2.0 mg/ml, about 2.1 mg/ml, about 2.2 mg/ml, about 2.3 mg/ml, about 2.4 mg/ml, about 2.5 mg/ml, about 2.6 mg/ml, about 2.7 mg/ml, about 2.8 mg/ml, about 2.9 mg/ml, about 3.0 mg/ml, about 3.1 mg/ml, about 3.2 mg/ml, about 3.3 mg/ml, about 3.4 mg/ml, about 3.5 mg/ml, about 3.6 mg/ml, about 3.7 mg/ml, about 3.8 mg/ml, about 3.9 mg/ml, about 4.0 mg/ml, about 4.1 mg/ml, about 4.2 mg/ml, about 4.3 mg/ml, about 4.4 mg/ml, about 4.5 mg/ml, about 4.6 mg/ml, about 4.7 mg/ml, about 4.8 mg/ml, about 4.9 mg/ml, or about 5.0 mg/ml.

In some embodiments, the suspension aid is hydroxypropyl methylcellulose. In some embodiments, the amount of hydroxypropyl methylcellulose is from about 3 mg/ml to about 10 mg/ml. In some embodiments, the amount of hydroxypropyl methylcellulose is about 3.0 mg/ml, about 3.1 mg/ml, about 3.2 mg/ml, about 3.3 mg/ml, about 3.4 mg/ml, about 3.5 mg/ml, about 3.6 mg/ml, about 3.7 mg/ml, about 3.8 mg/ml, about 3.9 mg/ml, about 4.0 mg/ml, about 4.1 mg/ml, about 4.2 mg/ml, about 4.3 mg/ml, about 4.4 mg/ml, about 4.5 mg/ml, about 4.6 mg/ml, about 4.7 mg/ml, about 4.8 mg/ml, about 4.9 mg/ml, about 5.0 mg/ml, about 5.1 mg/ml, about 5.2 mg/ml, about 5.3 mg/ml, about 5.4 mg/ml, about 5.5 mg/ml, about 5.6 mg/ml, about 5.7 mg/ml, about 5.8 mg/ml, about 5.9 mg/ml, about 6.0 mg/ml, about 6.1 mg/ml, about 6.2 mg/ml, about 6.3 mg/ml, about 6.4 mg/ml, about 6.5 mg/ml, about 6.6 mg/ml, about 6.7 mg/ml, about 6.8 mg/ml, about 6.9 mg/ml, about 7.0 mg/ml, about 7.1 mg/ml, about 7.2 mg/ml, about 7.3 mg/ml, about 7.4 mg/ml, about 7.5 mg/ml, about 7.6 mg/ml, about 7.7 mg/ml, about 7.8 mg/ml, about 7.9 mg/ml, about 8.0 mg/ml, about 8.1 mg/ml, about 8.2 mg/ml, about 8.3 mg/ml, about 8.4 mg/ml, about 8.5 mg/ml, about 8.6 mg/ml, about 8.7 mg/ml, about 8.8 mg/ml, about 8.9 mg/ml, about 9.0 mg/ml, about 9.1 mg/ml, about 9.2 mg/ml, about 9.3 mg/ml, about 9.4 mg/ml, about 9.5 mg/ml, about 9.6 mg/ml, about 9.7 mg/ml, about 9.8 mg/ml, about 9.9 mg/ml, or about 10.0 mg/ml.

In some embodiments, the suspension aid is a combination of polyvinylpyrrolidone and hydroxypropyl methylcellulose. In some embodiments, the amount of polyvinylpyrrolidone is from about 0.5 mg/mL to about 3 mg/mL and the amount of hydroxypropyl methylcellulose is from about 3 mg/mL to about 10 mg/mL.

In some embodiments, the oral liquid formulation comprises a flavoring agent.

In some embodiments, the oral liquid formulation comprises a sweetener. In some embodiments, the sweetener is sucralose or xylitol.

In some embodiments, the oral liquid formulation is in the form of a suspension.

In some embodiments, the pH of the oral liquid formulation is between about 4 and about 8. In some embodiments, the pH of the oral liquid formulation is about 4, about 4.1, about 4.2, about 4.3, about 4.4, about 4.5, about 4.6, about 4.7, about 4.8, about 4.9, about 5, about 5.1, about 5.2, about 5.3, about 5.4, about 5.5, about 5.6, about 5.7, about 5.8, about 5.9, about 6, about 6.1, about 6.2, about 6.3, about 6.4, about 6.5, about 6.6, about 6.7, about 6.8, about 6.9, about 7, about 7.1, about 7.2, about 7.3, about 7.4, about 7.5, about 7.6, about 7.7, about 7.8, about 7.9, or about 8.

In some embodiments, the amount of the pharmaceutically acceptable salt of iniparib corresponds to from about 0.5 mg/mL to about 20 mg/mL of iniparib as a free base.

In some embodiments, the oral liquid formulation is stable at about 5±5° C. to about 25±5° C. for at least 2 months. In some embodiments, the oral liquid formulation is stable at about 5±5° C. to about 25±5° C. for at least 4 months. In some embodiments, the oral liquid formulation is stable at about 5±5° C. to about 25±5° C. for at least 6 months. In some embodiments, the oral liquid formulation is stable at about 5±5° C. to about 25±5° C. for at least 9 months. In some embodiments, the oral liquid formulation is stable at about 5±5° C. to about 25±5° C. for at least 12 months. In some embodiments, the oral liquid formulation is stable at about 5±5° C. to about 25±5° C. for at least 15 months. In some embodiments, the oral liquid formulation is stable at about 5±5° C. to about 25±5° C. for at least 18 months. In some embodiments, the oral liquid formulation is stable at about 5±5° C. to about 25±5° C. for at least 24 months. In some embodiments, the oral liquid formulation is stable at about 5±5° C. to about 25±5° C. for at least 30 months. In some embodiments, the oral liquid formulation is stable at about 5±5° C. to about 25±5° C. for at least 36 months.

Buffers for the Iniparib Liquid Formulations

Buffering agents maintain the pH of the liquid iniparib formulation. Non-limiting examples of buffering agents include, but are not limited to sodium bicarbonate, potassium bicarbonate, magnesium hydroxide, magnesium lactate, magnesium gluconate, aluminum hydroxide, aluminum hydroxide/sodium bicarbonate co-precipitate, mixture of an amino acid and a buffer, a mixture of aluminum glycinate and a buffer, a mixture of an acid salt of an amino acid and a buffer, and a mixture of an alkali salt of an amino acid and a buffer. Additional buffering agents include citric acid, sodium citrate, sodium tartrate, sodium acetate, sodium carbonate, phosphoric acid, sodium polyphosphate, potassium polyphosphate, sodium pyrophosphate, potassium pyrophosphate, disodium hydrogenphosphate, dipotassium hydrogenphosphate, trisodium phosphate, tripotassium phosphate, sodium acetate, potassium metaphosphate, magnesium oxide, magnesium hydroxide, magnesium carbonate, magnesium silicate, calcium acetate, calcium glycerophosphate, calcium chloride, calcium hydroxide, calcium lactate, calcium carbonate, calcium bicarbonate, and other calcium salts.

In some embodiments, the liquid iniparib formulation disclosed herein comprises a buffer. In some embodiments, the liquid iniparib formulation disclosed herein comprises a citrate buffer. In some embodiments, the buffer in the liquid iniparib formulation disclosed herein comprises citric acid. In some embodiments, the buffer in the liquid iniparib formulation disclosed herein comprises citric acid and sodium phosphate dibasic. In some embodiments, the liquid iniparib formulation comprises a phosphate buffer. In some embodiments, the buffer in the liquid iniparib formulation disclosed herein comprises sodium phosphate monobasic. In some embodiments, the buffer in the liquid iniparib formulation disclosed herein comprises potassium phosphate monobasic. In some embodiments, the buffer in the liquid iniparib formulation disclosed herein comprises sodium phosphate dibasic.

In some embodiments, the pH of the liquid iniparib formulation disclosed herein is between about 2.6 and about 8. In some embodiments, the pH of the liquid iniparib formulation disclosed herein is between about 6.4 and about 7.8. In some embodiments, the pH of the liquid iniparib formulation disclosed herein is between about 7.0 and about 7.6. In some embodiments, the pH of the liquid iniparib formulation disclosed herein is less than about 4, less than about 4.5, less than about 5, less than about 5.5, less than about 6, less than about 6.5, less than about 7, less than about 7.5, or less than about 8. In some embodiments, the pH of the liquid iniparib formulation disclosed herein is about 2.6, about 2.7, about 2.8, about 2.9, about 3, about 3.1, about 3.2, about 3.3, about 3.4, about 3.5, about 3.6, about 3.7, about 3.8, about 3.9, about 4, about 4.1, about 4.2, about 4.3, about 4.4, about 4.5, about 4.6, about 4.7, about 4.8, about 4.9, about 5, about 5.1, about 5.2, about 5.3, about 5.4, about 5.5, about 5.6, about 5.7, about 5.8, about 5.9, about 6, about 6.1, about 6.2, about 6.3, about 6.4, about 6.5, about 6.6, about 6.7, about 6.8, about 6.9, about 7, about 7.1, about 7.2, about 7.3, about 7.4, about 7.5, about 7.6, about 7.7, about 7.8, about 7.9, or about 8.

In some embodiments, the buffer concentration is between about 0.1 mM and about 20 mM. In some embodiments, the buffer concentration is about 0.1 mM, about 0.15 mM, about 0.2 mM, about 0.25 mM, about 0.3 mM, about 0.35 mM, about 0.4 mM, about 0.45 mM, about 0.5 mM, about 0.55 mM, about 0.6 mM, about 0.65 mM, about 0.7 mM, about 0.75 mM, about 0.8 mM, about 0.85 mM, about 0.9 mM, about 0.95 mM, about 1.0 mM, about 1.1 mM, about 1.2 nM about 1.3 nM, about 1.4 nM, about 1.5 mM, about 1.6 mM, about 1.7 mM, about 1.8 mM, about 1.9 mM, about 2.0 nM, about 2.1 mM, about 2.2 mM, about 2.3 mM, about 2.4 mM, about 2.5 mM, about 2.6 mM, about 2.7 mM, about 2.8 mM, about 2.9 mM, about 3 mM, about 3.1 mM, about 3.2 mM, about 33 mM, about 3.4 mM, about 3.5 mM, about 3.6 mM, about 3.7 mM, about 3.8 mM, about 3.9 mM, about 4 mM, about 4.1 mM, about 4.2 mM, about 4.3 mM, about 4.4 mM, about 4.5 mM, about 4.6 mM, about 4.7 mM, about 4.8 mM, about 4.9 mM, about 5 mM, about 5.1 mM, about 5.2 mM, about 5.3 mM, about 5.4 mM, about 5.5 mM, about 5.6 mM, about 5.7 mM, about 5.8 mM, about 5.9 mM, about 6 mM, about 6.1 mM, about 6.2 mM, about 6.3 mM, about 6.4 mM, about 6.5 mM, about 6.6 mM, about 6.7 mM, about 6.8 mM, about 6.9 mM, about 7 mM, about 7.1 mM, about 7.2 mM, about 7.3 mM, about 7.4 mM, about 7.5 mM, about 7.6 mM, about 7.7 mM, about 7.8 mM, about 7.9 mM, about 8 mM, about 8.1 nM, about 8.2 mM, about 8.3 mM, about 8.4 mM, about 8.5 mM, about 8.6 mM, about 8.7 mM, about 8.8 mM, about 8.9 mM, about 9 mM, about 9.1 mM, about 9.2 mM, about 9.3 mM, about 94 mM, about 9.5 mM, about 9.6 mM, about 9.7 mM, about 9.8 mM, about 9.9 mM, about 10 mM, about 11 mM, about 12 mM, about 13 mM, about 14 mM, about 15 mM, about 16 mM, about 17 mM, about 18 mM, about 19 mM, about 20 mM. In some embodiments, the buffer concentration is between about 1 mM and about 5 mM, or about 2 mM and about 4 mM. In some embodiments, the buffer concentration is about 3 mM.

Transmucosal Formulations

In another aspect, described herein is an aqueous composition comprising a pharmaceutically acceptable salt of iniparib or a solvate, metabolite, or prodrug thereof, a pharmaceutically acceptable delivery vehicle, and a mucoadhesive agent, wherein the aqueous composition is formulated for transmucosal administration.

In some embodiments, the delivery vehicle comprises water, purified water, saline, liposome, mineral oil, gel, ointment, alcohol, or a combination thereof.

In some embodiments, the mucoadhesive agent comprises hydroxypropyl-methylcellulose, monomeric alpha cyanoacrylate, polyacrylic acid, poly methacrylate derivatives, chitosan, hyaluronic acid, xanthan gum, or a combination thereof.

In some embodiments, the composition further comprises an effective amount of a vasoconstrictor.

In some embodiments, the vasoconstrictor comprises epinephrine, phenylephrine, methoxamine, norepinephrine, zolmitriptan, tetrahydrozaline, naphazoline, or a combination thereof.

In some embodiments, the composition further comprises an effective amount of a corticosteroid, an antihistamine, an anticholinergic, or a combination thereof.

In some embodiments, the composition is in a form selected from a spray, aerosol, mist, nebulae, ointment, cream, gel, paste, salve, solution, suspension, tincture, patch, and atomized vapor.

In some embodiments, the composition is formulated as a nasal spray or an inhalation solution. In some embodiments, the composition is formulated for oral administration.

Mucoadhesive Agents

Mucoadhesive drug delivery systems interact with the mucus layer covering the mucosal epithelial surface to increase the residence time of the dosage form at the site of absorption. Mucoadhesive agents include, by way of non-limiting example, a soluble polyvinylpyrrolidone polymer (PVP), a carbopol, a crosslinked poly(acrylic acid) (e.g., Carbopol 974P), a carbomer homopolymer, a carbomer copolymer, a water-swellable, but water-insoluble, fibrous, cross-linked carboxy-functional polymer, a mucoadhesive polysaccharide (e.g., a hydrophilic polysaccharide gum), one or more maltodextrin, alginate, a cross-linked alginate gum gel, a water-dispersible polycarboxylated vinyl polymer. In some embodiments, the mucoadhesive agent is a carbopol. In some embodiments, the mucoadhesive agent is selected from, by way of non-limiting example, Carbopol 974P, Carbopol Ultrez 10, sodium alginate LF120 and sodium alginate H120L. In some embodiments, the mucoadhesive agent is a cellulose. In specific embodiments, the mucoadhesive agent is a carboxymethyl-cellulose (CMC), e.g., sodium carboxymethyl-cellulose (NaCMC), microcrystalline cellulose (MCC), or a combination thereof. In one non-limiting example, the mucoadhesive agent is a combination of MCC and CMC (e.g., Avicel RC-591). In some embodiments, the CMC/MCC combination (e.g., Avicel® RC-591) is present in the composition in an amount of about 1 mg/mL to about 150 mg/mL, 1 mg/mL to about 75 mg/mL, or about 5 mg/mL to about 40 mg/mL. In certain embodiments, the CMC/MCC mixed weight ratio is between about 1/99 and about 99/1, about 20/80 and about 5/95, or about 15/85 and about 10/90. In a specific embodiment, the CMC is NaCMC and the CMC/MCC mixed weight ratio is about 11/89.

In some embodiments, a mucoadhesive drug delivery system is a composition comprising both a CMC (e.g., a CMC/MCC mixture) and maltodextrin. In certain embodiments, the combination of a CMC (e.g., a CMC/MCC mixture) and maltodextrin provide an increased residence time on an afflicted or targeted surface of the mucosa (e.g., gastrointestinal tract), when compared to a composition having a similar amount of either the CMC (e.g., a CMC/MCC mixture) or maltodextrin alone.

In some embodiments, a pharmaceutical composition, formulation, and/or dosage form of iniparib, or a pharmaceutically acceptable salt, solvate, metabolite, or prodrug thereof disclosed herein, comprises a mucoadhesive agent. In some embodiments, the mucoadhesive agent comprises one or more maltodextrin. In various aspects, the physical characteristics of maltodextrins vary depending, e.g., on the dextrose equivalent of the specific maltodextrin. In some embodiments, the dextrose equivalent of a specific maltodextrin might affect the viscosity, hygroscopicity, sweetness, humectancy, plasticity, solubility and or mucoadhesiveness of the maltodextrin. In some embodiments, a maltodextrin is selected based on the specific character that is desired to be imparted upon the pharmaceutical composition described herein. In some embodiments, a maltodextrin is selected that increases the mucoadhesive character of a composition described herein without substantially increasing the viscosity of the composition (e.g., compared to an otherwise identical composition lacking the maltodextrin). In some embodiments, the oral pharmaceutical composition comprises a second maltodextrin that increases the viscosity of the oral pharmaceutical composition (e.g., compared to an otherwise identical composition lacking the second maltodextrin). In some embodiments, the second maltodextrin that does not substantially affect the mucoadhesive characteristic of the pharmaceutical composition (e.g., compared to an otherwise identical composition lacking the second maltodextrin).

In some embodiments, the mucoadhesive agent does not substantially increase the viscosity of the oral pharmaceutical composition (e.g., compared to an otherwise identical composition lacking the mucoadhesive agent). In some embodiments, the mucoadhesive agent is chosen for its mucoadhesive properties (e.g., its ability to impart mucoadhesive character upon the oral pharmaceutical composition).

In some embodiments, a mucoadhesive agent utilized in an oral pharmaceutical composition described herein imparts an increased viscosity upon the oral pharmaceutical composition (e.g., compared to an otherwise identical composition lacking the mucoadhesive agent). In other embodiments, the mucoadhesive agent does not substantially increase the viscosity of the oral pharmaceutical composition (e.g., compared to an otherwise identical composition lacking the mucoadhesive agent).

In some embodiments, at least one mucoadhesive agent is chosen for and used in the pharmaceutical composition so the addition of the at least one mucoadhesive agent does not substantially increase the viscosity of the resulting oral pharmaceutical composition (e.g., compared to an otherwise identical composition lacking the mucoadhesive agent).

In some embodiments, at least two mucoadhesive agents are chosen for and used in the pharmaceutical composition so the addition of the at least two mucoadhesive agents do not substantially increase the viscosity of the resulting oral pharmaceutical composition (e.g., compared to an otherwise identical composition lacking the mucoadhesive agents). In some embodiments, at least one mucoadhesive agent, if taken alone in the pharmaceutical composition would increase the viscosity of the pharmaceutical composition, but taken together with all components in the pharmaceutical composition, does not substantially increase the viscosity of the resulting oral pharmaceutical composition (e.g., compared to an otherwise identical composition lacking the at least one mucoadhesive agent).

In some embodiments, the viscosity of the composition is at least about 2 centipoise (cP), at least about 5 cP, at least about 10 cP, at least about 20 cP, at least about 25 cP, at least about 35 cP, at least about 40 cP, at least about 50 cP, at least about 200 cP, or at least about 225 cP. In some embodiments, the viscosity of the composition is at least about 100 cP. In certain embodiments, the viscosity of the composition, measured at 25 degrees Celsius, is about 50 cP to about 250,000 cP, about 50 cP to about 70,000 cP, about 50 cP to about 25,000 cP, about 50 cP to about 10,000 cP, about 50 cP to about 3,000 cP, or about 50 cP to about 2,000 cP. In one aspect, the viscosity of the composition, as measured at 25 degrees Celsius, is from about 25 centipoise (cP) to about 800 cP, about 50 cP to about 800, or about 300 cP to about 800 cP (e.g., measured by a Brookfield viscometer). In another aspect, the viscosity of the composition might range from about 100 cP to about 200 cP, about 200 cP to about 300 cP, about 250 cP to about 600 cP or about 400 cP to about 600 cP. In specific embodiments, the viscosity of the formulation is about 30 cP, about 100 cP, about 200 cP, about 300 cP, about 400 cP, about 500 cP, or about 250,000 cP (e.g., as measured with a Brookfield viscometer at 25° C.).

In some embodiments, the viscosity of the composition is measured at room temperature (about 25° C.) with a shear rate of about 13.2 sec-1. In certain embodiments, provided herein is a composition having a viscosity under such conditions that is at least about 2 centipoise (cP), at least about 5 cP, at least about 10 cP, at least about 20 cP, at least about 25 cP, at least about 30 cP, at least about 35 cP, at least about 40 cP, at least about 50 cP, at least about 200 cP, at least about 225 cP, at least about 250 cP, at least about 300 cP, or at least about 400 cP. In some embodiments, the viscosity of the composition under such conditions is about 50 cP to about 250,000 cP, about 50 cP to about 70,000 cP, about 50 cP to about 25,000 cP, about 50 cP to about 10,000 cP, about 50 cP to about 3,000 cP, about 50 cP to about 2,000 cP, about 250 cP to about 250,000 cP, about 250 cP to about 70,000 cP, about 250 cP to about 25,000 cP, about 250 cP to about 10,000 cP, about 250 cP to about 3,000 cP, or about 250 cP to about 2,000 cP. In one aspect, the viscosity of the composition, as measured at 25 degrees Celsius, is from about 25 centipoise (cP) to about 800 cP, about 50 cP to about 800, or about 300 cP to about 800 cP (e.g., measured by a Brookfield viscometer). In another aspect, the viscosity of the composition under such conditions might range from about 100 cP to about 200 cP, about 200 cP to about 300 cP, about 250 cP to about 600 cP or about 400 cP to about 600 cP. In specific embodiments, the viscosity of the formulation measured under such conditions is about 30 cP, about 40 cP, about 100 cP, about 200 cP, about 300 cP, about 400 cP, about 500 cP, or about 250,000 cP.

In some embodiments, the viscosity of the composition is measured at room temperature (about 25° C.) with a shear rate of about 15 sec-1 (e.g., with a gap between the spindle and the sample chamber wall of about 6 mm or greater). In certain embodiments, provided herein is a composition having a viscosity under such conditions that is at least about 150 centipoise (cP), at least about 160 cP, at least about 170 cP, at least about 180 cP, at least about 190 cP, or at least about 200 cP. In some embodiments, the viscosity of the composition under such conditions is about 150 cP to about 250,000 cP, 160 cP to about 250,000 cP, 170 cP to about 250,000 cP, 180 cP to about 250,000 cP, or 190 cP to about 250,000 cP.

In some embodiments, the mucoadhesive agent used in any composition described herein is or comprises at least one maltodextrin.

In some embodiments, a mucoadhesive agent (e.g., maltodextrin) is substantially or at least partially dissolved in a liquid vehicle. In some embodiments, an oral pharmaceutical composition described herein comprises less than about 0.1 g or less than about 1 g of maltodextrin for every mL of liquid vehicle in the oral pharmaceutical composition. In some embodiments, a composition or formulation described herein comprises less than 2 g of maltodextrin/mL of composition, less than 1.5 g of maltodextrin/mL of composition, less than 1 g of maltodextrin/mL of composition, less than 0.5 g of maltodextrin/mL of composition, less than 0.25 g/mL of maltodextrin/mL of composition, about 0.05 g of maltodextrin/mL of composition to about 0.5 g of maltodextrin/mL of composition, about 0.05 g of maltodextrin/mL of composition to about 0.4 g of maltodextrin/mL of composition, about 0.05 g of maltodextrin/mL of composition to about 0.3 g of maltodextrin/mL of composition, about 0.1 g of maltodextrin/mL of composition to about 0.5 g of maltodextrin/mL of composition, about 0.1 g of maltodextrin/mL of composition to about 0.4 g of maltodextrin/mL of composition, about 0.1 g of maltodextrin/mL of composition to about 0.3 g of maltodextrin/mL of composition, about 0.2 g of maltodextrin/mL of composition to about 0.5 g of maltodextrin/mL of composition, about 0.2 g of maltodextrin/mL of composition to about 0.4 g of maltodextrin/mL of composition, or about 0.2 g of maltodextrin/mL of composition to about 0.3 g of maltodextrin/mL of composition. In some embodiments, the maltodextrin is substantially dissolved in the liquid vehicle. In certain embodiments, the maltodextrin has a dextrose equivalents (DE) of greater than 4, greater than 5, greater than 10, greater than 11, greater than 12, greater than 13, greater than 14, greater than 15, about 15, about 4 to about 10, about 4 to about 9, about 4 to about 8, about 11 to about 20, about 12 to about 19, about 13 to about 18, or about 14 to about 16. In specific embodiments, the first maltodextrin has a DE of about 4 to about 10, about 4 to about 9, or about 4 to about 8 and the second maltodextrin has a DE of about 10 to about 20, about 12 to about 19, or about 13 to about 18. In some embodiments, at least one maltodextrin utilized in a composition described herein has a molecular weight high enough to increase the solubility of iniparib, or to increase the suspendability of iniparib particles.

In one non-limiting example, a mucoadhesive agent can be, by way of non-limiting example, at least two particulate components selected from titanium dioxide, silicon dioxide, and clay. In some embodiments, when the composition is not further diluted with any liquid prior to administration, the level of silicon dioxide is from about 3% to about 15%, by weight of the composition. In certain embodiments, silicon dioxide is selected from, by way of non-limiting example, fumed silicon dioxide, precipitated silicon dioxide, coacervated silicon dioxide, gel silicon dioxide, and mixtures thereof. In some embodiments, clay is selected from, by way of non-limiting example, kaolin minerals, serpentine minerals, smectites, illite or mixtures thereof. In certain embodiments, clay is selected from, by way of non-limiting example, laponite, bentonite, hectorite, saponite, montmorillonites or mixtures thereof.

In some embodiments, the mucoadhesive agent is selected in an amount sufficient to cause the iniparib containing pharmaceutical composition to adhere to or resides upon a surface of the mucous membrane for 5 seconds, 10 seconds, 15 seconds, 30 seconds, 45 seconds, or 1 minute following application to the surface of the mucous membrane. In certain embodiments, the mucoadhesive agent is selected in an amount sufficient to cause the iniparib containing composition to adhere to or reside upon the surface of the mucous membrane for 1.5, 2, 3, 4, 5, 6, 7, 8, 9, 10, 15, 20, 25, 30, 35, 40, 45, 50, 55 or 60 minutes after application to the surface of the mucous membrane. In some embodiments, the amount of iniparib containing composition that adheres to a surface of the mucous membrane for 5 seconds, 10 seconds, or 0.25, 0.5, 0.75, 1, 1.5, 2, 3, 4, 5, 6, 7, 8, 9, 10, 15, 20, 25, 30, 35, 40, 45, 50, 55 or 60 minutes is at least 1%, at least 2%, at least 3%, at least 4%, at least 5%, at least 6%, at least 7%, at least 8%, at least 9%, at least 10%, at least 15%, at least 20%, at least 30%, at least 40%, at least 50%, at least 60%, at least 70%, at least 80%, at least 90% or at least 95% by weight after administration to the surface of the mucous membrane. In specific embodiments, at least 50% of the pharmaceutical composition adheres to or resides upon the surface of the mucous membrane for at least 1 or at least 15 minutes following application to the surface of the mucous membrane.

In certain embodiments, the mucoadhesive agent is selected and selected in an amount sufficient to cause the iniparib to adhere to and/or be absorbed at a surface of the mucous membrane after 5 seconds, 10 seconds, or 0.25, 0.5, 0.75, 1, 1.5, 2, 3, 4, 5, 6, 7, 8, 9, 10, 15, 20, 25, 30, 35, 40, 45, 50, 55 or 60 minutes following application to the surface of the mucous membrane. In some embodiments, the amount of iniparib that adheres to and/or is absorbed at the surface of the mucous membrane for 5 seconds, 10 seconds, or 0.25, 0.5, 0.75, 1, 1.5, 2, 3, 4, 5, 6, 7, 8, 9, 10, 15, 20, 25, 30, 35, 40, 45, 50, 55 or 60 minutes is at least 1%, at least 2%, at least 3%, at least 4%, at least 5%, at least 6%, at least 7%, at least 8%, at least 9%, at least 10%, at least 15%, at least 20%, at least 30%, at least 40%, at least 50%, at least 60%, at least 70%, at least 80%, at least 90% or at least 95% by weight following administration to the surface of the mucous membrane. In some embodiments, at least 50% of the iniparib adheres to and/or is absorbed by the surface of the mucous membrane at least 1 or at least 15 minutes after administration to the surface of the mucous membrane.

Optional viscosity-enhancing excipients used in pharmaceutical compositions described herein include, by way of non-limiting example, a crosslinked poly(acrylic acid) (e.g., Carbopol 974P), glycerin, a carbomer homopolymer, a carbomer copolymer, acacia (gum arabic), agar, aluminum magnesium silicate, sodium alginate, sodium stearate, bladderwrack, bentonite, carbomer, carrageenan, Carbopol, cellulose, microcrystalline cellulose (MCC), ceratonia, chondrus, dextrose, furcellaran, gelatin, Ghatti gum, guar gum, hectorite, lactose, sucrose, maltodextrin, mannitol, sorbitol, honey, maize starch, wheat starch, rice starch, potato starch, gelatin, sterculia gum, xanthum gum, polyethylene glycol (e.g. PEG 200-4500) gum tragacanth, ethyl cellulose, ethylhydroxyethyl cellulose, ethylmethyl cellulose, methyl cellulose, hydroxyethyl cellulose, hydroxyethylmethyl cellulose, hydroxypropyl cellulose, poly(hydroxyethyl methacrylate), oxypolygelatin, pectin, polygeline, povidone, propylene carbonate, methyl vinyl ether/maleic anhydride copolymer (PVM/MA), poly(methoxyethyl methacrylate), poly(methoxyethoxyethyl methacrylate), hydroxypropyl cellulose, hydroxypropylmethyl-cellulose, carboxymethyl-cellulose (CMC) (including, e.g., sodium carboxymethyl-cellulose (NaCMC)), silicon dioxide, polyvinylpyrrolidone (PVP: povidone), Splenda® (dextrose, maltodextrin and sucralose) or combinations thereof.

In certain embodiments, a pharmaceutical composition described herein is a non-Newtonian fluid or a Newtonian fluid. In some embodiments, a pharmaceutical composition described herein is a non-Newtonian fluid. In specific embodiments, the non-Newtonian fluid is a plastic, pseudoplastic or dilatant non-Newtonian fluid. In some specific embodiments, the non-Newtonian fluid is thixotropic. In certain embodiments, the non-Newtonian fluid composition thins with shear, and thickens upon the absence of shear. Thus, in some embodiments, provided herein is a fluid pharmaceutical composition that is suitable for easy pouring following mild or moderate agitation. Furthermore, in some embodiments, provided herein is a fluid pharmaceutical composition that while being suitable for easy pouring following mild or moderate agitation becomes viscous enough upon oral administration to allow the pharmaceutical composition to at least partially coat the esophagus and topically deliver a therapeutically effective amount of iniparib to the esophagus.

Excipients

In certain embodiments, one or more iniparib formulations described above further comprise an excipient. In some embodiments, aqueous suspensions of the pharmaceutical composition disclosed herein contain pharmaceutically acceptable excipients, such as a suspending agent (e.g., methyl cellulose), a wetting agent (e.g., lecithin, lysolecithin and/or a long-chain fatty alcohol), as well as coloring agents, preservatives, flavoring agents, and the like.

Pharmaceutical compositions disclosed herein might also be integrated into foodstuffs, e.g., cream cheese, butter, salad dressing, or ice cream to facilitate solubilization, administration, and/or compliance in certain patient populations.

Pharmaceutical preparations for oral use might be obtained as a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; flavoring elements, cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents might be added, such as the cross-linked polyvinylpyrrolidone, agar, or alginic acid or a salt thereof such as sodium alginate. The active compounds might also be formulated as a sustained release preparation.

Dragee cores might be provided with suitable coatings. For this purpose, concentrated sugar solutions might be used, which might optionally contain gum arabic, talc, polyvinylpyrrolidone, carbopol gel, polyethylene glycol, and/or titanium dioxide, lacquer solutions, and suitable organic solvents or solvent mixtures. Dyestuffs or pigments might be added to the tablets or dragee coatings for identification or to characterize different combinations of active compound doses.

Pharmaceutical preparations that might be used orally include push-fit capsules made of gelatin, as well as soft, sealed capsules made of gelatin and a plasticizer, such as glycerol or sorbitol. The push-fit capsules might contain the active ingredients in admixture with filler such as lactose, binders such as starches, and/or lubricants such as talc or magnesium stearate and, optionally, stabilizers. In soft capsules, the active compounds might be dissolved or suspended in suitable liquids, such as fatty oils, liquid paraffin, or liquid polyethylene glycols. In addition, stabilizers might be added. All formulations for oral administration should be in dosages suitable for administration.

For injection, the pharmaceutical compositions disclosed herein might be formulated in aqueous solutions, preferably in physiologically compatible buffers such as Hank's solution, Ringer's solution, or physiological saline buffer. Such compositions might also include one or more excipients, for example, preservatives, solubilizers, fillers, lubricants, stabilizers, albumin, and the like. Methods of formulation are known in the art, for example, as disclosed in Remington's Pharmaceutical Sciences, latest edition, Mack Publishing Co., Easton, Pa. These pharmaceutical compositions might also be formulated for transmucosal administration, buccal administration, for administration by inhalation, for parental administration, for transdermal administration, and rectal administration.

In addition to the disclosed formulations, the pharmaceutical compositions might also be formulated as a depot preparation. Such long acting formulations might be administered by implantation or transcutaneous delivery (for example subcutaneously or intramuscularly), intramuscular injection or use of a transdermal patch. Thus, for example, the pharmaceutical compositions might be formulated with suitable polymeric or hydrophobic materials (for example as an emulsion in an acceptable oil) or ion exchange resins, or as sparingly soluble derivatives, for example, as a sparingly soluble salt.

In some embodiments, the pharmaceutical formulations include, but are not limited to, aqueous liquid dispersions, self-emulsifying dispersions, solid solutions, liposomal dispersions, aerosols, solid dosage forms, powders, immediate-release formulations, controlled-release formulations, fast melt formulations, tablets, capsules, pills, delayed release formulations, extended release formulations, pulsatile release formulations, multiparticulate formulations (e.g., nanoparticle formulations), and mixed immediate-and controlled-release formulations.

In some instances, the pharmaceutical formulation includes multiparticulate formulations. In some instances, the pharmaceutical formulation includes nanoparticle formulations. In some instances, nanoparticles comprise cyclodextrins or lipids. In some cases, nanoparticles comprise solid lipid nanoparticles, polymeric nanoparticles, self-emulsifying nanoparticles, liposomes, microemulsions, or micellar solutions. Additional exemplary nanoparticles include, but are not limited to, paramagnetic nanoparticles, superparamagnetic nanoparticles, metal nanoparticles, fullerene-like materials, inorganic nanotubes, dendrimers (such as with covalently attached metal chelates), nanofibers, nanohorns, nano-onions, nanorods, nanoropes and quantum dots. In some instances, a nanoparticle is a metal nanoparticle, e.g., a nanoparticle of scandium, titanium, vanadium, chromium, manganese, iron, cobalt, nickel, copper, zinc, yttrium, zirconium, niobium, molybdenum, ruthenium, rhodium, palladium, silver, cadmium, hafnium, tantalum, tungsten, rhenium, osmium, iridium, platinum, gold, gadolinium, aluminum, gallium, indium, tin, thallium, lead, bismuth, magnesium, calcium, strontium, barium, lithium, sodium, potassium, boron, silicon, phosphorus, germanium, arsenic, antimony, and combinations, alloys or oxides thereof.

In some instances, a nanoparticle includes a core or a core and a shell, as in a core-shell nanoparticle.

In some instances, a nanoparticle is further coated with molecules for attachment of functional elements. In some instances, a coating comprises chondroitin sulfate, dextran sulfate, carboxymethyl dextran, alginic acid, pectin, carragheenan, fucoidan, agaropectin, porphyran, karaya gum, gellan gum, xanthan gum, hyaluronic acids, glucosamine, galactosamine, chitin (or chitosan), polyglutamic acid, polyaspartic acid, lysozyme, cytochrome C, ribonuclease, trypsinogen, chymotrypsinogen, α-chymotrypsin, polylysine, polyarginine, histone, protamine, ovalbumin or dextrin or cyclodextrin. In some instances, a nanoparticle comprises a graphene-coated nanoparticle.

In some cases, a nanoparticle has at least one dimension of less than about 500 nm, 400 nm, 300 nm, 200 nm, or 100 nm.

In some instances, the nanoparticle formulation comprises paramagnetic nanoparticles, superparamagnetic nanoparticles, metal nanoparticles, fullerene-like materials, inorganic nanotubes, dendrimers (such as with covalently attached metal chelates), nanofibers, nanohorns, nano-onions, nanorods, nanoropes or quantum dots. In some instances, iniparib or a pharmaceutically acceptable salt, solvate, metabolite, or prodrug thereof is conjugated either directly or indirectly to the nanoparticle. In some instances, at least 1, 5, 10, 15, 20, 30, 40, 50, 60, 70, 80, 90, 100 or more iniparib or a pharmaceutically acceptable salt, solvate, metabolite, or prodrug thereof is conjugated either directly or indirectly to a nanoparticle.

In some embodiments, the pharmaceutical formulations include a carrier or carrier materials selected on the basis of compatibility with the composition disclosed herein, and the release profile properties of the desired dosage form. Pharmaceutically compatible carrier materials include, but are not limited to, acacia, gelatin, colloidal silicon dioxide, calcium glycerophosphate, calcium lactate, maltodextrin, glycerin, magnesium silicate, polyvinylpyrrollidone (PVP), cholesterol, cholesterol esters, sodium caseinate, soy lecithin, taurocholic acid, phosphotidylcholine, sodium chloride, tricalcium phosphate, dipotassium phosphate, cellulose and cellulose conjugates, sugars sodium stearoyl lactylate, carrageenan, monoglyceride, diglyceride, pregelatinized starch, and any combination thereof. See, e.g., *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pa. 1975; Liberman, H. A. and Lachman, L., Eds., *Pharmaceutical Dosage Forms*, Marcel Decker, New York, N.Y., 1980; and *Pharmaceutical Dosage Forms* and Drug Delivery Systems, Seventh Ed. (Lippincott Williams & Wilkins 1999).

In some instances, the pharmaceutical formulations further include pH adjusting agents or buffering agents which include acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

In some instances, the pharmaceutical formulation includes one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

In some instances, the pharmaceutical formulations include binder which are used to hold iniparib or a pharmaceutically acceptable salt, solvate, isomer, tautomer, metabolite, analog, or prodrug thereof and inactive ingredients together in a cohesive mix. Suitable binders include, but are not limited to, carboxymethylcellulose, methylcellulose (e.g., Methocel®), hydroxypropylmethylcellulose (e.g. Hypromellose USP Pharmacoat-603, hydroxypropylmethylcellulose acetate stearate (Agoate HS-LF and HS), hydroxyethylcellulose, hydroxypropylcellulose (e.g., Klucel®), ethylcellulose (e.g., Ethocel®), and microcrystalline cellulose (e.g., Avicel®), microcrystalline dextrose, amylose, magnesium aluminum silicate, polysaccharide acids, bentonites, gelatin, polyvinylpyrrolidone/vinyl acetate copolymer, crospovidone, povidone, starch, pregelatinized starch, tragacanth, dextrin, a sugar, such as sucrose (e.g., Dipac®), glucose, dextrose, molasses, mannitol, sorbitol, xylitol (e.g., Xylitab®), lactose, a natural or synthetic gum such as acacia, tragacanth, ghatti gum, mucilage of isapol husks, starch, polyvinylpyrrolidone (e.g., Povidone® CL, Kollidon® CL, Polyplasdone® XL-10, and Povidone® K-12), larch arabogalactan, Veegum®, polyethylene glycol, waxes, sodium alginate, and any combination thereof.

In some instances, the pharmaceutical formulations further include diluent which are used to stabilize iniparib or a pharmaceutically acceptable salt, solvate, isomer, tautomer, metabolite, analog, or prodrug thereof because they provide a more stable environment. Salts dissolved in buffered solutions (which also provide pH control or maintenance) are utilized as diluents in the art, including, but not limited to a phosphate buffered saline solution. In certain instances, diluents increase bulk of the composition to facilitate compression or create sufficient bulk for homogenous blend for capsule filling. Such compounds include e.g., lactose, starch, mannitol, sorbitol, dextrose, microcrystalline cellulose such as Avicel®; dibasic calcium phosphate, dicalcium phosphate dihydrate; tricalcium phosphate, calcium phosphate; anhydrous lactose, spray-dried lactose; pregelatinized starch, compressible sugar, such as Di-Pac® (Amstar); mannitol, hydroxypropylmethylcellulose, hydroxypropylmethylcellulose acetate stearate, sucrose-based diluents, confectioner's sugar; monobasic calcium sulfate monohydrate, calcium sulfate dihydrate; calcium lactate trihydrate, dextrates; hydrolyzed cereal solids, amylose; powdered cellulose, calcium carbonate; glycine, kaolin; mannitol, sodium chloride; inositol, bentonite, and any combination thereof.

In some cases, the pharmaceutical formulations include disintegration agents or disintegrants to facilitate the breakup or disintegration of a substance. The term "disintegrate" include both the dissolution and dispersion of the dosage form when contacted with gastrointestinal fluid. Examples of disintegration agents include a starch, e.g., a natural starch such as corn starch or potato starch, a pregelatinized starch such as National 1551 or Amijel®, or sodium starch glycolate such as Promogel® or Explotab©, a cellulose such as a wood product, methylcrystalline cellulose, e.g., Avicel®, Avicel® PH101, Avicel® PH102, Avicel® PH105, Elcema® P100, Emcocel®, Vivacel®, Ming Tia®, and Solka-Floc®, methylcellulose, croscarmellose, or a cross-linked cellulose, such as cross-linked sodium carboxymethylcellulose (Ac-Di-Sol*), cross-linked carboxymethylcellulose, or cross-linked croscarmellose, a cross-linked starch such as sodium starch glycolate, a cross-linked polymer such as crospovidone, a cross-linked polyvinylpyrrolidone, alginate such as alginic acid or a salt of alginic acid such as sodium alginate, a clay such as Veegum® HV (magnesium aluminum silicate), a gum such as agar, guar, locust bean, Karaya, pectin, or tragacanth, sodium starch glycolate, bentonite, a natural sponge, a surfactant, a resin such as a cation-exchange resin, citrus pulp, sodium lauryl sulfate, sodium lauryl sulfate in combination starch, and any combination thereof.

In some instances, the pharmaceutical formulations include filling agents such as lactose, calcium carbonate, calcium phosphate, dibasic calcium phosphate, calcium sulfate, microcrystalline cellulose, cellulose powder, dextrose, dextrates, dextran, starches, pregelatinized starch, hydroxypropylmethylcellulose (HPMC), hydroxypropylmethycellulose phthalate, hydroxypropylmethylcellulose acetate stearate (HPMCAS), sucrose, xylitol, lactitol, mannitol, sorbitol, sodium chloride, polyethylene glycol, and any combination thereof.

Lubricants and glidants are also optionally included in the pharmaceutical formulations disclosed herein for preventing, reducing or inhibiting adhesion or friction of materials.

Exemplary lubricants include, e.g., stearic acid, calcium hydroxide, talc, sodium stearyl fumerate, a hydrocarbon such as mineral oil, or hydrogenated vegetable oil such as hydrogenated soybean oil (Sterotex®), higher fatty acids and their alkali-metal and alkaline earth metal salts, such as aluminum, calcium, magnesium, zinc, stearic acid, sodium stearates, glycerol, talc, waxes, Stearowet®, boric acid, sodium benzoate, sodium acetate, sodium chloride, leucine, a polyethylene glycol (e.g., PEG-4000) or a methoxypolyethylene glycol such as Carbowax™, sodium oleate, sodium benzoate, glyceryl behenate, polyethylene glycol, magnesium or sodium lauryl sulfate, colloidal silica such as Syloid™, Cab-O-Sil®, a starch such as corn starch, silicone oil, a surfactant, and any combination thereof.

Plasticizers include compounds used to soften the microencapsulation material or film coatings to make them less brittle. Suitable plasticizers include, e.g., polyethylene glycols such as PEG 300, PEG 400, PEG 600, PEG 1450, PEG 3350, and PEG 800, stearic acid, propylene glycol, oleic acid, triethyl cellulose and triacetin. Plasticizers also function as dispersing agents or wetting agents.

Solubilizers include compounds such as triacetin, triethylcitrate, ethyl oleate, ethyl caprylate, sodium lauryl sulfate, sodium doccusate, vitamin E TPGS, dimethylacetamide, N-methylpyrrolidone, N-hydroxyethylpyrrolidone, polyvinylpyrrolidone, hydroxypropylmethyl cellulose, hydroxypropyl cyclodextrins, ethanol, n-butanol, isopropyl alcohol, cholesterol, bile salts, polyethylene glycol 200-600, glycofurol, transcutol, propylene glycol, and dimethyl isosorbide and any combination thereof.

Stabilizers include compounds such as any antioxidation agents, buffers, acids, preservatives and any combination thereof.

Suspending agents include compounds such as polyvinylpyrrolidone, e.g., polyvinylpyrrolidone K12, polyvinylpyrrolidone K17, polyvinylpyrrolidone K25, or polyvinylpyrrolidone K30, vinyl pyrrolidone/vinyl acetate copolymer (S630), polyethylene glycol, e.g., the polyethylene glycol has a molecular weight of about 300 to about 6000, or about 3350 to about 4000, or about 7000 to about 5400, sodium carboxymethylcellulose, methylcellulose, hydroxypropylmethylcellulose, hydroxymethylcellulose acetate stearate, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone, and any combination thereof.

Surfactants include compounds such as sodium lauryl sulfate, sodium docusate, Tween 60 or 80, triacetin, vitamin E TPGS, sorbitan monooleate, polyoxyethylene sorbitan monooleate, polysorbates, polaxomers, bile salts, glyceryl monostearate, copolymers of ethylene oxide and propylene oxide, e.g., Pluronic© (BASF), and any combination thereof. Additional surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40. Sometimes, surfactants are included to enhance physical stability or for other purposes.

Viscosity enhancing agents include, e.g., methyl cellulose, xanthan gum, carboxymethyl cellulose, hydroxypropyl cellulose, hydroxypropylmethyl cellulose, hydroxypropylmethyl cellulose acetate stearate, hydroxypropylmethyl cellulose phthalate, carbomer, polyvinyl alcohol, alginates, acacia, chitosans and combinations thereof.

Wetting agents include compounds such as oleic acid, glyceryl monostearate, sorbitan monooleate, sorbitan monolaurate, triethanolamine oleate, polyoxyethylene sorbitan monooleate, polyoxyethylene sorbitan monolaurate, sodium docusate, sodium oleate, sodium lauryl sulfate, sodium doccusate, triacetin, Tween 80, vitamin E TPGS, ammonium salts, and any combination thereof.

Antifoaming agents are chemical additive that reduces and hinders the formation of foam in the preparation of an oral liquid formulation. The terms antifoaming agent and defoamer are often used interchangeably. Commonly used agents are insoluble oils, polydimethylsiloxanes (e.g., simethicone) and other silicones, certain alcohols, stearates and glycols. The additive is used to prevent formation of foam or is added to break foam already formed. Antifoaming agents reduce foaming in the preparation of an oral liquid formulation which might result in coagulation of aqueous dispersions. In some embodiments, the iniparib compositions described herein comprise an antifoaming agent. In some embodiments, the antifoaming agent is simethicone.

In some embodiments, there is a considerable overlap between excipients used in the pharmaceutical compositions, formulations, and dosage forms of iniparib, or a pharmaceutically acceptable salt, solvate, metabolite, or prodrug thereof described herein. Thus, the above-listed additives should be taken as merely exemplary, and not limiting, of the types of additives that might be included in solid dosage forms of the pharmaceutical compositions described herein.

Methods of Pharmaceutical Formulations and Routes of Administration

Pharmaceutical compositions might be formulated in a conventional manner using one or more physiologically acceptable carriers including excipients and auxiliaries which facilitate processing of the active compounds into preparations which might be used pharmaceutically. Proper formulation is dependent upon the route of administration chosen. Additional details about suitable excipients for pharmaceutical compositions described herein might be found, for example, in *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pa. 1975; Liberman, H. A. and Lachman, L., Eds., *Pharmaceutical Dosage Forms*, Marcel Decker, New York, N.Y., 1980; and *Pharmaceutical Dosage Forms* and Drug Delivery Systems, Seventh Ed. (Lippincott Williams & Wilkins 1999), herein incorporated by reference for such disclosure.

The pharmaceutical compositions described herein are administered to a subject by multiple administration routes, including but not limited to, oral, parenteral (e.g., intravenous, subcutaneous, intramuscular), intranasal, inhalation, buccal, topical, rectal, or transdermal administration routes. In some embodiments, pharmaceutical compositions described herein, which include iniparib or a pharmaceutically acceptable salt, solvate, metabolite, or prodrug thereof, are formulated into any suitable dosage form, including but not limited to, emulsions suitable for injection, nanosuspensions suitable for injection, aqueous oral dispersions, liquids, gels, syrups, elixirs, slurries, suspensions, aerosols, controlled-release formulations, fast melt formulations, effervescent formulations, lyophilized formulations, tablets, powders, pills, dragees, capsules, delayed release formulations, extended release formulations, pulsatile release formulations, multiparticulates formulations, and mixed immediate-release and controlled-release formulations.

In some embodiments, the pharmaceutical composition for oral use is a tablet, (including a suspension tablet, a fast-melt tablet, a bite-disintegration tablet, a rapid-disintegration tablet, an effervescent tablet, or a caplet), a pill, a powder (including a sterile packaged powder, a dispensable powder, or an effervescent powder), a capsule (including both soft or hard capsules, e.g., capsules made from animal-derived gelatin or plant-derived HPMC, or "sprinkle capsules"), solid dispersion, solid solution, bioerodible dosage form, controlled-release formulations, pulsatile release dosage forms, multiparticulate dosage forms, pellets, granules, or an aerosol. In some embodiments, the pharmaceutical composition for oral use is a solid dosage form, e.g., tablets, effervescent tablets, and capsules. In some embodiments, the solid dosage form are prepared by mixing particles of iniparib or a pharmaceutically acceptable salt, solvate, metabolite, or prodrug thereof, with one or more pharmaceutical excipients to form a bulk blend composition. When referring to these bulk blend compositions as homogeneous, it is meant that the particles of iniparib or a pharmaceutically acceptable salt, solvate, metabolite, or prodrug thereof, are dispersed evenly throughout the composition so that the composition might be subdivided into equally effective unit dosage forms, such as tablets, pills, and capsules. The individual unit dosages might also include film coatings, which disintegrate upon oral ingestion or upon contact with diluent.

For oral administration, the pharmaceutical compositions disclosed herein might be formulated readily by combining the active compound(s) with pharmaceutically acceptable carriers well known in the art. Such carriers enable the compositions disclosed herein to be formulated as tablets, including chewable tablets, pills, dragees, capsules, lozenges, hard candy, liquids, gels, syrups, slurries, powders, suspensions, elixirs, wafers, and the like, for oral ingestion by a patient to be treated. Such formulations might comprise pharmaceutically acceptable carriers including solid diluents or fillers, sterile aqueous media and various non-toxic organic solvents. Generally, the compositions disclosed herein will be included at concentration levels ranging from about 0.5%, about 5%, about 10%, about 20%, or about 30% to about 50%, about 60%, about 70%, about 80% or about 90% by weight of the total composition of oral dosage forms, in an amount sufficient to provide a desired unit of dosage.

Dosage

In some embodiments, the amount of iniparib or a pharmaceutically acceptable salt, solvate, metabolite, or prodrug thereof used in a pharmaceutical composition is about 1.0 mg/ml to about 30.0 mg/ml. In some embodiments, the amount of iniparib or a pharmaceutically acceptable salt, solvate, metabolite, or prodrug thereof used in a pharmaceutical composition is about 1.0 mg/ml, about 1.1 mg/ml, about 1.2 mg/ml, about 1.3 mg/ml, about 1.4 mg/ml, about 1.5 mg/ml, about 1.6 mg/ml, about 1.7 mg/ml, about 1.8 mg/ml, about 1.9 mg/ml, about 2.0 mg/ml, about 2.1 mg/ml, about 2.2 mg/ml, about 2.3 mg/ml, about 2.4 mg/ml, about 2.5 mg/ml, about 2.6 mg/ml, about 2.7 mg/ml, about 2.8 mg/ml, about 2.9 mg/ml, about 3.0 mg/ml, about 3.1 mg/ml, about 3.2 mg/ml, about 3.3 mg/ml, about 3.4 mg/ml, about 3.5 mg/ml, about 3.6 mg/ml, about 3.7 mg/ml, about 3.8 mg/ml, about 3.9 mg/ml, about 4.0 mg/ml, about 4.1 mg/ml, about 4.2 mg/ml, about 4.3 mg/ml, about 4.4 mg/ml, about 4.5 mg/ml, about 4.6 mg/ml, about 4.7 mg/ml, about 4.8 mg/ml, about 4.9 mg/ml, about 5.0 mg/ml, about 5.1 mg/ml, about 5.2 mg/ml, about 5.3 mg/ml, about 5.4 mg/ml, about 5.5 mg/ml, about 5.6 mg/ml, about 5.7 mg/ml, about 5.8 mg/ml, about 5.9 mg/ml, about 6.0 mg/ml, about 6.1 mg/ml, about 6.2 mg/ml, about 6.3 mg/ml, about 6.4 mg/ml, about 6.5 mg/ml, about 6.6 mg/ml, about 6.7 mg/ml, about 6.8 mg/ml, about 6.9 mg/ml, about 7.0 mg/ml, about 7.1 mg/ml, about 7.2 mg/ml, about 7.3 mg/ml, about 7.4 mg/ml, about 7.5 mg/ml, about 7.6 mg/ml, about 7.7 mg/ml, about 7.8 mg/ml, about 7.9 mg/ml, about 8.0 mg/ml, about 8.1 mg/ml, about 8.2 mg/ml, about 8.3 mg/ml, about 8.4 mg/ml, about 8.5 mg/ml, about 8.6 mg/ml, about 8.7 mg/ml, about 8.8 mg/ml, about 8.9 mg/ml, about 9.0 mg/ml, about 9.1 mg/ml, about 9.2 mg/ml, about 9.3 mg/ml, about 9.4 mg/ml, about 9.5 mg/ml, about 9.6 mg/ml, about 9.7 mg/ml, about 9.8 mg/ml, about 9.9 mg/ml, about 10.0 mg/ml, about 10.1 mg/ml, about 10.2 mg/ml, about 10.3 mg/ml, about 10.4 mg/ml, about 10.5 mg/ml, about 10.6 mg/ml, about 10.7 mg/ml, about 10.8 mg/ml, about 10.9 mg/ml, about 11.0 mg/ml, about 11.1 mg/ml, about 11.2 mg/ml, about 11.3 mg/ml, about 11.4 mg/ml, about 11.5 mg/ml, about 11.6 mg/ml, about 11.7 mg/ml, about 11.8 mg/ml, about 11.9 mg/ml, about 12.0 mg/ml, about 12.1 mg/ml, about 12.2 mg/ml, about 12.3 mg/ml, about 12.4 mg/ml, about 12.5 mg/ml, about 12.6 mg/ml, about 12.7 mg/ml, about 12.8 mg/ml, about 12.9 mg/ml, about 13.0 mg/ml, about 13.1 mg/ml, about 13.2 mg/ml, about 13.3 mg/ml, about 13.4 mg/ml, about 13.5 mg/ml, about 13.6 mg/ml, about 13.7 mg/ml, about 13.8 mg/ml, about 13.0 mg/ml, about 13.1 mg/ml, about 13.2 mg/ml, about 13.3 mg/ml, about 13.4 mg/ml, about 13.5 mg/ml, about 13.6 mg/ml, about 13.7 mg/ml, about 13.8 mg/ml, about 13.9 mg/ml, about 14.0 mg/ml, about 14.1 mg/ml, about 14.2 mg/ml, about 14.3 mg/ml, about 14.4 mg/ml, about 14.5 mg/ml, about 14.6 mg/ml, about 14.7 mg/ml, about 14.8 mg/ml, about 14.9 mg/ml, about 15.0 mg/ml, about 15.5 mg/ml, about 16.0 mg/ml, about 16.5 mg/ml, about 17.0 mg/ml, about 17.5 mg/ml, about 18.0 mg/ml, about 18.5 mg/ml, about 19.0 mg/ml, about 19.5 mg/ml, about 20.0 mg/ml, about 21.0 mg/ml, about 22.0 mg/ml, about 23.0 mg/ml, about 24.0 mg/ml, about 25.0 mg/ml, about 27.5 mg/ml, about 30.0 mg/ml.

In some embodiments, the amount of iniparib in a pharmaceutically acceptable salt, solvate, metabolite, analog, or prodrug thereof in the pharmaceutical composition corresponds to about 0.8 mg/ml to about 24.0 mg/ml of iniparib. In other embodiments, the amount of iniparib or a pharmaceutically acceptable salt, solvate, metabolite, or prodrug thereof in the pharmaceutical composition corresponds to about 0.8 mg/ml, about 0.9 mg/ml, about 1.0 mg/ml, about 1.1 mg/ml, about 1.2 mg/ml, about 1.3 mg/ml, about 1.4 mg/ml, about 1.5 mg/ml, about 1.6 mg/ml, about 1.7 mg/ml, about 1.8 mg/ml, about 1.9 mg/ml, about 2.0 mg/ml, about 2.1 mg/ml, about 2.2 mg/ml, about 2.3 mg/ml, about 2.4 mg/ml, about 2.5 mg/ml, about 2.6 mg/ml, about 2.7 mg/ml, about 2.8 mg/ml, about 2.9 mg/ml, about 3.0 mg/ml, about 3.1 mg/ml, about 3.2 mg/ml, about 3.3 mg/ml, about 3.4 mg/ml, about 3.5 mg/ml, about 3.6 mg/ml, about 3.7 mg/ml, about 3.8 mg/ml, about 3.9 mg/ml, about 4.0 mg/ml, about 4.1 mg/ml, about 4.2 mg/ml, about 4.3 mg/ml, about 4.4 mg/ml, about 4.5 mg/ml, about 4.6 mg/ml, about 4.7 mg/ml, about 4.8 mg/ml, about 4.9 mg/ml, about 5.0 mg/ml, about 5.1 mg/ml, about 5.2 mg/ml, about 5.3 mg/ml, about 5.4 mg/ml, about 5.5 mg/ml, about 5.6 mg/ml, about 5.7 mg/ml, about 5.8 mg/ml, about 5.9 mg/ml, about 6.0 mg/ml, about 6.1 mg/ml, about 6.2 mg/ml, about 6.3 mg/ml, about 6.4 mg/ml, about 6.5 mg/ml, about 6.6 mg/ml, about 6.7 mg/ml, about 6.8 mg/ml, about 6.9 mg/ml, about 7.0 mg/ml, about 7.1 mg/ml, about 7.2 mg/ml, about 7.3 mg/ml, about 7.4 mg/ml, about 7.5 mg/ml, about 7.6 mg/ml, about 7.7 mg/ml, about 7.8 mg/ml, about 7.9 mg/ml, about 8.0 mg/ml, about 8.1 mg/ml, about 8.2 mg/ml, about 8.3 mg/ml, about 8.4 mg/ml, about 8.5 mg/ml, about 8.6 mg/ml, about 8.7 mg/ml, about 8.8 mg/ml, about 8.9 mg/ml, about 9.0 mg/ml, about 9.1 mg/ml, about 9.2 mg/ml, about 9.3 mg/ml, about 9.4 mg/ml, about 9.5 mg/ml, about 9.6 mg/ml, about 9.7 mg/ml, about 9.8 mg/ml, about 9.9 mg/ml, about 10.0 mg/ml, about 10.1 mg/ml, about 10.2 mg/ml, about 10.3 mg/ml, about 10.4 mg/ml, about 10.5 mg/ml, about 10.6 mg/ml, about 10.7 mg/ml, about 10.8 mg/ml, about 10.9 mg/ml, about 11.0 mg/ml, about 11.1 mg/ml, about 11.2 mg/ml, about 11.3 mg/ml, about 11.4 mg/ml, about 11.5 mg/ml, about 11.6 mg/ml, about 11.7 mg/ml, about 11.8 mg/ml, about 11.9 mg/ml, about 12.0 mg/ml, about 12.1 mg/ml, about 12.2 mg/ml, about 12.3 mg/ml, about 12.4 mg/ml, about 12.5 mg/ml, about 12.6 mg/ml, about 12.7 mg/ml, about 12.8 mg/ml, about 12.9 mg/ml, about 13.0 mg/ml, about 13.1 mg/ml, about 13.2 mg/ml, about 13.3 mg/ml, about 13.4 mg/ml, about 13.5 mg/ml, about 13.6 mg/ml, about 13.7 mg/ml, about 13.8 mg/ml, about 13.9 mg/ml, about 13.0 mg/ml, about 13.1 mg/ml, about 13.2 mg/ml, about 13.3 mg/ml, about 13.4 mg/ml, about 13.5 mg/ml, about 13.6 mg/ml, about 13.7 mg/ml, about 13.8 mg/ml, about 13.9 mg/ml, about 14.0 mg/ml, about 14.1 mg/ml, about 14.2 mg/ml, about 14.3 mg/ml, about 14.4 mg/ml, about 14.5 mg/ml, about 14.6 mg/ml, about 14.7 mg/ml, about 14.8 mg/ml, about 14.9 mg/ml, about 15.0 mg/ml, about 15.5 mg/ml, about 16.0 mg/ml, about 16.5 mg/ml, about 17.0 mg/ml, about 17.5 mg/ml, about 18.0 mg/ml, about 18.5 mg/ml, about 19.0 mg/ml, about 19.5 mg/ml, about 20.0 mg/ml, about 21.0 mg/ml, about 22.0 mg/ml, about 23.0 mg/ml, or about 24.0 mg/ml of iniparib.

In some embodiments, the amount of iniparib or a pharmaceutically acceptable salt, solvate, metabolite, or prodrug thereof in the pharmaceutical composition corresponds to about 1% w/w to about 50% w/w of the solids in the oral liquid formulation. In other embodiments, the amount of the pharmaceutically acceptable salt of iniparib correspond to about 1% w/w, about 1.1% w/w, about 1.2% w/w, about 1.3% w/w, about 1.4% w/w, about 1.5% w/w, about 1.6% w/w, about 1.7% w/w, about 1.8% w/w, about 1.9% w/w, about 2% w/w, about 2.1% w/w, about 2.2% w/w, about 2.3% w/w, about 2.4% w/w, about 2.5% w/w, about 2.6% w/w, about 2.7% w/w, about 2.8% w/w, about 2.9% w/w, about 3% w/w, about 3.1% w/w, about 3.2% w/w, about 3.3% w/w, about 3.4% w/w, about 3.5% w/w, about 3.6% w/w, about 3.7% w/w, about 3.8% w/w, about 3.9% w/w, about 4% w/w, about 4.1% w/w, about 4.2% w/w, about 4.3% w/w, about 4.4% w/w, about 4.5% w/w, about 4.6% w/w, about 4.7% w/w, about 4.8% w/w, about 4.9% w/w, about 5% w/w, about 5.1% w/w, about 5.2% w/w, about 5.3% w/w, about 5.4% w/w, about 5.5% w/w, about 5.6% w/w, about 5.7% w/w, about 5.8% w/w, about 5.9% w/w, about 6% w/w, about 6.1% w/w, about 6.2% w/w, about 6.3% w/w, about 6.4% w/w, about 6.5% w/w, about 6.6% w/w, about 6.7% w/w, about 6.8% w/w, about 6.9% w/w, about 7% w/w, about 7.1% w/w, about 7.2% w/w, about 7.3% w/w, about 7.4% w/w, about 7.5% w/w, about 7.6% w/w, about 7.7% w/w, about 7.8% w/w, about 7.9% w/w, about 8% w/w, about 8.1% w/w, about 8.2% w/w, about 8.3% w/w, about 8.4% w/w, about 8.5% w/w, about 8.6% w/w, about 8.7% w/w, about 8.8% w/w, about 8.9% w/w, about 9% w/w, about 9.1% w/w, about 9.2% w/w, about 9.3% w/w, about 9.4% w/w, about 9.5% w/w, about 9.6% w/w, about 9.7% w/w, about 9.8% w/w, about 9.9% w/w, about 10% w/w, about 10.2% w/w, about 10.4% w/w, about 10.6% w/w, about 10.8% w/w, about 11% w/w, about 11.2% w/w, about 11.4% w/w, about 11.6% w/w, about 11.8% w/w, about 12% w/w, about 12.2% w/w, about 12.4% w/w, about 12.6% w/w, about 12.8% w/w, about 13% w/w, about 13.2% w/w, about 13.4% w/w, about 13.6% w/w, about 13.8% w/w, about 14% w/w, about 14.2% w/w, about 14.4% w/w, about 14.6% w/w, about 14.8% w/w, about 15% w/w, about 15.5% w/w, about 16% w/w, about 16.5% w/w, about 17% w/w, about 17.5% w/w, about 18% w/w, about 18.5% w/w, about 19% w/w, about 19.5% w/w, about 20% w/w, about 21% w/w, about 22% w/w, about 23% w/w, about 24% w/w, about 25% w/w, about 26% w/w, about 27% w/w, about 28% w/w, about 29% w/w, about 30% w/w, about 31% w/w, about 32% w/w, about 33% w/w, about 34% w/w, about 35% w/w, about 36% w/w, about 37% w/w, about 38% w/w, about 39% w/w, about 40% w/w, about 41% w/w, about 42% w/w, about 43% w/w, about 44% w/w, about 45% w/w, about 46% w/w, about 47% w/w, about 48% w/w, about 49% w/w, or about 50% w/w of the solids in the oral liquid formulation.

Stability

The iniparib oral formulations described herein are stable in various storage conditions including refrigerated, ambient and accelerated conditions. Stable as used herein refers to iniparib oral formulations having about 95% or greater of the initial iniparib amount and about 5% w/w or less total impurities or related substances at the end of a given storage period. The percentage of impurities is calculated from the amount of impurities relative to the amount of iniparib. Stability is assessed by HPLC or any other known testing method. In some embodiments, the stable iniparib oral formulations have about 5% w/w, about 4% w/w, about 3% w/w, about 2.5% w/w, about 2% w/w, about 1.5% w/w, about 1% w/w, or about 0.5% w/w total impurities or related substances. In other embodiments, the stable iniparib oral formulations have about 5% w/w total impurities or related substances. In yet other embodiments, the stable iniparib oral formulations have about 4% w/w total impurities or related substances. In yet other embodiments, the stable iniparib oral formulations have about 3% w/w total impurities or related substances. In yet other embodiments, the stable iniparib oral formulations have about 2% w/w total impurities or related substances. In yet other embodiments, the stable iniparib oral formulations have about 1% w/w total impurities or related substances.

At refrigerated condition, the iniparib oral formulations described herein are stable for at least 1 month, at least 2 months, at least 3 months, at least 6 months, at least 9 months, at least 12 months, at least 15 months, at least 18 months, at least 24 months, at least 30 months and at least 36 months. In some embodiments, refrigerated condition is 5±5° C. In some embodiments, refrigerated condition is about 0° C., about 0.1° C., about 0.2° C., about 0.3° C., about 0.4° C., about 0.5° C., about 0.6° C., about 0.7° C., about 0.8° C., about 0.9° C., about 1° C., about 1.1° C., about 1.2° C., about 1.3° C., about 1.4° C., about 1.5° C., about 1.6° C., about 1.7° C., about 1.8° C., about 1.9° C., about 2° C., about 2.1° C., about 2.2° C., about 2.3° C., about 2.4° C., about 2.5° C., about 2.6° C., about 2.7° C., about 2.8° C., about 2.9° C., about 3° C., about 3.1° C., about 3.2° C., about 3.3° C., about 3.4° C., about 3.5° C., about 3.6° C., about 3.7° C., about 3.8° C., about 3.9° C., about 4° C., about 4.1° C., about 4.2° C., about 4.3° C., about 4.4° C., about 4.5° C., about 4.6° C., about 4.7° C., about 4.8° C., about 4.9° C., about 5° C., about 5.1° C., about 5.2° C., about 5.3° C., about 5.4° C., about 5.5° C., about 5.6° C., about 5.7° C., about 5.8° C., about 5.9° C., about 6° C., about 6.1° C., about 6.2° C., about 6.3° C., about 6.4° C., about 6.5° C., about 6.6° C., about 6.7° C., about 6.8° C., about 6.9° C., about 7° C., about 7.1° C., about 7.2° C., about 7.3° C., about 7.4° C., about 7.5° C., about 7.6° C., about 7.7° C., about 7.8° C., about 7.9° C., about 8° C., about 8.1° C., about 8.2° C., about 8.3° C., about 8.4° C., about 8.5° C., about 8.6° C., about 8.7° C., about 8.8° C., about 8.9° C., about 9° C., about 9.1° C., about 9.2° C., about 9.3° C., about 9.4° C., about 9.5° C., about 9.6° C., about 9.7° C., about 9.8° C., about 9.9° C., or about 10° C. At accelerated conditions, the iniparib oral formulations described herein are stable for at least 1 month, at least 2 months, at least 3 months, at least 4 months, at least 5 months, at least 6 months, at least 7 months, at least 8 months, at least 9 months, at least 10 months, at least 11 months, at least 12 months, at least 18 months, or at least 24 month. Accelerated conditions for the iniparib oral formulations described herein include temperatures that are at or above ambient levels (e.g. 25±5° C.). In some instances, an accelerated condition is at about 25° C., about 30° C., about 35° C., about 40° C., about 45° C., about 50° C., about 55° C., or about 60° C. Accelerated conditions for the iniparib oral formulations described herein also include relative humidity (RH) that are at or above ambient levels (55±10% RH). In other instances, an accelerated condition is above 55% RH, about 65% RH, about 70% RH, about 75% RH, or about 80% RH. In further instances, an accelerated condition is about 40° C. or 60° C. at ambient humidity. In yet further instances, an accelerated condition is about 40° C. at 75±5% RH humidity.

In some embodiments, the iniparib oral formulation is stable at about 5±5° C. to about 25±5° C. for at least 12 months. In one embodiment, the iniparib oral formulation is stable at about 5±5° C. for at least 12 months. In one embodiment, the iniparib oral formulation is stable at about 25±5° C. for at least 12 months. In one embodiment, the iniparib oral formulation is stable at about 5±5° C. for at least 24 months. In one embodiment, the iniparib oral formulation is stable at about 25±5° C. for at least 24 months.

Therapeutic Use of Formulations

In certain embodiments, also described herein are methods of treating a cancer with an iniparib formulation described supra. In some embodiments, described herein is a method of treating cancer in a subject in need thereof comprising administering to the subject in need thereof a therapeutically effective amount of:
(a) iniparib, or a pharmaceutically acceptable salt, solvate, metabolite, or prodrug thereof formulated as:
(A1) an oral solid formulation comprising:
(i) iniparib or a pharmaceutically acceptable salt, solvate, metabolite, or prodrug thereof;
(ii) at least one pharmaceutically acceptable excipient; and
(iii) optionally one or more agents selected from the group consisting of surfactants, preservatives, flavoring agents, sweetening agents, and antifoaming agents;
wherein median particle size of iniparib or a pharmaceutically acceptable salt, solvate, metabolite, or prodrug thereof is from about 20 µm to about 400 µm; and wherein the formulation is stable at about 5±5° C. to about 25±5° C. for at least 12 months;
(A2) an oral dosage form comprising an immediate-release top layer and a controlled-release core, wherein said immediate-release layer comprises at least one of the stimulant, antihistamine, or antiemetic; and the controlled-release layer comprising a therapeutically effective amount of a formulation, comprising:
(i) iniparib or a pharmaceutically acceptable salt, solvate, metabolite, or prodrug thereof;
(ii) at least one pharmaceutically acceptable excipient; and
(iii) optionally one or more agents selected from the group consisting of surfactants, preservatives, flavoring agents, sweetening agents, and antifoaming agents;
wherein median particle size of iniparib or a pharmaceutically acceptable salt, solvate, metabolite, or prodrug thereof is from about 20 µm to about 400 µm; and wherein the formulation is stable at about 5±5° C. to about 25±5° C. for at least 12 months;
(A3) an oral dosage form comprising an immediate-release top layer and a controlled-release core, wherein said immediate-release layer comprises at least one of the stimulant, antihistamine, or antiemetic; and the controlled-release layer comprising a therapeutically effective amount of a formulation, comprising:
(i) a pharmaceutically acceptable salt of iniparib or a solvate, metabolite, or prodrug thereof;
(ii) a buffer;
(iii) a surfactant;
(iv) water; and
(v) optionally one or more agents selected from the group consisting of preservatives, flavoring agents, sweetening agents, antifoaming agent, and suspensions aids;
wherein said formulation is an oral liquid formulation, and wherein said formulation is stable at about 5±5° C. to about 25±5° C. for at least 6 months;
(A4) a controlled-release iniparib formulation comprising a controlled-release matrix and from about 30 mg to about 400 mg of iniparib or a pharmaceutically acceptable salt, solvate, or prodrug thereof, wherein a median particle size of iniparib or a pharmaceutically acceptable salt, solvate, metabolite, or prodrug thereof is from about 20 µm to about 400 µm; and wherein said formulation provides a maximum mean blood concentration of iniparib of between about 200 ng/ml and about 6000 ng/ml upon oral administration to a subject in need thereof; or
(A5) an oral liquid formulation comprising
(i) a pharmaceutically acceptable salt of iniparib or a solvate, metabolite, or prodrug thereof;
(ii) a buffer;
(iii) a surfactant;
(iv) water; and
(v) optionally one or more agents selected from the group consisting of preservatives, flavoring agents, sweetening agents, antifoaming agent, and suspensions aids;
wherein said formulation is an oral liquid formulation, and
wherein said formulation is stable at about 5±5° C. to about 25±5° C. for at least 6 months;
(A6) an aqueous composition comprising a pharmaceutically acceptable salt of iniparib or a solvate, metabolite, or prodrug thereof, a pharmaceutically acceptable delivery vehicle, and a mucoadhesive agent, wherein the aqueous composition is formulated for transmucosal administration;

(b) about 0 mg/m² to about 90 mg/m² of temozolomide; and (c) optionally radiation.

In some embodiments, the cancer is a cancer described below. In some embodiments, the cancer is adrenal cortical cancer, anal cancer, aplastic anemia, bile duct cancer, bladder cancer, bone cancer, bone metastasis, Adult CNS brain tumors, Children CNS brain tumors, breast cancer, Castleman Disease, cervical cancer, Childhood Non-Hodgkin's lymphoma, colon and rectum (colorectal) cancer, endometrial cancer, esophagus cancer, Ewing's family of tumors, eye cancer, gallbladder cancer, gastrointestinal carcinoid tumors, gastrointestinal stromal tumors, gestational trophoblastic disease, glioblastoma multiforme, Hodgkin's disease, Kaposi's sarcoma, kidney cancer, laryngeal and hypopharyageal cancer, acute lymphocytic leukemia, acute myeloid leukemia, children's leukemia, chronic lymphocytic leukemia, chronic myeloid leukemia, liver cancer, lung cancer, lung carcinoid tumors, Non-Hodgkin's lymphoma, male breast cancer, malignant mesothelioma, multiple myeloma, myelodysplastic syndrome, nasal cavity and paranasal cancer, nasopharyngeal cancer, neuroblastoma, oral cavity and oropharyngeal cancer osteosarcoma, ovarian cancer, pancreatic cancer, penile cancer, pituitary tumor, prostate cancer, retinoblastoma, rhabdomyosarcona, salivary gland cancer, sarcoma (adult soft tissue cancer), melanoma skin cancer, non-melanoma skin cancer, stomach cancer, testicular cancer, thymus cancer, thyroid cancer, uterine sarcoma, vaginal cancer, vulvar cancer, Waldenstrom's macroglobulinemia, cancers of viral origin and virus-associated cancers. In some instances, the cancer is selected from the group consisting of breast cancer, colon cancer, glioblastoma multiforme, lung cancer, melanoma, ovarian cancer, prostate cancer, and transformed stem cells cancer. In some instances, the cancer is breast cancer. In some instances, the cancer is triple-negative breast cancer. In some instances, the cancer is ovarian cancer. In some instances, the cancer is glioblastoma.

In some embodiments, about 6 mg/kg to about 9 mg/kg of iniparib or a salt, solvate, metabolite, or prodrug thereof is administered to the subject. In some embodiments, about 7 mg/kg to about 8.6 mg/kg of iniparib or a salt, solvate, metabolite, or prodrug thereof is administered to the subject. In some embodiments, about 8 mg/kg to about 8.6 mg/kg of iniparib or a salt, solvate, metabolite, or prodrug thereof is administered to the subject. In some embodiments, about 8 mg/kg of iniparib or a salt, solvate, metabolite, or prodrug thereof is administered to the subject.

In some embodiments, the iniparib or a salt, solvate, metabolite, or prodrug thereof is administered to the subject once per day. In some embodiments, the iniparib or a salt, solvate, metabolite, or prodrug thereof is administered to the subject for about twice a week. In some embodiments, the iniparib or a salt, solvate, metabolite, or prodrug thereof is administered to the subject for about four, five or six weeks. In some embodiments, the iniparib or a salt, solvate, metabolite, or prodrug thereof is administered to the subject for about six weeks.

In some embodiments, about 70 mg/m² to about 80 mg/m² of temozolomide is administered to the subject. In some embodiments, about 75 mg/m² of temozolomide is administered to the subject. In some embodiments, about 0 mg/m² to about 70 mg/m² of temozolomide is administered to the subject. In some embodiments, about 5 mg/m2 of temozolomide is administered to the subject. In some embodiments, about 10 mg/m² of temozolomide is administered to the subject. In some embodiments, about 15 mg/m² of temozolomide is administered to the subject. In some embodiments, about 20 mg/m² of temozolomide is administered to the subject. In some embodiments, temozolomide is not administered to the subject.

In some embodiments, temozolomide is administered to the subject daily. In some embodiments, temozolomide is administered to the subject for about four, five or six weeks. In some embodiments, temozolomide is administered to the subject for about six weeks.

In some embodiments, about 60 Gy of radiation is administered to the subject over the course of about four, five, or six weeks. In some embodiments, about 60 Gy of radiation is administered to the subject over the course of about six weeks.

In some embodiments, upon completion of about six weeks of treatment with a combination of iniparib or a salt, solvate, metabolite, or prodrug thereof, temozolomide and radiation, the subject receives a treatment break of about four weeks.

In some embodiments, the method further comprises a maintenance regimen.

In some embodiments, the maintenance regimen comprises about 8.6 mg/kg of iniparib or a salt, solvate, metabolite, or prodrug thereof, and about 150 mg/m² to about 200 mg/m² of temozolomide.

In some embodiments, the iniparib or a salt, solvate, metabolite, or prodrug thereof is administered to the subject once per day. In some embodiments, the iniparib or a salt, solvate, metabolite, or prodrug thereof is administered to the subject for about twice a week.

In some embodiments, the iniparib or a salt, solvate, metabolite, or prodrug thereof is administered to the subject for about 1-6 cycles. In some embodiments, the temozolomide is administered to the subject on days 1-5 of each cycle. In some embodiments, the temozolomide is administered to the subject for about 1-6 cycles.

In some embodiments, the subject is an adult. In some embodiments, the subject is elderly. In some embodiments, the subject is a child.

In some embodiments, iniparib, or a pharmaceutically acceptable salt, solvate, metabolite, or prodrug thereof is administered to the subject in a fasted state. In some embodiments, iniparib, or a pharmaceutically acceptable salt, solvate, metabolite, or prodrug thereof is administered to the subject in a fed state.

In some embodiments, iniparib, or a pharmaceutically acceptable salt, solvate, metabolite, or prodrug thereof is administered in combination with an additional agent selected from the group consisting of anticancer agents, stimulants, antiemetics, antihistamine, or a combination thereof.

In some embodiments, the anticancer agent is selected from the group consisting of gemcitabine, carboplatin, paclitaxel, irinotecan, topotecan, temozolomide, picropodophyllin, and gefitinib.

In some embodiments, the stimulant is selected from the group consisting of aminophylline, caffeine, dyphlline, oxitriphylline, theophhylline, amphetamine, benzphetamine, dextroamphetamine, diethylpropion, mazindol, methamphetamine, methylphenidate, dexmethylphenidate, pemoline, sibutramine, modafinil, atomoxetine, phendimetrizine, phenteramine, adrafinil, phenylpropanolamine, psuedoephedrine, synephrine, amphetaminil, furfenorex, or a combination thereof.

In some embodiments, the antiemetic is selected from the group consisting of aprepitant, dronabinol, perphenazine, palonosetron, trimethobenzamide, metoclopromide, domperidone, prochlorperazine, promethazine, chlorpromazine, trimethobenzamide, ondansetron, granisetron, hydroxyzine, acetylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxyperndyl, pipamazine, scopolamine, sulpiride, tetrahydrocannabinol, thiethylperazine, thioproperazine, tropisetron, droperidol, haloperidol, prochloperazine, metoclopramide, diphenhydramine, *cannabis*, midazolam, lorazepam, hyoscine, dexamethasone, emetrol, propofol and mixtures thereof.

In some embodiments, the antihistamine is selected from the group consisting of 2-(m-fluorophenyl)-histamine, chlorpheniramine, mepyramine, terfenadine, astemizole, tripolidine, ethanolamines carbinoxamine, diphenhydramine, doxylamine, pyrilamine, tripelennamine, hydroxyzine, fexofenadine, brompheniramine chlorpheniramine, cyproheptadine, loratadine, cetirizine, dimaprit, impromidine, amthamine, cimetidine, ranitidine, nizatidine, famotidine, R-alpha-methylhistamine, imetit, immepip, thioperamide, iodophenpropit, clobenpropit, clobenpropit, imetit, clozapine, thioperamide, azelastine, brompheniramine, carbinoxamine, cetrizine, chlorpheniramine, clemastine, cyclizine, cyproheptadine, desloratidine, dimenhydrinate, diphenhydramine, emedastine, fexofenadine, ketotifen, levocabastine, loratadine, meclizine, olopatadine, phenindamine, promethazine, or a combination thereof.

Breast Cancer

In one aspect, the pharmaceutical compositions disclosed herein provide a method of treating breast cancer. Several types of breast cancer exist that might be treated by the methods provided herein. A lobular carcinoma in situ and a ductal carcinoma in situ are breast cancers that have developed in the lobules and ducts, respectively, but have not spread to the fatty tissue surrounding the breast or to other areas of the body. An infiltrating (or invasive) lobular and a ductal carcinoma are cancers that have developed in the lobules and ducts, respectively, and have spread to either the breast's fatty tissue and/or other parts of the body. Other cancers of the breast that would benefit from treatment by the methods provided herein are medullary carcinomas, colloid carcinomas, tubular carcinomas, and inflammatory breast cancer. In some instances, the breast cancer is a triple-negative breast cancer.

Treatments available for breast cancer patients are surgery, immunotherapy, radiation therapy, chemotherapy, endocrine therapy, or a combination thereof. A lumpectomy and a mastectomy are two possible surgical procedures available for breast cancer patients.

Chemotherapy utilizes anti-tumor agents to prevent cancer cells from multiplying, invading, metastasizing and killing a patient. Several drugs are available to treat breast cancer, including cytotoxic drugs such as doxorubicin, cyclophosphamide, methotrexate, paclitaxel, thiotepa, mitoxantrone, vincristine, or combinations thereof. Endocrine therapy might be an effective treatment where the remaining breast tissue retains endocrine sensitivity. Agents administered for this therapy include tamoxifer, megestrol acetate, aminoglutethimide, fluoxymesterone, leuprolide, goserelin, and prednisone.

In some embodiments, described herein is a method of treating a breast cancer comprising administering to a subject in need thereof an oral solid formulation comprising an iniparib active ingredient; an oral dosage form comprising an immediate-release top layer and a controlled-release core, in which the controlled-release layer comprises an iniparib active ingredient, and in which the oral dosage form is in either a solid or a liquid form; an oral liquid formulation comprising an iniparib active ingredient; and an aerosol formulation comprising an iniparib active ingredient. In some instances, the method further comprises administration of iniparib in combination with, e.g., surgery, radiation therapy, chemotherapy, or endocrine therapy.

Ovarian Cancer

In another aspect, provided herein is a method of treating ovarian cancer, including epithelial ovarian tumors. Preferably, provided herein is a method of treating an ovarian cancer selected from the following: an adenocarcinoma in the ovary and an adenocarcinoma that has migrated from the ovary into the abdominal cavity. Surgery, immunotherapy, chemotherapy, hormone therapy, radiation therapy, or a combination thereof are some possible treatments available for ovarian cancer. Some possible surgical procedures include debulking, and a unilateral or bilateral oophorectomy and/or a unilateral or bilateral salpigectomy.

Anti-cancer drugs that might be used include cyclophosphamide, etoposide, altretamine, and ifosfamide. Hormone therapy with the drug tamoxifen might be used to shrink ovarian tumors. Radiation therapy might be external beam radiation therapy and/or brachytherapy.

In some embodiments, described herein is a method of treating an ovarian cancer comprising administering to a subject in need thereof an oral solid formulation comprising an iniparib active ingredient; an oral dosage form comprising an immediate-release top layer and a controlled-release core, in which the controlled-release layer comprises an iniparib active ingredient, and in which the oral dosage form is in either a solid or a liquid form; an oral liquid formulation comprising an iniparib active ingredient; and an aerosol formulation comprising an iniparib active ingredient. In some instances, the method further comprises administration of iniparib in combination with, e.g., surgery, radiation therapy, chemotherapy endocrine therapy, or a combination thereof.

Cervical Cancer

In another aspect, disclosed herein is a method of treating cervical cancer, preferably an adenocarcinoma in the cervix epithelial. Two main types of this cancer exist: squamous cell carcinoma and adenocarcinomas. The former constitutes about 80-90% of all cervical cancers and develops where the ectocervix (portion closest to the vagina) and the endocervix (portion closest to the uterus) join. The latter develop in the mucous-producing gland cells of the endocervix. Some cervical cancers have characteristics of both of these and are called adenosquamous carcinomas or mixed carcinomas.

The chief treatments available for cervical cancer are surgery, immunotherapy, radiation therapy and chemotherapy. Some possible surgical options are cryosurgery, a hysterectomy, and a radical hysterectomy. Radiation therapy for cervical cancer patients includes external beam radiation therapy or brachytherapy. Anti-cancer drugs that might be administered as part of chemotherapy to treat cervical cancer include cisplatin, carboplatin, hydroxyurea, irinotecan, bleomycin, vincristine, mitomycin, ifosfamide, fluorouracil, etoposide, methotrexate, and combinations thereof.

In some embodiments, described herein is a method of treating a cervical cancer comprising administering to a subject in need thereof an oral solid formulation comprising an iniparib active ingredient; an oral dosage form comprising an immediate-release top layer and a controlled-release core, in which the controlled-release layer comprises an iniparib active ingredient, and in which the oral dosage form is in either a solid or a liquid form; an oral liquid formulation comprising an iniparib active ingredient; and an aerosol formulation comprising an iniparib active ingredient. In some instances, the method further comprises administration of iniparib in combination with, e.g., surgery, radiation therapy, chemotherapy, or a combination thereof.

Prostate Cancer

In one other aspect, disclosed herein are methods to treat prostate cancer, preferably a prostate cancer selected from the following: an adenocarcinoma or an adenocarcinoma that has migrated to the bone. Prostate cancer develops in the prostate organ in men, which surrounds the first part of the urethra. The prostate has several cell types but 99% of tumors are adenocarcinomas that develop in the glandular cells responsible for generating seminal fluid.

Surgery, immunotherapy, radiation therapy, cryosurgery, hormone therapy, and chemotherapy are some treatments available for prostate cancer patients. Possible surgical procedures to treat prostate cancer include radical retropubic prostatectomy, a radical perineal prostatectomy, and a laparoscopic radical prostatectomy. Some radiation therapy options are external beam radiation, including three dimensional conformal radiation therapy, intensity modulated radiation therapy, and conformal proton beam radiation therapy. Brachytherapy (seed implantation or interstitial radiation therapy) is also an available method of treatment for prostate cancer. Cryosurgery is another possible method used to treat localized prostate cancer cells.

Hormone therapy, also called androgen deprivation therapy or androgen suppression therapy, might be used to treat prostate cancer. Several methods of this therapy are available including an orchiectomy in which the testicles, where 90% of androgens are produced, are removed. Another method is the administration of luteinizing hormone-releasing hormone (LHRH) analogs to lower androgen levels. The LHRH analogs available include leuprolide, goserelin, triptorelin, and histrelin. An LHRH antagonist might also be administered, such as abarelix.

Treatment with an anti-androgen agent, which blocks androgen activity in the body, is another available therapy. Such agents include flutamide, bicalutamide, and nilutamide. This therapy is typically combined with LHRH analog administration or an orchiectomy, which is termed a combined androgen blockade (CAB).

Chemotherapy might be appropriate where a prostate tumor has spread outside the prostate gland and hormone treatment is not effective. Anti-cancer drugs such as doxorubicin, estramustine, etoposide, mitoxantrone, vinblastine, paclitaxel, docetaxel, carboplatin, and prednisone might be administered to slow the growth of prostate cancer, reduce symptoms and improve the quality of life.

In some embodiments, described herein is a method of treating a prostate cancer comprising administering to a subject in need thereof an oral solid formulation comprising an iniparib active ingredient; an oral dosage form comprising an immediate-release top layer and a controlled-release core, in which the controlled-release layer comprises an iniparib active ingredient, and in which the oral dosage form is in either a solid or a liquid form; an oral liquid formulation comprising an iniparib active ingredient; and an aerosol formulation comprising an iniparib active ingredient. In some instances, the method further comprises administration of iniparib in combination with, e.g., surgery, radiation therapy, chemotherapy, hormone therapy, or a combination thereof.

Pancreatic Cancer

Some embodiments provide methods of treating pancreatic cancer, preferably a pancreatic cancer selected from the following: an epitheliod carcinoma in the pancreatic duct tissue and an adenocarcinoma in a pancreatic duct.

The most common type of pancreatic cancer is an adenocarcinoma, which occurs in the lining of the pancreatic duct. The possible treatments available for pancreatic cancer are surgery, immunotherapy, radiation therapy, and chemotherapy. Possible surgical treatment options include a distal or total pancreatectomy and a pancreaticoduodenectomy (Whipple procedure).

Radiation therapy might be an option for pancreatic cancer patients, specifically external beam radiation where radiation is focused on the tumor by a machine outside the body. Another option is intraoperative electron beam radiation administered during an operation.

Chemotherapy might be used to treat pancreatic cancer patients. Appropriate anti-cancer drugs include 5-fluorouracil (5-FU), mitomycin, ifosfamide, doxorubicin, streptozocin, chlorozotocin, and combinations thereof.

In some embodiments, described herein is a method of treating a pancreatic cancer comprising administering to a subject in need thereof an oral solid formulation comprising an iniparib active ingredient; an oral dosage form comprising an immediate-release top layer and a controlled-release core, in which the controlled-release layer comprises an iniparib active ingredient, and in which the oral dosage form is in either a solid or a liquid form; an oral liquid formulation comprising an iniparib active ingredient; and an aerosol formulation comprising an iniparib active ingredient. In some instances, the method further comprises administration of iniparib in combination with, e.g., surgery, radiation therapy, or chemotherapy.

Bladder Cancer

Some embodiments provide methods of treating bladder cancer, preferably a transitional cell carcinoma in urinary bladder. Bladder cancers are urothelial carcinomas (transitional cell carcinomas) or tumors in the urothelial cells that line the bladder. The remaining cases of bladder cancer are squamous cell carcinomas, adenocarcinomas, and small cell cancers. Several subtypes of urothelial carcinomas exist depending on whether they are noninvasive or invasive and whether they are papillary, or flat. Noninvasive tumors are in the urothelium, the innermost layer of the bladder, while invasive tumors have spread from the urothelium to deeper layers of the bladder's main muscle wall. Invasive papillary urothelial carcinomas are slender finger-like projections that branch into the hollow center of the bladder and also grow outward into the bladder wall. Non-invasive papillary urothelial tumors grow towards the center of the bladder. While a non-invasive, flat urothelial tumor (also called a flat carcinoma in situ) is confined to the layer of cells closest to the inside hollow part of the bladder, an invasive flat urothelial carcinoma invades the deeper layer of the bladder, particularly the muscle layer.

To treat bladder cancer, surgery, radiation therapy, immunotherapy, chemotherapy, or a combination thereof might be applied. Some possible surgical options are a transurethral resection, a cystectomy, or a radical cystectomy. Radiation therapy for bladder cancer might include external beam radiation and brachytherapy.

Immunotherapy is another method that might be used to treat a bladder cancer patient. Typically this is accomplished intravesically, which is the administration of a treatment agent directly into the bladder by way of a catheter. One method is *Bacillus* Calmete-Guerin (BCG) where a bacterium sometimes used in tuberculosis vaccination is given directly to the bladder through a catheter. The body mounts an immune response to the bacterium, thereby attacking and killing the cancer cells.

Another method of immunotherapy is the administration of interferons, glycoproteins that modulate the immune response. Interferon alpha is often used to treat bladder cancer.

Anti-cancer drugs that nay be used in chemotherapy to treat bladder cancer include thitepa, methotrexate, vinblastine, doxorubicin, cyclophosphamide, paclitaxel, carboplatin, cisplatin, ifosfamide, gemcitabine, or combinations thereof.

In some embodiments, described herein is a method of treating a bladder cancer comprising administering to a subject in need thereof an oral solid formulation comprising an iniparib active ingredient; an oral dosage form comprising an immediate-release top layer and a controlled-release core, in which the controlled-release layer comprises an iniparib active ingredient, and in which the oral dosage form is in either a solid or a liquid form; an oral liquid formulation comprising an iniparib active ingredient; and an aerosol formulation comprising an iniparib active ingredient. In some instances, the method further comprises administration of iniparib in combination with, e.g., surgery, radiation therapy, immunotherapy, chemotherapy, or a combination thereof.

Acute Myeloid Leukemia

Some embodiments provide methods of treating acute myeloid leukemia (AML), preferably acute promyelocytic leukemia (APL) in peripheral blood. AML begins in the bone marrow but can spread to other parts of the body including the lymph nodes, liver, spleen, central nervous system, and testes. It is acute meaning it develops quickly and might be fatal if not treated within a few months. AML is characterized by immature bone marrow cells usually granulocytes or monocytes, which continue to reproduce and accumulate.

AML might be treated by immunotherapy, radiation therapy, chemotherapy, bone marrow or peripheral blood stem cell transplantation, or a combination thereof. Radiation therapy includes external beam radiation and might have side effects. Anti-cancer drugs that might be used in chemotherapy to treat AML include cytarabine, anthracycline, anthracenedione, idarubicin, daunorubicin, idarubicin, mitoxantrone, thioguanine, vincristine, prednisone, etoposide, or a combination thereof.

Monoclonal antibody therapy might be used to treat AML patients. Small molecules or radioactive chemicals might be attached to these antibodies before administration to a patient in order to provide a means of killing leukemia cells in the body. The monoclonal antibody, gemtuzumab ozogamicin, which binds CD33 on AML cells, might be used to treat AML patients unable to tolerate prior chemotherapy regimens.

Bone marrow or peripheral blood stem cell transplantation might be used to treat AML patients. Some possible transplantation procedures are an allogenic or an autologous transplant.

In some embodiments, described herein is a method of treating a leukemia cancer comprising administering to a subject in need thereof an oral solid formulation comprising an iniparib active ingredient; an oral dosage form comprising an immediate-release top layer and a controlled-release core, in which the controlled-release layer comprises an iniparib active ingredient, and in which the oral dosage form is in either a solid or a liquid form; an oral liquid formulation comprising an iniparib active ingredient; and an aerosol formulation comprising an iniparib active ingredient. In some instances, the method further comprises administration of iniparib in combination with, e.g., surgery, radiation therapy, chemotherapy, or transplantation therapy.

In some embodiments, also described herein is a method of treating a leukemia subtype, e.g., Acute Lymphocytic Leukemia, Acute Myeloid Leukemia, Chronic Lymphocytic Leukemia, Chronic Myeloid Leukemia, Hairy Cell Leukemia, Myelodysplasia, and Myeloproliferative Disorders, comprising administering to a subject in need thereof an oral solid formulation comprising an iniparib active ingredient; an oral dosage form comprising an immediate-release top layer and a controlled-release core, in which the controlled-release layer comprises an iniparib active ingredient, and in which the oral dosage form is in either a solid or a liquid form; an oral liquid formulation comprising an iniparib active ingredient; and an aerosol formulation comprising an iniparib active ingredient.

Lung Cancer

Some embodiments provide methods to treat lung cancer. The most common type of lung cancer is non-small cell lung cancer (NSCLC), which accounts for approximately 80-85% of lung cancers and is divided into squamous cell carcinomas, adenocarcinomas, and large cell undifferentiated carcinomas. Small cell lung cancer accounts for 15-20% of lung cancers.

Treatment options for lung cancer include surgery, immunotherapy, radiation therapy, chemotherapy, photodynamic therapy, or a combination thereof. Some possible surgical options for treatment of lung cancer are a segmental or wedge resection, a lobectomy, or a pneumonectomy. Radiation therapy might be external beam radiation therapy or brachytherapy.

Some anti-cancer drugs that might be used in chemotherapy to treat lung cancer include cisplatin, carboplatin, paclitaxel, docetaxel, gemcitabine, vinorelbine, irinotecan, etoposide, vinblastine, gefitinib, ifosfamide, methotrexate, or a combination thereof. Photodynamic therapy (PDT) might be used to treat lung cancer patients.

In some embodiments, described herein is a method of treating a lung cancer comprising administering to a subject in need thereof an oral solid formulation comprising an iniparib active ingredient; an oral dosage form comprising an immediate-release top layer and a controlled-release core, in which the controlled-release layer comprises an iniparib active ingredient, and in which the oral dosage form is in either a solid or a liquid form; an oral liquid formulation comprising an iniparib active ingredient; and an aerosol formulation comprising an iniparib active ingredient. In some instances, the method further comprises administration of iniparib in combination with, e.g., surgery, radiation therapy, chemotherapy, photodynamic therapy, or a combination thereof.

Skin Cancer

Some embodiments provide methods of treating skin cancer. There are several types of cancer that start in the skin. The most common types are basal cell carcinoma and squamous cell carcinoma, which are non-melanoma skin cancers. Actinic keratosis is a skin condition that sometimes develops into squamous cell carcinoma. Non-melanoma skin cancers rarely spread to other parts of the body. Melanoma, the rarest form of skin cancer, is more likely to invade nearby tissues and spread to other parts of the body. Different types of treatment are available for patients with non-melanoma and melanoma skin cancer and actinic keratosis including surgery, radiation therapy, chemotherapy and photodynamic therapy. Some possible surgical options for treatment of skin cancer are mohs micrographic surgery, simple excision, electrodessication and curettage, cryosurgery, laser surgery. Radiation therapy might be external beam radiation therapy or brachytherapy. Other types of treatments that are being tested in clinical trials are biologic therapy or immunotherapy, chemoimmunotherapy, topical chemotherapy with fluorouracil and photodynamic therapy.

In some embodiments, described herein is a method of treating a skin cancer comprising administering to a subject in need thereof an oral solid formulation comprising an iniparib active ingredient; an oral dosage form comprising an immediate-release top layer and a controlled-release core, in which the controlled-release layer comprises an iniparib active ingredient, and in which the oral dosage form is in either a solid or a liquid form; an oral liquid formulation comprising an iniparib active ingredient; and an aerosol formulation comprising an iniparib active ingredient. In some instances, the method further comprises iniparib in combination with, e.g., surgery, radiation therapy, chemotherapy, photodynamic therapy, or a combination thereof.

Eye Cancer, Retinoblastoma

Some embodiments provide methods to treat eye retinoblastoma. Retinoblastoma is a malignant tumor of the retina. Although retinoblastoma might occur at any age, it most often occurs in younger children, usually before the age of 5 years. The tumor might be in one eye only or in both eyes. Retinoblastoma is usually confined to the eye and does not spread to nearby tissue or other parts of the body. Treatment options that attempt to cure the patient and preserve vision include enucleation (surgery to remove the eye), radiation therapy, cryotherapy, photocoagulation, immunotherapy, thermotherapy and chemotherapy. Radiation therapy might be external beam radiation therapy or brachytherapy.

In some embodiments, described herein is a method of treating retinoblastoma comprising administering to a subject in need thereof an oral solid formulation comprising an iniparib active ingredient; an oral dosage form comprising an immediate-release top layer and a controlled-release core, in which the controlled-release layer comprises an iniparib active ingredient, and in which the oral dosage form is in either a solid or a liquid form; an oral liquid formulation comprising an iniparib active ingredient; and an aerosol formulation comprising an iniparib active ingredient. In some instances, the method further comprises administration of iniparib in combination with, e.g., surgery, radiation therapy, cryotherapy, photocoagulation, thermotherapy and chemotherapy, or a combination thereof.

Eye Cancer, Intraocular Melanoma

Some embodiments provide methods to treat intraocular (eye) melanoma. Intraocular melanoma, a rare cancer, is a disease in which cancer cells are found in the part of the eye called the uvea. The uvea includes the iris, the ciliary body, and the choroid. Intraocular melanoma occurs most often in people who are middle aged. Treatments for intraocular melanoma include surgery, immunotherapy, radiation therapy and laser therapy. Surgery is the most common treatment of intraocular melanoma. Some possible surgical options are iridectomy, iridotrabeculectomy, iridocyclectomy, choroidectomy, enucleation and orbital exenteration. Radiation therapy might be external beam radiation therapy or brachytherapy. Laser therapy might be an intensely powerful beam of light to destroy the tumor, thermotherapy or photocoagulation.

In some embodiments, described herein is a method of treating intraocular melanoma comprising administering to a subject in need thereof an oral solid formulation comprising an iniparib active ingredient; an oral dosage form comprising an immediate-release top layer and a controlled-release core, in which the controlled-release layer comprises an iniparib active ingredient, and in which the oral dosage form is in either a solid or a liquid form; an oral liquid formulation comprising an iniparib active ingredient; and an aerosol formulation comprising an iniparib active ingredient. In some instances, the method further comprises administration of iniparib in combination with, e.g., surgery, radiation therapy and laser therapy, or a combination thereof.

Endometrium Cancer

Some embodiments provide methods of treating endometrium cancer. Endometrial cancer is a cancer that starts in the endometrium, the inner lining of the uterus. Some of the examples of the cancer of uterus and endometrium include, but are not limited to, adenocarcinomas, adenoacanthomas, adenosquamous carcinomas, papillary serous adenocarcinomas, clear cell adenocarcinomas, uterine sarcomas, stromal sarcomas, malignant mixed mesodermal tumors, and leiomyosarcomas.

In some embodiments, described herein is a method of treating an endometrium cancer comprising administering to a subject in need thereof an oral solid formulation comprising an iniparib active ingredient; an oral dosage form comprising an immediate-release top layer and a controlled-release core, in which the controlled-release layer comprises an iniparib active ingredient, and in which the oral dosage form is in either a solid or a liquid form; an oral liquid formulation comprising an iniparib active ingredient; and an aerosol formulation comprising an iniparib active ingredient. In some instances, the method further comprises administration of iniparib in combination with, e.g., surgery, radiation therapy, chemotherapy, gene therapy, photodynamic therapy, antiangiogenesis therapy, and immunotherapy, or a combination thereof.

Liver Cancer

Some embodiments provide methods to treat primary liver cancer (cancer that begins in the liver). Primary liver cancer can occur in both adults and children. Different types of treatments are available for patients with primary liver cancer. These include surgery, immunotherapy, radiation therapy, chemotherapy and percutaneous ethanol injection. The types of surgery that might be used are cryosurgery, partial hepatectomy, total hepatectomy and radiofrequency ablation. Radiation therapy might be external beam radiation therapy, brachytherapy, radiosensitizers or radiolabel antibodies. Other types of treatment include hyperthermia therapy and immunotherapy.

In some embodiments, described herein is a method of treating a liver cancer comprising administering to a subject in need thereof an oral solid formulation comprising an iniparib active ingredient; an oral dosage form comprising an immediate-release top layer and a controlled-release core, in which the controlled-release layer comprises an iniparib active ingredient, and in which the oral dosage form is in either a solid or a liquid form; an oral liquid formulation comprising an iniparib active ingredient; and an aerosol formulation comprising an iniparib active ingredient. In some instances, the method further comprises administration of iniparib in combination with, e.g., surgery, radiation therapy, chemotherapy, percutaneous ethanol injection, hyperthermia therapy and immunotherapy, or a combination thereof.

Kidney Cancer

Some embodiments provide methods to treat kidney cancer. Kidney cancer (also called renal cell cancer or renal adenocarcinoma) is a disease in which malignant cells are found in the lining of tubules in the kidney. Kidney cancer might be treated by surgery, radiation therapy, chemotherapy and immunotherapy. Some possible surgical options to treat kidney cancer are partial nephrectomy, simple nephrectomy and radical nephrectomy. Radiation therapy might be external beam radiation therapy or brachytherapy. Stem cell transplant might be used to treat kidney cancer.

In some embodiments, described herein is a method of treating a kidney cancer comprising administering to a subject in need thereof an oral solid formulation comprising an iniparib active ingredient; an oral dosage form comprising an immediate-release top layer and a controlled-release core, in which the controlled-release layer comprises an iniparib active ingredient, and in which the oral dosage form is in either a solid or a liquid form; an oral liquid formulation comprising an iniparib active ingredient; and an aerosol formulation comprising an iniparib active ingredient. In some instances, the method further comprises administration of iniparib in combination with, e.g., surgery, radiation therapy, chemotherapy, immunotherapy and stem cell transplant, or a combination thereof.

Thyroid Cancer

Some embodiments provide methods of treating thyroid cancer. Thyroid cancer is a disease in which cancer (malignant) cells are found in the tissues of the thyroid gland. The four main types of thyroid cancer are papillary, follicular, medullary and anaplastic. Thyroid cancer might be treated by surgery, immunotherapy, radiation therapy, hormone therapy and chemotherapy. Surgery is the most common treatment of thyroid cancer. Some possible surgical options for treatment of thyroid cancer are lobectomy, near-total thyroidectomy, total thyroidectomy and lymph node dissection. Radiation therapy might be external radiation therapy or might require intake of a liquid that contains radioactive iodine. Hormone therapy uses hormones to stop cancer cells from growing. In treating thyroid cancer, hormones might be used to stop the body from making other hormones that might make cancer cells grow.

In some embodiments, described herein is a method of treating a thyroid cancer comprising administering to a subject in need thereof an oral solid formulation comprising an iniparib active ingredient; an oral dosage form comprising an immediate-release top layer and a controlled-release core, in which the controlled-release layer comprises an iniparib active ingredient, and in which the oral dosage form is in either a solid or a liquid form; an oral liquid formulation comprising an iniparib active ingredient; and an aerosol formulation comprising an iniparib active ingredient. In some instances, the method further comprises administration of iniparib in combination with, e.g., surgery, surgery, radiation therapy, hormone therapy and chemotherapy, or a combination thereof.

AIDS Related Cancer

Some embodiments provide methods of treating AIDS-related lymphoma. AIDS-related lymphoma is a disease in which malignant cells form in the lymph system of patients who have acquired immunodeficiency syndrome (AIDS). AIDS is caused by the human immunodeficiency virus (HIV), which attacks and weakens the body's immune system. The immune system is then unable to fight infection and diseases that invade the body. People with HIV disease have an increased risk of developing infections, lymphoma, and other types of cancer. Lymphomas are cancers that affect the white blood cells of the lymph system. Lymphomas are divided into two general types: Hodgkin's lymphoma and non-Hodgkin's lymphoma. Both Hodgkin's lymphoma and non-Hodgkin's lymphoma might occur in AIDS patients, but non-Hodgkin's lymphoma is more common. When a person with AIDS has non-Hodgkin's lymphoma, it is called an AIDS-related lymphoma. Non-Hodgkin's lymphomas might be indolent (slow-growing) or aggressive (fast-growing). AIDS-related lymphoma is usually aggressive. The three main types of AIDS-related lymphoma are diffuse large B-cell lymphoma, B-cell immunoblastic lymphoma and small non-cleaved cell lymphoma.

Treatment of AIDS-related lymphoma combines treatment of the lymphoma with treatment for AIDS. Patients with AIDS have weakened immune systems and treatment can cause further damage. For this reason, patients who have AIDS-related lymphoma are usually treated with lower doses of drugs than lymphoma patients who do not have AIDS. Highly-active antiretroviral therapy (HAART) is used to slow progression of HIV. Medicine to prevent and treat infections, which can be serious, is also used. AIDS-related lymphomas might be treated by chemotherapy, immunotherapy, radiation therapy, and high-dose chemotherapy with stem cell transplant. Radiation therapy might be external beam radiation therapy or brachytherapy. AIDS-related lymphomas can be treated by monoclonal antibody therapy.

In some embodiments, described herein is a method of treating an AIDS-related lymphoma comprising administering to a subject in need thereof an oral solid formulation comprising an iniparib active ingredient; an oral dosage form comprising an immediate-release top layer and a controlled-release core, in which the controlled-release layer comprises an iniparib active ingredient, and in which the oral dosage form is in either a solid or a liquid form; an oral liquid formulation comprising an iniparib active ingredient; and an aerosol formulation comprising an iniparib active ingredient. In some instances, the method further comprises administration of iniparib in combination with, e.g., chemotherapy, radiation therapy and high-dose chemotherapy, or a combination thereof.

Kaposi's Sarcoma

Some embodiments provide methods of treating Kaposi's sarcoma. Kaposi's sarcoma is a disease in which cancer cells are found in the tissues under the skin or mucous membranes that line the mouth, nose, and anus. Classic Kaposi's sarcoma usually occurs in older men of Jewish, Italian, or Mediterranean heritage. This type of Kaposi's sarcoma progresses slowly, sometimes over 10 to 15 years. Kaposi's sarcoma might occur in people who are taking immunosuppressants. Kaposi's sarcoma in patients who have Acquired Immunodeficiency Syndrome (AIDS) is called epidemic Kaposi's sarcoma. Kaposi's sarcoma in people with AIDS usually spreads more quickly than other kinds of Kaposi's sarcoma and often is found in many parts of the body. Kaposi's sarcoma might be treated with surgery, chemotherapy, radiation therapy and immunotherapy. External radiation therapy is a common treatment of Kaposi's sarcoma. Some possible surgical options to treat Kaposi's Sarcoma are local excision, electrodessication and curettage, and cryotherapy.

In some embodiments, described herein is a method of treating Kaposi's sarcoma comprising administering to a subject in need thereof an oral solid formulation comprising an iniparib active ingredient; an oral dosage form comprising an immediate-release top layer and a controlled-release core, in which the controlled-release layer comprises an iniparib active ingredient, and in which the oral dosage form is in either a solid or a liquid form; an oral liquid formulation comprising an iniparib active ingredient; and an aerosol formulation comprising an iniparib active ingredient. In some instances, the method further comprises administration of iniparib in combination with, e.g., surgery, chemotherapy, radiation therapy and immunotherapy, or a combination thereof.

Viral-Induced Cancers

Some embodiments provide methods of treating viral-induced cancers. Several common viruses are clearly or probable causal factors in the etiology of specific malignancies. These viruses either normally establish latency or few can become persistent infections. Oncogenesis is probably linked to an enhanced level of viral activation in the infected host, reflecting heavy viral dose or compromised immune control. The major virus-malignancy systems include hepatitis B virus (HBV), hepatitis C virus (HCV), and hepatocellular carcinoma; human lymphotropic virus-type 1 (HTLV-1) and adult T-cell leukemia/lymphoma; and human papilloma virus (HPV) and cervical cancer. In general, these malignancies occur relatively early in life, typically peaking in middle-age or earlier.

Virus-Induced Hepatocellular Carcinoma

The causal relationship between both HBV aid HCV and hepatocellular carcinoma or liver cancer is established through substantial epidemiologic evidence. Both appear to act via chronic replication in the liver by causing cell death and subsequent regeneration. Different types of treatments are available for patients with liver cancer. These include surgery, immunotherapy, radiation therapy, chemotherapy and percutaneous ethanol injection. The types of surgery that might be used are cryosurgery, partial hepatectomy, total hepatectomy and radiofrequency ablation. Radiation therapy might be external beam radiation therapy, brachytherapy, radiosensitizers or radiolabel antibodies. Other types of treatment include hyperthermia therapy and immunotherapy.

In some embodiments, described herein is a method of treating a virus-induced hepatocellular carcinoma comprising administering to a subject in need thereof an oral solid formulation comprising an iniparib active ingredient; an oral dosage form comprising an immediate-release top layer and a controlled-release core, in which the controlled-release layer comprises an iniparib active ingredient, and in which the oral dosage form is in either a solid or a liquid form; an oral liquid formulation comprising an iniparib active ingredient; and an aerosol formulation comprising an iniparib active ingredient. In some instances, the method further comprises administration of iniparib in combination with, e.g., surgery, radiation therapy, chemotherapy, percutaneous ethanol injection, hyperthermia therapy and immunotherapy, or a combination thereof.

Viral-Induced Adult T Cell Leukemia/Lymphoma

The association between HTLV-1 and Adult T cell leukemia (ATL) is firmly established. Unlike the other oncogenic viruses found throughout the world, HTLV-1 is highly geographically restricted, being found primarily in southern Japan, the Caribbean, west and central Africa, and the South Pacific islands. Evidence for causality includes the monoclonal integration of viral genome in almost all cases of ATL in carriers. The risk factors for HTLV-1-associated malignancy appear to be perinatal infection, high viral load, and being male sex.

Adult T cell leukemia is a cancer of the blood and bone marrow. The standard treatments for adult T cell leukemia/lymphoma are radiation therapy, immunotherapy, and chemotherapy. Radiation therapy might be external beam radiation therapy or brachytherapy. Other methods of treating adult T cell leukemia/lymphoma include immunotherapy and high-dose chemotherapy with stem cell transplantation.

In some embodiments, described herein is a method of treating a viral-induced adult T cell leukemia/lymphoma comprising administering to a subject in need thereof an oral solid formulation comprising an iniparib active ingredient; an oral dosage form comprising an immediate-release top layer and a controlled-release core, in which the controlled-release layer comprises an iniparib active ingredient, and in which the oral dosage form is in either a solid or a liquid form; an oral liquid formulation comprising an iniparib active ingredient; and an aerosol formulation comprising an iniparib active ingredient. In some instances, the method further comprises administration of iniparib in combination with, e.g., radiation therapy, chemotherapy, immunotherapy and high-dose chemotherapy with stem cell transplantation, or a combination thereof.

Viral-Induced Cervical Cancer

Infection of the cervix with human papillomavirus (HPV) is the most common cause of cervical cancer. Not all women with HPV infection, however, will develop cervical cancer. Cervical cancer usually develops slowly over time. Before cancer appears in the cervix, the cells of the cervix go through changes known as dysplasia, in which cells that are not normal begin to appear in the cervical tissue. Later, cancer cells start to grow and spread more deeply into the cervix and to surrounding areas. The standard treatments for cervical cancers are surgery, immunotherapy, radiation therapy and chemotherapy. The types of surgery that might be used are conization, total hysterectomy, bilateral salpingo-oophorectomy, radical hysterectomy, pelvic exenteration, cryosurgery, laser surgery, and loop electrosurgical excision procedure. Radiation therapy might be external beam radiation therapy or brachytherapy.

In some embodiments, described herein is a method of treating a viral-induced cervical cancer comprising administering to a subject in need thereof an oral solid formulation comprising an iniparib active ingredient; an oral dosage form comprising an immediate-release top layer and a controlled-release core, in which the controlled-release layer comprises an iniparib active ingredient, and in which the oral dosage form is in either a solid or a liquid form; an oral liquid formulation comprising an iniparib active ingredient; and an aerosol formulation comprising an iniparib active ingredient. In some instances, the method further comprises administration of iniparib in combination with, e.g., radiation therapy, chemotherapy, or a combination thereof.

CNS Cancers

Brain and spinal cord tumors are abnormal growths of tissue found inside the skull or the bony spinal column, which are the primary components of the central nervous system (CNS). Benign tumors are non-cancerous, and malignant tumors are cancerous. The CNS is housed within rigid, bony quarters (i.e., the skull and spinal column), so any abnormal growth, whether benign or malignant, can place pressure on sensitive tissues and impair function. Tumors that originate in the brain or spinal cord are called primary tumors. Most primary tumors are caused by out-of-control growth among cells that surround and support neurons. In a small number of individuals, primary tumors might result from specific genetic disease (e.g., neurofibromatosis, tuberous sclerosis) or from exposure to radiation or cancer-causing chemicals. The cause of most primary tumors remains a mystery.

The first test to diagnose brain and spinal column tumors is a neurological examination. Special imaging techniques (computed tomography, and magnetic resonance imaging, positron emission tomography) are also employed. Laboratory tests include the EEG and the spinal tap. A biopsy, a surgical procedure in which a sample of tissue is taken from a suspected tumor, helps doctors diagnose the type of tumor.

Tumors are classified according to the kind of cell from which the tumor seems to originate. The most common primary brain tumor in adults comes from cells in the brain called astrocytes that make up the blood-brain barrier and contribute to the nutrition of the central nervous system. These tumors are called gliomas (astrocytoma, anaplastic astrocytoma, or glioblastoma multiforme) and account for 65% of all primary central nervous system tumors. Some of the tumors are, but not limited to, Oligodendroglioma, Ependymoma, Meningioma, Lymphoma, Schwannoma, and Medulloblastoma.

Neuroepithelial Tumors of the CNS

Astrocytic tumors, such as astrocytoma; anaplastic (malignant) astrocytoma, such as hemispheric, diencephalic, optic, brain stem, cerebellar; glioblastoma multiforme; pilocytic astrocytoma, such as hemispheric, diencephalic, optic, brain stem, cerebellar; subependymal giant cell astrocytoma; and pleomorphic xanthoastrocytoma. Oligodendroglial tumors, such as oligodendroglioma; and anaplastic (malignant) oligodendroglioma. Ependymal cell tumors, such as ependymoma; anaplastic ependymoma; myxopapillary ependymoma; and subependymoma. Mixed gliomas, such as mixed oligoastrocytoma; anaplastic (malignant) oligoastrocytoma; and others (e.g. ependymo-astrocytomas). Neuroepithelial tumors of uncertain origin, such as polar spongioblastoma; astroblastoma; and gliomatosis cerebri. Tumors of the choroid plexus, such as choroid plexus papilloma; and choroid plexus carcinoma (anaplastic choroid plexus papilloma). Neuronal and mixed neuronal-glial tumors, such as gangliocytoma; dysplastic gangliocytoma of cerebellum (Lhermitte-Duclos); ganglioglioma; anaplastic (malignant) ganglioglioma; desmoplastic infantile ganglioglioma, such as desmoplastic infantile astrocytoma; central neurocytoma; dysembryoplastic neuroepithelial tumor; olfactory neuroblastoma (esthesioneuroblastoma. Pineal Parenchyma Tumors, such as pineocytoma; pineoblastoma; and mixed pineocytoma/pineoblastoma. Tumors with neuroblastic or glioblastic elements (embryonal tumors), such as medulloepithelioma; primitive neuroectodermal tumors with multipotent differentiation, such as medulloblastoma; cerebral primitive neuroectodermal tumor; neuroblastoma; retinoblastoma; and ependymoblastoma.

Other CNS Neoplasms

Tumors of the Sellar Region, such as pituitary adenoma; pituitary carcinoma; and craniopharyngioma. Hematopoietic tumors, such as primary malignant lymphomas; plasmacytoma; and granulocytic sarcoma. Germ Cell Tumors, such as germinoma; embryonal carcinoma; yolk sac tumor (endodermal sinus tumor); choriocarcinoma; teratoma; and mixed germ cell tumors. Tumors of the Meninges, such as meningioma; atypical meningioma; and anaplastic (malignant) meningioma. Non-menigothelial tumors of the meninges, such as Benign Mesenchymal; Malignant Mesenchymal; Primary Melanocytic Lesions; Hemopoietic Neoplasms; and Tumors of Uncertain Histogenesis, such as hemangioblastoma (capillary hemangioblastoma). Tumors of Cranial and Spinal Nerves, such as schwannoma (neurinoma, neurilemoma); neurofibroma; malignant peripheral nerve sheath tumor (malignant schwannoma), such as epithelioid, divergent mesenchymal or epithelial differentiation, and melanotic. Local Extensions from Regional Tumors; such as paraganglioma (chemodectoma); chordoma; chodroma; chondrosarcoma; and carcinoma. Metastatic tumors, Unclassified Tumors and Cysts and Tumor-like Lesions, such as Rathke cleft cyst; Epidermoid; dermoid; colloid cyst of the third ventricle; enterogenous cyst; neuroglial cyst; granular cell tumor (choristoma, pituicytoma); hypothalamic neuronal hamartoma; nasal glial herterotopia; and plasma cell granuloma.

Chemotherapeutics available are, but not limited to, alkylating agents such as, Cyclophosphamide, Ifosphamide, Melphalan, Chlorambucil, BCNU, CCNU, Decarbazine, Procarbazine, Busulfan, and Thiotepa; antimetabolites such as, Methotraxate, 5-Fluorouracil, Cytarabine, Gemcitabine (Gemzar®), 6-mercaptopurine, 6-thioguanine, Fludarabine, and Cladribine; anthracyclins such as, daunorubicin. Doxorubicin, Idarubicin, Epirubicin and Mitoxantrone; antibiotics such as, Bleomycin; camptothecins such as, irinotecan and topotecan; taxanes such as, paclitaxel and docetaxel; and platinums such as, Cisplatin, carboplatin, and Oxaliplatin.

The treatments are surgery, radiation therapy, immunotherapy, hyperthermia, gene therapy, chemotherapy, and combination of radiation and chemotherapy. Doctors also might prescribe steroids to reduce the swelling inside the CNS.

In some embodiments, described herein is a method of treating a CNS cancer comprising administering to a subject in need thereof an oral solid formulation comprising an iniparib active ingredient; an oral dosage form comprising an immediate-release top layer and a controlled-release core, in which the controlled-release layer comprises an iniparib active ingredient, and in which the oral dosage form is in either a solid or a liquid form; an oral liquid formulation comprising an iniparib active ingredient; and an aerosol formulation comprising an iniparib active ingredient. In some instances, the method further comprises administration of iniparib in combination with, e.g., radiation therapy, chemotherapy, or a combination thereof.

PANS Cancers

The peripheral nervous system consists of the nerves that branch out from the brain and spinal cord. These nerves form the communication network between the CNS and the body parts. The peripheral nervous system is further subdivided into the somatic nervous system and the autonomic nervous system. The somatic nervous system consists of nerves that go to the skin and muscles and is involved in conscious activities. The autonomic nervous system consists of nerves that connect the CNS to the visceral organs such as the heart, stomach, and intestines. It mediates unconscious activities.

Acoustic neuromas are benign fibrous growths that arise from the balance nerve, also called the eighth cranial nerve or vestibulocochlear nerve. These tumors are non-malignant, meaning that they do not spread or metastasize to other parts of the body. The location of these tumors is deep inside the skull, adjacent to vital brain centers in the brain stem. As the tumors enlarge, they involve surrounding structures which have to do with vital functions. In the majority of cases, these tumors grow slowly over a period of years.

The malignant peripheral nerve sheath tumor (MPNST) is the malignant counterpart to benign soft tissue tumors such as neurofibromas and schwannomas. It is most common in the deep soft tissue, usually in close proximity of a nerve trunk. The most common sites include the sciatic nerve, brachial plexus, and sarcal plexus. The most common symptom is pain which usually prompts a biopsy. It is a rare, aggressive, and lethal orbital neoplasm that usually arises from sensory branches of the trigeminal nerve in adults. Malignant PNS tumor spreads along nerves to involve the brain, and most patients die within 5 years of clinical diagnosis. The MPNST might be classified into three major categories with epithelioid, mesenchymal or glandular characteristics. Some of the MPNST include but not limited to, Subcutaneous malignant epithelioid schwannoma with cartilaginous differentiation, Glandular malignant schwannoma, Malignant peripheral nerve sheath tumor with perineurial differentiation, Cutaneous epithelioid malignant nerve sheath tumor with rhabdoid features, Superficial epithelioid MPNST, Triton Tumor (MPNST with rhabdomyoblastic differentiation), Schwannoma with rhabdomyoblastic differentiation. Rare MPNST cases contain multiple sarcomatous tissue types, especially osteosarcoma, chondrosarcoma and angiosarcoma. These have sometimes been indistinguishable from the malignant mesenchymoma of soft tissue.

Other types of PNS cancers include but not limited to, malignant fibrous cytoma, malignant fibrous histiocytoma, malignant meningioma, malignant mesothelioma, and malignant mixed Müllerian tumor.

The treatments are surgery, radiation therapy, immunotherapy, chemotherapy, and combination of radiation and chemotherapy.

In some embodiments, described herein is a method of treating a PNS cancer comprising administering to a subject in need thereof an oral solid formulation comprising an iniparib active ingredient; an oral dosage form comprising an immediate-release top layer and a controlled-release core, in which the controlled-release layer comprises an iniparib active ingredient, and in which the oral dosage form is in either a solid or a liquid form; an oral liquid formulation comprising an iniparib active ingredient; and an aerosol formulation comprising an iniparib active ingredient. In some instances, the method further comprises administration of iniparib in combination with, e.g., radiation therapy, chemotherapy, or a combination thereof.

Oral Cavity and Oropharyngeal Cancer

Management of patients with central nervous system (CNS) cancers remains a formidable task. Cancers such as hypopharyngeal cancer, laryngeal cancer, nasopharyngeal cancer, oropharyngeal cancer, and the like, have been treated with surgery, immunotherapy, chemotherapy, combination of chemotherapy, and radiation therapy. Etoposide and actinomycin D, two commonly used oncology agents that inhibit topoisomerase II, fail to cross the blood-brain barrier in useful amounts.

In some embodiments, described herein is a method of treating an oral cavity and oropharyngeal cancer comprising administering to a subject in need thereof an oral solid formulation comprising an iniparib active ingredient; an oral dosage form comprising an immediate-release top layer and a controlled-release core, in which the controlled-release layer comprises an iniparib active ingredient, and in which the oral dosage form is in either a solid or a liquid form; an oral liquid formulation comprising an iniparib active ingredient; and an aerosol formulation comprising an iniparib active ingredient. In some instances, the method further comprises administration of iniparib in combination with, e.g., radiation therapy, chemotherapy, or a combination thereof.

Stomach Cancer

Stomach cancer is the result of cell changes in the lining of the stomach. There are three main types of stomach cancers: lymphomas, gastric stromal tumors, and carcinoid tumors. Lymphomas are cancers of the immune system tissue that are sometimes found in the wall of the stomach. Gastric stromal tumors develop from the tissue of the stomach wall. Carcinoid tumors are tumors of hormone-producing cells of the stomach.

The causes of stomach cancer continue to be debated. A combination of heredity and environment (diet, smoking, etc) are all thought to play a part. Common approaches to the treatment include surgery, immunotherapy, chemotherapy, radiation therapy, combination of chemotherapy, and radiation therapy or biological therapy.

In some embodiments, described herein is a method of treating a stomach cancer comprising administering to a subject in need thereof an oral solid formulation comprising an iniparib active ingredient; an oral dosage form comprising an immediate-release top layer and a controlled-release core, in which the controlled-release layer comprises an iniparib active ingredient, and in which the oral dosage form is in either a solid or a liquid form; an oral liquid formulation comprising an iniparib active ingredient; and an aerosol formulation comprising an iniparib active ingredient. In some instances, the method further comprises administration of iniparib in combination with, e.g., radiation therapy, chemotherapy, or a combination thereof.

Testicular Cancer

Testicular cancer is cancer that typically develops in one or both testicles in young men. Cancers of the testicle develop in certain cells known as germ cells. The 2 main types of germ cell tumors (GCTs) that occur in men are seminomas (60%) and nonseminomas (40%). Tumors can also arise in the supportive and hormone-producing tissues, or stroma, of the testicles. Such tumors are known as gonadal stromal tumors. The 2 main types are Leydig cell tumors and Sertoli cell tumors. Secondary testicular tumors are those that start in another organ and then spread to the testicle. Lymphoma is the most common secondary testicular cancer.

Common approaches to the treatment include surgery, immunotherapy, chemotherapy, radiation therapy, combination of chemotherapy, and radiation therapy or biological therapy. Several drugs are typically used to treat testicular cancer: Platinol (cisplatin), Vepesid or VP-16 (etoposide) and Blenoxane (bleomycin sulfate). Additionally, Ifex (ifosfamide), Velban (vinblastine sulfate) and others might be used.

In some embodiments, described herein is a method of treating a testicular cancer comprising administering to a subject in need thereof an oral solid formulation comprising an iniparib active ingredient; an oral dosage form comprising an immediate-release top layer and a controlled-release core, in which the controlled-release layer comprises an iniparib active ingredient, and in which the oral dosage form is in either a solid or a liquid form; an oral liquid formulation comprising an iniparib active ingredient; and an aerosol formulation comprising an iniparib active ingredient. In some instances, the method further comprises administration of iniparib in combination with, e.g., radiation therapy, chemotherapy, or a combination thereof.

Thymus Cancer

The thymus is a small organ located in the upper/front portion of your chest, extending from the base of the throat to the front of the heart. The thymus contains 2 main types of cells, thymic epithelial cells and lymphocytes. Thymic epithelial cells can give origin to thymomas and thymic carcinomas. Lymphocytes, whether in the thymus or in the lymph nodes, can become malignant and develop into cancers called Hodgkin disease and non-Hodgkin lymphomas. The thymus also contains another much less common type of cells called Kulchitsky cells, or neuroendocrine cells, which normally release certain hormones. These cells can give rise to cancers, called carcinoids or carcinoid tumors that often release the same type of hormones, and are similar to other tumors arising from neuroendocrine cells elsewhere in the body.

Common approaches to the treatment include surgery, immunotherapy, chemotherapy, radiation therapy, combination of chemotherapy and radiation therapy or biological therapy. Anticancer drugs that have been used in the treatment of thymomas and thymic carcinomas are doxorubicin (adriamycin), cisplatin, ifosfamide, and corticosteroids (prednisone). Often, these drugs are given in combination to increase their effectiveness. Combinations used to treat thymic cancer include cisplatin, doxorubicin, etoposide and cyclophosphamide, and the combination of cisplatin, doxorubicin, cyclophosphamide, and vincristine.

In some embodiments, described herein is a method of treating a thymus cancer comprising administering to a subject in need thereof an oral solid formulation comprising an iniparib active ingredient; an oral dosage form comprising an immediate-release top layer and a controlled-release core, in which the controlled-release layer comprises an iniparib active ingredient, and in which the oral dosage form is in either a solid or a liquid form; an oral liquid formulation comprising an iniparib active ingredient; and an aerosol formulation comprising an iniparib active ingredient. In some instances, the method further comprises administration of iniparib in combination with, e.g., radiation therapy, chemotherapy, or a combination thereof.

Combination Therapy

In some embodiments disclosed herein are methods for treating cancer using different combinations of treatment regimens. For example, such combinations might include, but are not limited to, the use of one or more of iniparib or a pharmaceutically acceptable salt, solvate, isomer, tautomer, metabolite, analog, or prodrug thereof in conjunction with one or more another anti-cancer therapy including but not limited to various antineoplastic chemotherapeutic agents, chemopreventative agents, side-effect limiting agents, surgery, radiation therapy (e.g. X ray), gene therapy, DNA therapy, adjuvant therapy, neoadjuvant therapy, viral therapy, immunotherapy, RNA therapy, and/or nanotherapy.

Where the combination therapy further comprises a non-drug treatment, the non-drug treatment might be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, by a significant period of time. The conjugate and the other pharmacologically active agent might be administered to a patient simultaneously, sequentially or in combination. It will be appreciated that when using a combination therapy, iniparib and the other pharmacologically active agent might be in the same pharmaceutically acceptable carrier and therefore administered simultaneously. They might be in separate pharmaceutical carriers such as conventional oral dosage forms which are taken simultaneously. The term "combination" further refers to the case where the active compounds are provided in separate dosage forms and are administered sequentially.

Antineoplastic Chemotherapeutic Agents

Suitable antineoplastic chemotherapeutic agents to be used in combination with iniparib include, but are not limited to, alkylating agents, antimetabolites, natural antineoplastic agents, hormonal antineoplastic agents, angiogenesis inhibitors, differentiating reagents, RNA inhibitors, antibodies or immunotherapeutic agents, gene therapy agents, small molecule enzymatic inhibitors, biological response modifiers, and anti-metastatic agents.

Alkylating Agents

Alkylating agents are known to act through the alkylation of macromolecules such as the DNA of cancer cells, and are usually strong electrophiles. This activity can disrupt DNA synthesis and cell division. Examples of alkylating reagents suitable for use herein include nitrogen mustards and their analogues and derivatives including, cyclophosphamide, ifosfamide, chlorambucil, estramustine, mechlorethamine hydrochloride, melphalan, and uracil mustard. Other examples of alkylating agents include alkyl sulfonates (e.g. busulfan), nitrosoureas (e.g. carmustine, lomustine, and streptozocin), triazenes (e.g. dacarbazine and temozolomide), ethylenimines/methylmelamines (e.g. altretamine and thiotepa), and methylhydrazine derivatives (e.g. procarbazine). Included in the alkylating agent group are the alkylating-like platinum-containing drugs comprising carboplatin, cisplatin, and oxaliplatin.

Antimetabolites

Antimetabolic antineoplastic agents structurally resemble natural metabolites, and are involved in normal metabolic processes of cancer cells such as the synthesis of nucleic acids and proteins. They differ enough from the natural metabolites so that they interfere with the metabolic processes of cancer cells. Suitable antimetabolic antineoplastic agents to be used in combination with iniparib can be classified according to the metabolic process they affect, and can include, but are not limited to, analogues and derivatives of folic acid, pyrimidines, purines, and cytidine. Members of the folic acid group of agents suitable for use herein include, but are not limited to, methotrexate (amethopterin), pemetrexed and their analogues and derivatives. Pyrimidine agents suitable for use herein include, but are not limited to, cytarabine, floxuridine, fluorouracil (5-fluorouracil), capecitabine, gemcitabine, and their analogues and derivatives. Purine agents suitable for use herein include, but are not limited to, mercaptopurine (6-mercaptopurine), pentostatin, thioguanine, cladribine, and their analogues and derivatives. Cytidine agents suitable for use herein include, but are not limited to, cytarabine (cytosine arabinodside), azacitidine (5-azacytidine) and their analogues and derivatives.

Natural Antineoplastic Agents

Natural antineoplastic agents comprise antimitotic agents, antibiotic antineoplastic agents, camptothecin analogues, and enzymes. Antimitotic agents suitable for use herein include, but are not limited to, *vinca* alkaloids like vinblastine, vincristine, vindesine, vinorelbine, and their analogues and derivatives. They are derived from the Madagascar periwinkle plant and are usually cell cycle-specific for the M phase, binding to tubulin in the microtubules of cancer cells. Other antimitotic agents suitable for use herein are the podophyllotoxins, which include, but are not limited to etoposide, teniposide, and their analogues and derivatives. These reagents predominantly target the G2 and late S phase of the cell cycle.

Also included among the natural antineoplastic agents are the antibiotic antineoplastic agents. Antibiotic antineoplastic agents are antimicrobial drugs that have anti-tumor properties usually through interacting with cancer cell DNA. Antibiotic antineoplastic agents suitable for use herein include, but are not limited to, belomycin, dactinomycin, doxorubicin, idarubicin, epirubicin, mitomycin, mitoxantrone, pentostatin, plicamycin, and their analogues and derivatives.

The natural antineoplastic agent classification also includes camptothecin analogues and derivatives which are suitable for use herein and include camptothecin, topotecan, and irinotecan. These agents act primarily by targeting the nuclear enzyme topoisomerase I. Another subclass under the natural antineoplastic agents is the enzyme, L-asparaginase and its variants. L-asparaginase acts by depriving some cancer cells of L-asparagine by catalyzing the hydrolysis of circulating asparagine to aspartic acid and ammonia.

Hormonal Antineoplastic Agents

Hormonal antineoplastic agents act predominantly on hormone-dependent cancer cells associated with prostate tissue, breast tissue, endometrial tissue, ovarian tissue, lymphoma, and leukemia. Such tissues might be responsive to and dependent upon such classes of agents as glucocorticoids, progestins, estrogens, and androgens. Both analogues and derivatives that are agonists or antagonists are suitable for use in combination with iniparib to treat tumors. Examples of glucocorticoid agonists/antagonists suitable for use herein are dexamethasone, cortisol, corticosterone, prednisone, mifepristone (RU486), their analogues and derivatives. The progestin agonist/antagonist subclass of agents suitable for use herein includes, but is not limited to, hydroxyprogesterone, medroxyprogesterone, megestrol acetate, mifepristone (RU486), ZK98299, their analogues and derivatives. Examples from the estrogen agonist/antagonist subclass of agents suitable for use herein include, but are not limited to, estrogen, tamoxifen, toremifene, RU58668, SR16234, ZD164384, ZK191703, fulvestrant, their analogues and derivatives. Examples of aromatase inhibitors suitable for use herein, which inhibit estrogen production, include, but are not limited to, androstenedione, formestane, exemestane, aminoglutethimide, anastrozole, letrozole, their analogues and derivatives. Examples from the androgen agonist/antagonist subclass of agents suitable for use herein include, but are not limited to, testosterone, dihydrotestosterone, fluoxymesterone, testolactone, testosterone enanthate, testosterone propionate, gonadotropin-releasing hormone agonists/antagonists (e.g. leuprolide, goserelin, triptorelin, buserelin), diethylstilbestrol, abarelix, cyproterone, flutamide, nilutamide, bicalutamide, their analogues and derivatives.

Angiogenesis Inhibitors

Angiogenesis inhibitors work by inhibiting the vascularization of tumors. Angiogenesis inhibitors encompass a wide variety of agents including small molecule agents, antibody agents, and agents that target RNA function. Examples of angiogenesis inhibitors suitable for use herein include, but are not limited to, ranibizumab, bevacizumab, SU11248, PTK787, ZK222584, CEP-7055, angiozyme, dalteparin, thalidomide, suramin, CC-5013, combretastatin A4 Phosphate, LY317615, soy isoflavones, AE-941, interferon alpha, PTK787/ZK 222584, ZD6474, EMD 121974, ZD6474, BAY 543-9006, celecoxib, halofuginone hydrobromide, bevacizumab, their analogues, variants, or derivatives.

Differentiating Reagents

Differentiating agents inhibit tumor growth through mechanisms that induce cancer cells to differentiate. One such subclass of these agents suitable for use herein includes, but is not limited to, vitamin A analogues or retinoids, and peroxisome proliferator-activated receptor agonists (PPARs). Retinoids suitable for use herein include, but are not limited to, vitamin A, vitamin A aldehyde (retinal), retinoic acid, fenretinide, 9-cis-retinoid acid, 13-cis-retinoid acid, all-trans-retinoic acid, isotretinoin, tretinoin, retinyl palmitate, their analogues and derivatives. Agonists of PPARs suitable for use herein include, but are not limited to, troglitazone, ciglitazone, tesaglitazar, their analogues and derivatives.

RNA Inhibitors

Certain RNA inhibiting agents might be utilized to inhibit the expression or translation of messenger RNA ("mRNA") that is associated with a cancer phenotype. Examples of such agents suitable for use herein include, but are not limited to, short interfering RNA ("siRNA"), ribozymes, and antisense oligonucleotides. Specific examples of RNA inhibiting agents suitable for use herein include, but are not limited to, Cand5, Sirna-027, fomivirsen, and angiozyme.

Antibodies/Immunotherapeutic Agents

Antibody agents bind targets selectively expressed in cancer cells and can either utilize a conjugate to kill the cell associated with the target, or elicit the body's immune response to destroy the cancer cells. Immunotherapeutic agents can either be comprised of polyclonal or monoclonal antibodies. The antibodies might be comprised of non-human animal (e.g. mouse) and human components, or be comprised of entirely human components ("humanized antibodies"). Examples of monoclonal immunotherapeutic agents suitable for use herein include, but are not limited to, rituximab, tosibtumomab, ibritumomab which target the CD-20 protein. Other examples suitable for use herein include trastuzumab, edrecolomab, bevacizumab, cetuximab, carcinoembryonic antigen antibodies, gemtuzumab, alemtuzumab, mapatumumab, panitumumab, EMD 72000, TheraCIM hR3, 2C4, HGS-TR2J, and HGS-ETR2.

Gene Therapy Agents

Gene therapy agents insert copies of genes into a specific set of a patient's cells, and can target both cancer and non-cancer cells. The goal of gene therapy can be to replace altered genes with functional genes, to stimulate a patient's immune response to cancer, to make cancer cells more sensitive to chemotherapy, to place "suicide" genes into cancer cells, or to inhibit angiogenesis. Genes might be delivered to target cells using viruses, liposomes, or other carriers or vectors. This might be done by injecting the gene-carrier composition into the patient directly, or ex vivo, with infected cells being introduced back into a patient. Such compositions are suitable for use in combination with iniparib.

Small Molecule Enzymatic Inhibitors

Certain small molecule therapeutic agents are able to target the tyrosine kinase enzymatic activity or downstream signal transduction signals of certain cell receptors such as epidermal growth factor receptor ("EGFR") or vascular endothelial growth factor receptor ("VEGFR"). Such targeting by small molecule therapeutics can result in anti-cancer effects. Examples of such agents suitable for use herein include, but are not limited to, imatinib, gefitinib, erlotinib, lapatinib, canertinib, ZD6474, sorafenib (BAY 43-9006), ERB-569, and their analogues and derivatives.

Biological Response Modifiers

Certain protein or small molecule agents can be used in anti-cancer therapy through either direct anti-tumor effects or through indirect effects. Examples of direct-acting agents suitable for use herein include, but are not limited to, differentiating reagents such as retinoids and retinoid derivatives. Indirect-acting agents suitable for use herein include, but are not limited to, agents that modify or enhance the immune or other systems such as interferons, interleukins, hematopoietic growth factors (e.g. erythropoietin), and antibodies (monoclonal and polyclonal).

Anti-Metastatic Agents

The process whereby cancer cells spread from the site of the original tumor to other locations around the body is termed cancer metastasis. Certain agents have anti-metastatic properties, designed to inhibit the spread of cancer cells. Examples of such agents suitable for use herein include, but are not limited to, marimastat, bevacizumab, trastuzumab, rituximab, erlotinib, MMI-166, GRN163L, hunter-killer peptides, tissue inhibitors of metalloproteinases (TIMPs), their analogues, derivatives and variants.

Chemopreventative Agents

Certain pharmaceutical agents might be used to prevent initial occurrences of cancer, or to prevent recurrence or metastasis. Administration with such chemopreventative agents in combination with one or more of iniparib or a pharmaceutically acceptable salt, solvate, isomer, tautomer, metabolite, analog, or prodrug thereof might act to both treat and prevent the recurrence of cancer. Examples of chemopreventative agents suitable for use herein include, but are not limited to, tamoxifen, raloxifene, tibolone, bisphosphonate, ibandronate, estrogen receptor modulators, aromatase inhibitors (letrozole, anastrozole), luteinizing hormone-releasing hormone agonists, goserelin, vitamin A, retinal, retinoic acid, fenretinide, 9-cis-retinoid acid, 13-cis-retinoid acid, all-trans-retinoic acid, isotretinoin, tretinoin, vitamin B6, vitamin B12, vitamin C, vitamin D, vitamin E, cyclooxygenase inhibitors, non-steroidal anti-inflammatory drugs (NSAIDs), aspirin, ibuprofen, celecoxib, polyphenols, polyphenol E, green tea extract, folic acid, glucaric acid, interferon-alpha, anethole dithiolethione, zinc, pyridoxine, finasteride, doxazosin, selenium, indole-3-carbinal, alpha-difluoromethylornithine, carotenoids, beta-carotene, lycopene, antioxidants, coenzyme Q10, flavonoids, quercetin, curcumin, catechins, epigallocatechin gallate, N-acetylcysteine, indole-3-carbinol, inositol hexaphosphate, isoflavones, glucanic acid, rosemary, soy, saw palmetto, and calcium. An additional example of chemopreventative agents suitable for use in combination with iniparib is cancer vaccines. These can be created through immunizing a patient with all or part of a cancer cell type that is targeted by the vaccination process.

Side-Effect Limiting Agents

Treatment of cancer with iniparib alone or in combination with other antineoplastic compounds might be accompanied by administration of pharmaceutical agents that can alleviate the side effects produced by the antineoplastic agents. Such agents suitable for use herein include, but are not limited to, anti-emetics, anti-mucositis agents, pain management agents, infection control agents, and anti-anemia/anti-thrombocytopenia agents. Examples of anti-emetics suitable for use herein include, but are not limited to, 5-hydroxytryptamine 3 receptor antagonists, metoclopramide, steroids, lorazepam, ondansetron, cannabinoids, their analogues and derivatives. Examples of anti-mucositis agents suitable for use herein include, but are not limited to, palifermin (keratinocyte growth factor), glucagon-like peptide-2, teduglutide, L-glutamine, amifostin, and fibroblast growth factor 20. Examples of pain management agents suitable for use herein include, but are not limited to, opioids, opiates, and non-steroidal anti-inflammatory compounds. Examples of agents used for control of infection suitable for use herein include, but are not limited to, antibacterials such as aminoglycosides, penicillins, cephalosporins, tetracyclines, clindamycin, lincomycin, macrolides, vancomycin, carbapenems, monobactams, fluoroquinolones, sulfonamides, nitrofurantoins, their analogues and derivatives. Examples of agents that can treat anemia or thrombocytopenia associated with chemotherapy suitable for use herein include, but are not limited to, erythropoietin, and thrombopoietin.

Several other suitable therapies for use in combination with iniparib are also available. For example, see Goodman & Gilman's The Pharmacological Basis of Therapeutics 11th ed. Brunton L L, Lazo J S, and Parker K L, ed. McGraw-Hill, New York, 2006.

Radiation Therapy

Radiation therapy (or radiotherapy) is the medical use of ionizing radiation as part of cancer treatment to control malignant cells. Radiotherapy might be used for curative or adjuvant cancer treatment. It is used as palliative treatment (where cure is not possible and the aim is for local disease control or symptomatic relief) or as therapeutic treatment (where the therapy has survival benefit and it can be curative). Radiotherapy is used for the treatment of malignant tumors and might be used as the primary therapy. It is also common to combine radiotherapy with surgery, chemotherapy, hormone therapy or some mixture of the three. Most common cancer types can be treated with radiotherapy in some way. The precise treatment intent (curative, adjuvant, neoadjuvant, therapeutic, or palliative) will depend on the tumor type, location, and stage, as well as the general health of the patient.

Radiation therapy is commonly applied to the cancerous tumor. The radiation fields might also include the draining lymph nodes if they are clinically or radiologically involved with tumor, or if there is thought to be a risk of subclinical malignant spread. It is necessary to include a margin of normal tissue around the tumor to allow for uncertainties in daily set-up and internal tumor motion.

Radiation therapy works by damaging the DNA of cells. The damage is caused by a photon, electron, proton, neutron, or ion beam directly or indirectly ionizing the atoms which make up the DNA chain. Indirect ionization happens as a result of the ionization of water, forming free radicals, notably hydroxyl radicals, which then damage the DNA. In the most common forms of radiation therapy, most of the radiation effect is through free radicals. Because cells have mechanisms for repairing DNA damage, breaking the DNA on both strands proves to be the most significant technique in modifying cell characteristics. Because cancer cells generally are undifferentiated and stem cell-like, they reproduce more, and have a diminished ability to repair sub-lethal damage compared to most healthy differentiated cells. The DNA damage is inherited through cell division, accumulating damage to the cancer cells, causing them to die or reproduce more slowly. Proton radiotherapy works by sending protons with varying kinetic energy to precisely stop at the tumor.

Gamma rays are also used to treat some types of cancer including uterine, endometrial, and ovarian cancers. In the procedure called gamma-knife surgery, multiple concentrated beams of gamma rays are directed on the growth in order to kill the cancerous cells. The beams are aimed from different angles to focus the radiation on the growth while minimizing damage to the surrounding tissues.

In some embodiments, a pharmaceutical composition, formulation, and/or dosage form of iniparib, or a pharmaceutically acceptable salt, solvate, metabolite, or prodrug thereof disclosed herein is used in combination with radiotherapy to treat cancer.

Adjuvant Therapy

Adjuvant therapy is a treatment given after the primary treatment to increase the chances of a cure. Adjuvant therapy might include chemotherapy, radiation therapy, hormone therapy, or biological therapy.

Adjuvant chemotherapy is effective for patients with advanced uterine cancer or ovarian cancer. The combination of doxorubicin and cisplatin achieves overall response rates ranging from 34 to 60%, and the addition of paclitaxel seems to improve the outcome of patients with advanced disease, but it induces a significantly higher toxicity. A Gynecologic Oncology Study Group phase-III study is currently exploring the triplet paclitaxel+doxorubicin+cisplatin plus G-CSF vs. the less toxic combination of paclitaxel+carboplatin. Ongoing and planned phase-III trials are evaluating newer combination chemotherapy regimens, a combination of irradiation and chemotherapy and the implementation of targeted therapies with the goal of improving the tumor control rate and quality of life.

Adjuvant radiation therapy (RT)-Adjuvant radiation therapy significantly reduces the risk that the uterine cancer will recur locally (i.e., in the pelvis or vagina). In general, there are two ways of delivering RT: it might be given as vaginal brachytherapy or as external beam RT (EBRT). In vaginal brachytherapy, brachytherapy delivers RT directly to the vaginal tissues from a source that is temporarily placed inside the body. This allows high doses of radiation to be delivered to the area where cancer cells are most likely to be found. With external beam radiation therapy (EBRT), the source of the radiation is outside the body.

Various therapies including but not limited to hormone therapy, e.g. tamoxifen, or gonadotropin-releasing hormone (GnRH) analogues, and radioactive monoclonal antibody therapy have been used to treat ovarian cancer.

Neoadjuvant Therapy

Neoadjuvant therapy refers to a treatment given before the primary treatment. Examples of neoadjuvant therapy include chemotherapy, radiation therapy, and hormone therapy. Neoadjuvant chemotherapy in gynecological cancers is an approach that is shown to have positive effects on survival. It increases the rate of resectability in ovarian and cervical cancers and thus contributes to survival (Ayhan A. et. al. European journal of gynaecological oncology. 2006, vol. 27).

Oncolytic Viral Therapy

Viral therapy for cancer utilizes a type of viruses called oncolytic viruses. An oncolytic virus is a virus that is able to infect and lyse cancer cells, while leaving normal cells unharmed, making them potentially useful in cancer therapy. Replication of oncolytic viruses both facilitates tumor cell destruction and also produces dose amplification at the tumor site. They might also act as vectors for anticancer genes, allowing them to be specifically delivered to the tumor site.

There are two main approaches for generating tumor selectivity: transductional and non-transductional targeting. Transductional targeting involves modifying the specificity of viral coat protein, thus increasing entry into target cells while reducing entry to non-target cells. Non-transductional targeting involves altering the genome of the virus so it can only replicate in cancer cells. This can be done by either transcription targeting, where genes essential for viral replication are placed under the control of a tumor-specific promoter, or by attenuation, which involves introducing deletions into the viral genome that eliminate functions that are dispensable in cancer cells, but not in normal cells. There are also other, slightly more obscure methods.

Chen et al (2001) used CV706, a prostate-specific adenovirus, in conjunction with radiotherapy on prostate cancer in mice. The combined treatment results in a synergistic increase in cell death, as well as a significant increase in viral burst size (the number of virus particles released from each cell lysis).

ONYX-015 has undergone trials in conjunction with chemotherapy. The combined treatment gives a greater response than either treatment alone, but the results have not been entirely conclusive. ONYX-015 has shown promise in conjunction with radiotherapy.

Viral agents administered intravenously can be particularly effective against metastatic cancers, which are especially difficult to treat conventionally. However, bloodborne viruses can be deactivated by antibodies and cleared from the blood stream quickly e.g. by Kupffer cells (extremely active phagocytic cells in the liver, which are responsible for adenovirus clearance). Avoidance of the immune system until the tumor is destroyed could be the biggest obstacle to the success of oncolytic virus therapy. To date, no technique used to evade the immune system is entirely satisfactory. It is in conjunction with conventional cancer therapies that oncolytic viruses show the most promise, since combined therapies operate synergistically with no apparent negative effects.

The specificity and flexibility of oncolytic viruses means they have the potential to treat a wide range of cancers including uterine cancer, endometrial cancer, and ovarian cancer with minimal side effects. Oncolytic viruses have the potential to solve the problem of selectively killing cancer cells.

Nanotherapy

Nanometer-sized particles have novel optical, electronic, and structural properties that are not available from either individual molecules or bulk solids. When linked with tumor-targeting moieties, such as tumor-specific ligands or monoclonal antibodies, these nanoparticles can be used to target cancer-specific receptors, tumor antigens (biomarkers), and tumor vasculatures with high affinity and precision. The formulation and manufacturing process for cancer nanotherapy is disclosed in U.S. Pat. No. 7,179,484, and article M. N. Khalid, P. Simard, D. Hoarau, A. Dragomir, J. Leroux, Long Circulating Poly(Ethylene Glycol)Decorated Lipid Nanocapsules Deliver Docetaxel to Solid Tumors, Pharmaceutical Research, 23(4), 2006, all of which are herein incorporated by reference in their entireties.

RNA Therapy

RNA including but not limited to siRNA, shRNA, microRNA might be used to modulate gene expression and treat cancers. Double stranded oligonucleotides are formed by the assembly of two distinct oligonucleotide sequences where the oligonucleotide sequence of one strand is complementary to the oligonucleotide sequence of the second strand; such double stranded oligonucleotides are generally assembled from two separate oligonucleotides (e.g., siRNA), or from a single molecule that folds on itself to form a double stranded structure (e.g., shRNA or short hairpin RNA). These double stranded oligonucleotides have a feature in that each strand of the duplex has a distinct nucleotide sequence, wherein only one nucleotide sequence region (guide sequence or the antisense sequence) has complementarity to a target nucleic acid sequence and the other strand (sense sequence) comprises nucleotide sequence that is homologous to the target nucleic acid sequence.

MicroRNAs (miRNA) are single-stranded RNA molecules of about 21-23 nucleotides in length, which regulate gene expression. miRNAs are encoded by genes that are transcribed from DNA but not translated into protein (non-coding RNA); instead they are processed from primary transcripts known as pri-miRNA to short stem-loop structures called pre-miRNA and finally to functional miRNA. Mature miRNA molecules are partially complementary to one or more messenger RNA (mRNA) molecules, and their main function is to downregulate gene expression.

Certain RNA inhibiting agents might be utilized to inhibit the expression or translation of messenger RNA ("mRNA") that is associated with a cancer phenotype. Examples of such agents suitable for use herein include, but are not limited to, short interfering RNA ("siRNA"), ribozymes, and antisense oligonucleotides. Specific examples of RNA inhibiting agents suitable for use herein include, but are not limited to, Cand5, Sirna-027, fomivirsen, and angiozyme.

In some embodiments, a pharmaceutical composition, formulation, and/or dosage form of iniparib, or a pharmaceutically acceptable salt, solvate, metabolite, or prodrug thereof disclosed herein comprises one or more additional therapeutic agents. In some embodiments, the therapeutic agent is a stimulant, an antihistamine, an antiemetic, or an anti-cancer agent.

In some embodiments, the stimulant is selected from the group consisting of aminophylline, caffeine, dyphlline, oxitriphylline, theophhylline, amphetamine, benzphetamine, dextroamphetamine, diethylpropion, mazindol, methamphetamine, methylphenidate, dexmethylphenidate, pemoline, sibutramine, modafinil, atomoxetine, phendimetrizine, phenteramine, adrafinil, phenylpropanolamine, psuedoephedrine, synephrine, amphetaminil, furfenorex, or a combination thereof.

In some embodiments, the antiemetic is selected from the group consisting of aprepitant, dronabinol, perphenazine, palonosetron, trimethobenzamide, metoclopromide, domperidone, prochlorperazine, promethazine, chlorpromazine, trimethobenzamide, ondansetron, granisetron, hydroxyzine, acetylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxyperndyl, pipamazine, scopolamine, sulpiride, tetrahydrocannabinol, thiethylperazine, thioproperazine, tropisetron, droperidol, haloperidol, prochloperazine, metoclopramide, diphenhydramine, cannabis, midazolam, lorazepam, hyoscine, dexamethasone, emetrol, propofol and mixtures thereof.

In some embodiments, the antihistamine is selected from the group consisting of 2-(m-fluorophenyl)-histamine, chlorpheniramine, mepyramine, terfenadine, astemizole, tripolidine, ethanolamines carbinoxamine, diphenhydramine, doxylamine, pyrilamine, tripelennamine, hydroxyzine, fexofenadine, brompheniramine chlorpheniramine, cyproheptadine, loratadine, cetirizine, dimaprit, impromidine, amthamine, cimetidine, ranitidine, nizatidine, famotidine, R-alpha-methylhistamine, imetit, immepip, thioperamide, iodophenpropit, clobenpropit, clobenpropit, imetit, clozapine, thioperamide, azelastine, brompheniramine, carbinoxamine, cetrizine, chlorpheniramine, clemastine, cyclizine, cyproheptadine, desloratidine, dimenhydrinate, diphenhydramine, emedastine, fexofenadine, ketotifen, levocabastine, loratadine, meclizine, olopatadine, phenindamine, promethazine, or a combination thereof.

In some embodiments, the anticancer agent is selected from the group consisting of gemcitabine, carboplatin, paclitaxel, irinotecan, topotecan, temozolomide, picropodophyllin, and gefitinib.

Therapeutic Regimens

In some embodiments, the pharmaceutical compositions disclosed herein are administered for therapeutic applications. In some embodiments, the pharmaceutical composition is administered once per day, twice per day, three times per day or more. The pharmaceutical composition is administered daily, every day, every alternate day, five days a week, once a week, every other week, two weeks per month, three weeks per month, once a month, twice a month, three times per month, or more. The pharmaceutical composition is administered for at least 1 month, 2 months, 3 months, 4 months, 5 months, 6 months, 7 months, 8 months, 9 months, 10 months, 11 months, 12 months, 18 months, 2 years, 3 years, or more.

In some embodiments, one or more pharmaceutical compositions are administered simultaneously, sequentially, or at an interval period of time. In some embodiments, one or more pharmaceutical compositions are administered simultaneously. In some cases, one or more pharmaceutical compositions are administered sequentially. In additional cases, one or more pharmaceutical compositions are administered at an interval period of time (e.g., the first administration of a first pharmaceutical composition is on day one followed by an interval of at least 1, 2, 3, 4, 5, or more days prior to the administration of at least a second pharmaceutical composition).

In some embodiments, two or more different pharmaceutical compositions are co-administered. In some instances, the two or more different pharmaceutical compositions are co-administered simultaneously. In some cases, the two or more different pharmaceutical compositions are co-administered sequentially without a gap of time between administrations. In other cases, the two or more different pharmaceutical compositions are co-administered sequentially with a gap of about 0.5 hour, 1 hour, 2 hour, 3 hour, 12 hours, 1 day, 2 days, or more between administrations.

In the case wherein the patient's status does improve, upon the doctor's discretion the administration of the composition is given continuously; alternatively, the dose of the composition being administered is temporarily reduced or temporarily suspended for a certain length of time (i.e., a "drug holiday"). In some instances, the length of the drug holiday varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday is from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's conditions has occurred, a maintenance dose is administered if necessary. Subsequently, the dosage or the frequency of administration, or both, can be reduced, as a function of the symptoms, to a level at which the improved disease, disorder or condition is retained.

In some embodiments, the amount of a given agent that corresponds to such an amount varies depending upon factors such as the particular compound, the severity of the disease, the identity (e.g., weight) of the subject or host in need of treatment, but nevertheless is routinely determined in a manner known in the art according to the particular circumstances surrounding the case, including, e.g., the specific agent being administered, the route of administration, and the subject or host being treated. In some instances, the desired dose is conveniently presented in a single dose or as divided doses administered simultaneously (or over a short period of time) or at appropriate intervals, for example as two, three, four or more sub-doses per day.

The foregoing ranges are merely suggestive, as the number of variables in regard to an individual treatment regime is large, and considerable excursions from these recommended values are not uncommon. Such dosages is altered depending on a number of variables, not limited to the activity of the compound used, the disease or condition to be treated, the mode of administration, the requirements of the individual subject, the severity of the disease or condition being treated, and the judgment of the practitioner.

In some embodiments, toxicity and therapeutic efficacy of such therapeutic regimens are determined by standard pharmaceutical procedures in cell cultures or experimental animals, including, but not limited to, the determination of the LD50 (the dose lethal to 50% of the population) and the ED50 (the dose therapeutically effective in 50% of the population). The dose ratio between the toxic and therapeutic effects is the therapeutic index and it is expressed as the ratio between LD50 and ED50. Compounds exhibiting high therapeutic indices are preferred. The data obtained from cell culture assays and animal studies are used in formulating a range of dosage for use in human. The dosage of such compounds lies preferably within a range of circulating concentrations that include the ED50 with minimal toxicity. The dosage varies within this range depending upon the dosage form employed and the route of administration utilized.

Kits/Article of Manufacture

Disclosed herein, in certain embodiments, are kits and articles of manufacture for use with one or more of the pharmaceutical compositions, formulations, and/or dosage forms of iniparib, or a pharmaceutically acceptable salt, solvate, metabolite, or prodrug thereof and methods disclosed herein. Such kits include a carrier, package, or container that is compartmentalized to receive one or more containers such as vials, tubes, and the like, each of the container(s) comprising one of the separate elements to be used in a method disclosed herein. Suitable containers include, for example, bottles, vials, syringes, and test tubes. In one embodiment, the containers are formed from a variety of materials such as glass or plastic.

The articles of manufacture provided herein contain packaging materials. Examples of pharmaceutical packaging materials include, but are not limited to, blister packs, bottles, tubes, bags, containers, bottles, and any packaging material suitable for a selected formulation and intended mode of administration and treatment.

For example, the container(s) include a composition of iniparib or a pharmaceutically acceptable salt, solvate, metabolite, or prodrug thereof disclosed herein. Such kits optionally include an identifying description or label or instructions relating to its use in the methods disclosed herein.

A kit typically includes labels listing contents and/or instructions for use, and package inserts with instructions for use. A set of instructions will also typically be included.

In one embodiment, a label is on or associated with the container. In one embodiment, a label is on a container when letters, numbers or other characters forming the label are attached, molded or etched into the container itself; a label is associated with a container when it is present within a receptacle or carrier that also holds the container, e.g., as a package insert. In one embodiment, a label is used to indicate that the contents are to be used for a specific therapeutic application. The label also indicates directions for use of the contents, such as in the methods disclosed herein.

In certain embodiments, the pharmaceutical compositions are presented in a pack or dispenser device which contains one or more unit dosage forms comprising iniparib or a pharmaceutically acceptable salt, solvate, isomer, tautomer, metabolite, analog, or prodrug thereof. The pack, for example, contains metal or plastic foil, such as a blister pack. In one embodiment, the pack or dispenser device is accompanied by instructions for administration. In one embodiment, the pack or dispenser is also accompanied with a notice associated with the container in form prescribed by a governmental agency regulating the manufacture, use, or sale of pharmaceuticals, which notice is reflective of approval by the agency of the form of the drug for human or veterinary administration. Such notice, for example, is the labeling approved by the U.S. Food and Drug Administration for prescription drugs, or the approved product insert. In one embodiment, compositions comprising iniparib or a pharmaceutically acceptable salt, solvate, isomer, tautomer, metabolite, analog, or prodrug thereof formulated in a compatible pharmaceutical carrier are also prepared, placed in an appropriate container, and labeled for treatment of an indicated condition.

Definitions

Unless defined otherwise, all technical and scientific terms used herein have the same meaning as is commonly understood by one of skill in the art to which the claimed subject matter belongs. It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a", "an", and "the" include plural referents unless the context clearly dictates otherwise. In this application, the use of "or" means "and/or" unless stated otherwise. Furthermore, use of the term "including" as well as other forms, such as "include", "includes," and "included," is not limiting.

The section headings used herein are for organizational purposes only and are not to be construed as limiting the subject matter disclosed.

As used herein, the terms "individual(s)", "subject(s)" and "patient(s)" mean any mammal. In some embodiments, the mammal is a human. In some embodiments, the mammal is a non-human. None of the terms require or are limited to situations characterized by the supervision (e.g. constant or intermittent) of a health care worker (e.g. a doctor, a registered nurse, a nurse practitioner, a physician's assistant, an orderly or a hospice worker).

As used herein, ranges and amounts can be expressed as "about" a particular value or range. About also includes the exact amount. Hence "about 5 µL" means "about 5 µL" and also "5 µL." Generally, the term "about" includes an amount that would be expected to be within experimental error.

As used herein, the terms "analog", "chemical analog", and "structural analog" means a compound having a structure similar to the structure of another compound, but different from it in respect of a certain component or components. Analog can be different in one or more atoms, functional groups, or substructures of the molecule, which are replaced with other atoms, functional groups, or substructures. Despite similarity in chemical structure, analogs might have different physical, chemical, biochemical, and pharmacological properties.

"Chemotherapy" means the administration of one or more anti-cancer drugs such as, antineoplastic chemotherapeutic agents, chemopreventative agents, and/or other agents to a cancer patient by various methods, including intravenous, oral, intramuscular, intraperitoneal, intravesical, subcutaneous, transdermal, buccal, or inhalation or in the form of a suppository. Chemotherapy might be given prior to surgery to shrink a large tumor prior to a surgical procedure to remove it, after surgery or radiation therapy to prevent the growth of any remaining cancer cells in the body.

The terms "controlled-release dosage form" and "controlled-release layer" are used interchangeably and defined as those whose drug release characteristics of time course and/or location are chosen to accomplish therapeutic or convenience objectives not offered by conventional immediate-release dosage forms. The rate of release of the active drug from a controlled-release layer or dosage form is controlled by features of the dosage form and/or in combination with physiologic or environmental conditions rather than by physiologic or environmental conditions alone. The controlled-release dosage forms are used to maintain drug plasma levels within the therapeutic window. The controlled-release dosage forms of certain embodiments attempt to deliver therapeutically effective amounts of active drug as a once-daily dose so that the ratio Cmax/Cmin in the plasma at steady state is less than the therapeutic index, and to maintain drug levels at constant effective levels to provide a therapeutic benefit over a period of time (e.g. 24-hour period). In certain embodiments controlled-release dosage forms provide a substantially constant or gradually decreasing rate of drug release so as to provide plasma levels which remain substantially invariant with time. In certain embodiments controlled-release dosage forms are designed to provide a quick increase in the plasma concentration of the drug which remains substantially constant within the therapeutic range of the drug for a period of time (e.g. 24-hour period). Alternatively, in some other embodiments controlled-release dosage forms are designed to provide a quick increase in the plasma concentration of the drug, which although might not remain constant, declines at a rate such that the plasma concentration remains within the therapeutic range for a period of time (e.g. 24-hour period).

The term "controlled-release matrix" refers to a polymeric matrix that is capable of delivering a bioactive agent at a controlled rate for a period of time. Although there might be an initial burst phase, the overall release kinetics of the bioactive agent from the matrix are generally linear, such that a relatively constant supply of bioactive agent is released over the desired time period. The time period might vary from several hours to several days, depending upon the bioactive agent and its intended use. In general, it is preferable that the percentage of bioactive agent released from the controlled matrix over the treatment period be relatively high (e.g., at least about 50%, at least about 75%, at least about 90%, or at least about 95%) to avoid waste of unreleased bioactive agent.

The term "immediate-release" layer or dosage form refers to the release of an active agent substantially immediately upon administration. For example, immediate-release includes but not limited to contact with gastric juices and results in substantially complete dissolution within about 1 hour. Immediate-release components might also be referred to as instant release. When used in association with the dissolution profiles discussed herein, the term "immediate-release" refers to that portion of a dosage form disclosed herein which delivers active agent over a period of time less than 1 hour.

The terms "coating composition", "coat composition", "coating solution", "coat solution" "coating suspension", and "coat suspension" as used herein are used interchangeably and are defined to mean a mixture of excipients that is used to create a controlled-release coating. The coating composition is applied onto iniparib core to form an intermediate coating, and the intermediate coating is cured to form the controlled-release coating.

The terms "effective amount" or "pharmaceutically effective amount" refer to a nontoxic but sufficient amount of the agent to provide the desired biological, therapeutic, and/or prophylactic result. That result might be reduction and/or alleviation of the signs, symptoms, or causes of a disease, or any other desired alteration of a biological system. For example, an "effective amount" for therapeutic uses is the amount of iniparib or a salt, solvate, isomer, tautomer, metabolite, analog, or prodrug thereof as disclosed herein per se or a composition comprising iniparib or a salt, solvate, isomer, tautomer, metabolite, analog, or prodrug thereof as disclosed herein required to provide a clinically significant decrease in a disease. An appropriate effective amount in any individual case might be determined by one of ordinary skill in the art using routine experimentation.

The term "mucoadhesive agent" refers to an agent that adheres to a mucous membrane. The mucous membrane consists of one or more layers of epithelial cells overlying a layer of loose connective tissue. Examples of mucous membranes include, but not limited to, tongue mucosa, bronchial mucosa, endometrium, esophageal mucosa, gastric mucosa, intestinal mucosa, nasal mucosa, olfactory mucosa, oral mucosa, penile mucosa, vaginal mucosa, and anal mucosa.

The term "transmucosal administration" refers to the route of administration in which the drug is diffused through the mucous membrane. This might refer to inhalation, nasal, sublingual, vaginal, rectal, or ocular routes.

The term "median particle size" refers to the average diameter of the particle population. For particle size distributions, the median is called the D50. The D50 is the size in micrometers that splits the distribution with half above and half below this diameter. The Dv50 (or Dv0.5) is the median for a volume distribution.

"Pharmaceutically acceptable," as used herein, refers a material, such as a carrier or diluent, which does not abrogate the biological activity or properties of the compound, and is relatively nontoxic, i.e., the material is administered to an individual without causing undesirable biological effects or interacting in a deleterious manner with any of the components of the composition in which it is contained.

The term "pharmaceutically acceptable salt" refers to a form of a therapeutically active agent that consists of a cationic form of the therapeutically active agent in combination with a suitable anion, or in alternative embodiments, an anionic form of the therapeutically active agent in combination with a suitable cation. Handbook of Pharmaceutical Salts: Properties, Selection and Use. International Union of Pure and Applied Chemistry. Wiley-VCIH 2002. S. M. Berge, L. D. Bighley, D. C. Monkhouse, J. Pharm. Sci. 1977, 66, 1-19. P. H. Stahl and C. G. Wermuth, editors, *Handbook of Pharmaceutical Salts: Properties, Selection and Use*, Weinheim/Zürich:Wiley-VCH/VHCA 2002. Pharmaceutical salts typically are more soluble and more rapidly soluble in stomach and intestinal juices than non-ionic species and so are useful in solid dosage forms. Furthermore, because their solubility often is a function of pH, selective dissolution in one or another part of the digestive tract is possible and this capability can be manipulated as one aspect of delayed and sustained release behaviors. Also, because the salt-forming molecule can be in equilibrium with a neutral form, passage through biological membranes can be adjusted.

In some embodiments, pharmaceutically acceptable salts are obtained by reacting a compound described herein with an acid to provide a "pharmaceutically acceptable acid addition salt." In some embodiments, the compound described herein (i.e. free base form) is basic and is reacted with an organic acid or an inorganic acid. Inorganic acids include, but are not limited to, hydrochloric acid, hydrobromic acid, metaphosphoric acid, nitric acid, phosphoric acid, and sulfuric acid. Organic acids include, but are not limited to, 1-hydroxy-2-naphthoic acid; 2,2-dichloroacetic acid; 2-hydroxyethanesulfonic acid; 2-oxoglutaric acid; 4-acetamidobenzoic acid; 4-aminosalicylic acid; acetic acid; adipic acid; ascorbic acid (L) aspartic acid (L); benzenesulfonic acid; benzoic acid; camphoric acid (+); camphor-10-sulfonic acid (+); capric acid (decanoic acid); caproic acid (hexanoic acid); caprylic acid (octanoic acid); carbonic acid; cinnamic acid; citric acid; cyclamic acid; dodecylsulfuric acid; ethane-1,2-disulfonic acid; ethanesulfonic acid; formic acid; fumaric acid; galactaric acid; gentisic acid; glucoheptonic acid (D); gluconic acid (D); glucuronic acid (D); glutamic acid; glutaric acid; glycerophosphoric acid; glycolic acid; hippuric acid; isobutyric acid; lactic acid (DL); lactobionic acid; lauric acid: maleic acid, malic acid (−L); malonic acid; mandelic acid (DL); methanesulfonic acid; monomethyl fumarate, naphthalene-1,5-disulfonic acid; naphthalene-2-sulfonic acid; nicotinic acid; oleic acid; oxalic acid; palmitic acid; pamoic acid; proprionic acid; pyroglutamic acid (−L); salicylic acid; sebacic acid; stearic acid; succinic acid; sulfuric acid; tartaric acid (+L); thiocyanic acid; toluenesulfonic acid (o); and undecylenic acid.

In some embodiments, a compound described herein is prepared as a chloride salt, sulfate salt, bromide salt, mesylate salt, maleate salt, citrate salt or phosphate salt.

In some embodiments, pharmaceutically acceptable salts are obtained by reacting a compound described herein with a base to provide a "pharmaceutically acceptable base addition salt". In some embodiments, the compound described herein is acidic and is reacted with a base. In such situations, an acidic proton of the compound described herein is replaced by a metal ion, e.g., lithium, sodium, potassium, magnesium, calcium, or an aluminum ion. In some cases, compounds described herein coordinate with an organic base, such as, but not limited to, ethanolamine, diethanolamine, triethanolamine, tromethamine, meglumine, N-methylglucamine, dicyclohexylamine, tris(hydroxymethyl)methylamine. In other cases, compounds described herein form salts with amino acids such as, but not limited to, arginine, lysine, and the like. Acceptable inorganic bases used to form salts with compounds that include an acidic proton, include, but are not limited to, aluminum hydroxide, calcium hydroxide, potassium hydroxide, sodium carbonate, potassium carbonate, sodium hydroxide, lithium hydroxide, and the like. In some embodiments, the compounds provided herein are prepared as a sodium salt, calcium salt, potassium salt, magnesium salt, meglumine salt, N-methylglucamine salt or ammonium salt.

It should be understood that a reference to a pharmaceutically acceptable salt includes the solvent addition forms, i.e. solvates. In some embodiments, solvates contain either stoichiometric or non-stoichiometric amounts of a solvent, and are formed during the process of isolating or purifying the compound with pharmaceutically acceptable solvents such as water, ethanol, and the like. Hydrates are formed when the solvent is water, or alcoholates are formed when the solvent is alcohol. Solvates of compounds described herein are conveniently prepared or formed during the processes described herein. In addition, the compounds provided herein optionally exist in unsolvated as well as solvated forms.

The methods and formulations described herein include the use of N-oxides (if appropriate), crystalline forms (also known as polymorphs), or pharmaceutically acceptable salts of compounds described herein, as well as active metabolites of these compounds having the same type of activity.

In some embodiments, sites on the organic radicals (e.g. alkyl groups, aromatic rings) of compounds described herein are susceptible to various metabolic reactions. Incorporation of appropriate substituents on the organic radicals will reduce, minimize or eliminate this metabolic pathway. In specific embodiments, the appropriate substituent to decrease or eliminate the susceptibility of the aromatic ring to metabolic reactions is, by way of example only, a halogen, deuterium, an alkyl group, a haloalkyl group, or a deuteroalkyl group.

In another embodiment, the compounds described herein are labeled isotopically (e.g. with a radioisotope) or by another other means, including, but not limited to, the use of chromophores or fluorescent moieties, bioluminescent labels, or chemiluminescent labels.

Compounds described herein include isotopically-labeled compounds, which are identical to those recited in the various formulae and structures presented herein, but for the fact that one or more atoms are replaced by an atom having an atomic mass or mass number different from the atomic mass or mass number usually found in nature. Examples of isotopes that can be incorporated into the present compounds include isotopes of hydrogen, carbon, nitrogen, oxygen, fluorine and chlorine, such as, for example, $^{2}H$, $^{3}H$, $^{13}C$, $^{14}C$, $^{15}N$, $^{18}O$, $^{17}O$, $^{35}S$, $^{18}F$, $^{36}Cl$. In one aspect, isotopically-labeled compounds described herein, for example those into which radioactive isotopes such as $^{3}H$ and $^{14}C$ are incorporated, are useful in drug and/or substrate tissue distribution assays. In one aspect, substitution with isotopes such as deuterium affords certain therapeutic advantages resulting from greater metabolic stability, such as, for example, increased in vivo half-life or reduced dosage requirements. In some embodiments, one or more hydrogen atoms of the compounds described herein is replaced with deuterium.

In some embodiments, the compounds described herein possess one or more stereocenters and each stereocenter exists independently in either the R or S configuration. The compounds presented herein include all diastereomeric, enantiomeric, atropisomers, and epimeric forms as well as the appropriate mixtures thereof. The compounds and methods provided herein include all cis, trans, syn, anti, entgegen (E), and zusammen (Z) isomers as well as the appropriate mixtures thereof.

Individual stereoisomers are obtained, if desired, by methods such as, stereoselective synthesis and/or the separation of stereoisomers by chiral chromatographic columns. In certain embodiments, compounds described herein are prepared as their individual stereoisomers by reacting a racemic mixture of the compound with an optically active resolving agent to form a pair of diastereoisomeric compounds/salts, separating the diastereomers and recovering the optically pure enantiomers. In some embodiments, resolution of enantiomers is carried out using covalent diastereomeric derivatives of the compounds described herein. In another embodiment, diastereomers are separated by separation/resolution techniques based upon differences in solubility. In other embodiments, separation of stereoisomers is performed by chromatography or by the forming diastereomeric salts and separation by recrystallization, or chromatography, or any combination thereof. Jean Jacques, Andre Collet, Samuel H. Wilen, "Enantiomers, Racemates and Resolutions", John Wiley And Sons, Inc., 1981. In some embodiments, stereoisomers are obtained by stereoselective synthesis.

In some embodiments, compounds described herein are prepared as prodrugs. A "prodrug" refers to an agent that is converted into the parent drug in vivo. Prodrugs are often useful because, in some situations, they are easier to administer than the parent drug. They are, for instance, bioavailable by oral administration whereas the parent is not. The prodrug might be a substrate for a transporter. Further or alternatively, the prodrug also has improved solubility in pharmaceutical compositions over the parent drug. In some embodiments, the design of a prodrug increases the effective water solubility. An example, without limitation, of a prodrug is a compound described herein, which is administered as an ester (the "prodrug") but then is metabolically hydrolyzed to provide the active entity. A further example of a prodrug is a short peptide (polyaminoacid) bonded to an acid group where the peptide is metabolized to reveal the active moiety. In certain embodiments, upon in vivo administration, a prodrug is chemically converted to the biologically, pharmaceutically or therapeutically active form of the compound. In certain embodiments, a prodrug is enzymatically metabolized by one or more steps or processes to the biologically, pharmaceutically or therapeutically active form of the compound.

Prodrugs of the compounds described herein include, but are not limited to, esters, ethers, carbonates, thiocarbonates, N-acyl derivatives, N-acyloxyalkyl derivatives, quaternary derivatives of tertiary amines, N-Mannich bases, Schiff bases, amino acid conjugates, phosphate esters, and sulfonate esters. See for example Design of Prodrugs, Bundgaard, A. Ed., Elseview, 1985 and Method in Enzymology, Widder, K. et al., Ed.; Academic, 1985, vol. 42, p. 309-396; Bundgaard, H. "Design and Application of Prodrugs" in A Textbook of Drug Design and Development, Krosgaard-Larsen and H. Bundgaard, Ed., 1991, Chapter 5, p. 113-191; and Bundgaard, H., Advanced Drug Delivery Review, 1992, 8, 1-38, each of which is incorporated herein by reference. In some embodiments, a hydroxyl group in the compounds disclosed herein is used to form a prodrug, wherein the hydroxyl group is incorporated into an acyloxyalkyl ester, alkoxycarbonyloxyalkyl ester, alkyl ester, aryl ester, phosphate ester, sugar ester, ether, and the like. In some embodiments, a hydroxyl group in the compounds disclosed herein is a prodrug wherein the hydroxyl is then metabolized in vivo to provide a carboxylic acid group. In some embodiments, a carboxyl group is used to provide an ester or amide (i.e. the prodrug), which is then metabolized in vivo to provide a carboxylic acid group. In some embodiments, compounds described herein are prepared as alkyl ester prodrugs.

Prodrug forms of the herein described compounds, wherein the prodrug is metabolized in vivo to produce a compound described herein as set forth herein are included within the scope of the claims. In some cases, some of the herein-described compounds is a prodrug for another derivative or active compound.

In additional or further embodiments, the compounds described herein are metabolized upon administration to an organism in need to produce a metabolite that is then used to produce a desired effect, including a desired therapeutic effect.

A "metabolite" of a compound disclosed herein is a derivative of that compound that is formed when the compound is metabolized. The term "active metabolite" refers to a biologically active derivative of a compound that is formed when the compound is metabolized. The term "metabolized," as used herein, refers to the sum of the processes (including, but not limited to, hydrolysis reactions and reactions catalyzed by enzymes) by which a particular substance is changed by an organism. Thus, enzymes might produce specific structural alterations to a compound. For example, cytochrome P450 catalyzes a variety of oxidative and reductive reactions while uridine diphosphate glucuronyltransferases catalyze the transfer of an activated glucuronic-acid molecule to aromatic alcohols, aliphatic alcohols, carboxylic acids, amines and free sulphydryl groups. Metabolites of the compounds disclosed herein are optionally identified either by administration of compounds to a host and analysis of tissue samples from the host, or by incubation of compounds with hepatic cells in vitro and analysis of the resulting compounds.

A compound is "dissolved" when it is "in solution", and does not spontaneously come out of solution to from a separate phase. In order to be dissolved, the compound need not dissociate completely on a molecular level, but must remain in solution so as to be effective in treatment of a disease or condition. A dissolved compound might be present in a micellar, emulsified, or liposomal form.

"Solubility" generally means the amount of a compound dissolved in a solvent. Suitable solvents include aqueous and non-aqueous solvents.

"Poor solubility" means a small amount of compound dissolved in a solvent. Poor solubility is not an absolute term, but depends on the amount of the compound that is needed for effective treatment of a disease or condition. A compound will be poorly soluble if its solubility is lower than is desired in order for an effective treatment of a disease or condition.

"Enhanced solubility" means higher solubility than for iniparib alone. Enhanced solubility in water can be useful because many bodily fluids such as blood are water based (aqueous) and therefore, a more water soluble drug might have higher bioavailability. While the exact solubility of a compound in pure water is not the same as in an aqueous solution such as blood, a composition's solubility in pure water is often a good indication of solubility in other aqueous solutions.

"Surgery" means any therapeutic or diagnostic procedure that involves methodical action of the hand or of the hand with an instrument, on the body of a human or other mammal, to produce a curative, remedial, or diagnostic effect.

"Radiation therapy" means exposing a patient to high-energy radiation, including without limitation x-rays, gamma rays, and neutrons. This type of therapy includes without limitation external-beam therapy, internal radiation therapy, implant radiation, brachytherapy, systemic radiation therapy, and radiotherapy.

A "tautomer" refers to a proton shift from one atom of a molecule to another atom of the same molecule. The compounds presented herein might exist as tautomers. Tautomers are compounds that are interconvertible by migration of a hydrogen atom, accompanied by a switch of a single bond and adjacent double bond. In bonding arrangements where tautomerization is possible, a chemical equilibrium of the tautomers will exist. All tautomeric forms of the compounds disclosed herein are contemplated. The exact ratio of the tautomers depends on several factors, including temperature, solvent, and pH. Some examples of tautomeric interconversions include:

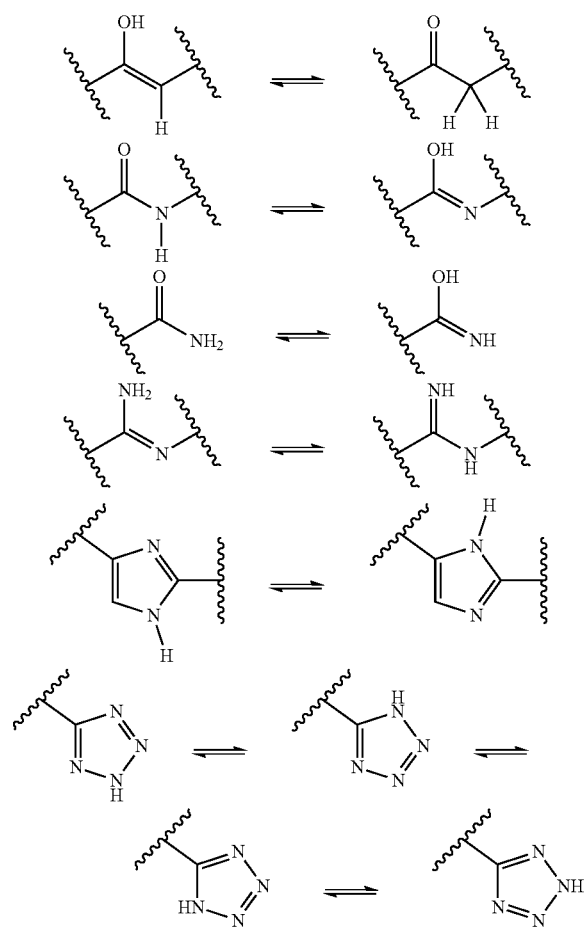

The term "treating" and its grammatical equivalents as used herein include achieving a therapeutic benefit and/or a prophylactic benefit. By therapeutic benefit is meant eradication or amelioration of the underlying disorder being treated. For example, in a cancer patient, therapeutic benefit includes eradication or amelioration of the underlying cancer. Also, a therapeutic benefit is achieved with the eradication or amelioration of one or more of the physiological symptoms associated with the underlying disorder such that an improvement is observed in the patient, notwithstanding the fact that the patient might still be afflicted with the underlying disorder. For prophylactic benefit, a method might be performed on, or a composition might be administered to a patient at risk of developing cancer, or to a patient reporting one or more of the physiological symptoms of such conditions, even though a diagnosis of the condition might not have been made.

While generally high drug solubility is desired, is would be appreciated by a person of ordinary skill in the art that there are other considerations in creating a pharmaceutical composition such as viscosity, stability, potential toxicity, etc. that might result a composition with lower solubility being more desirable for a particular therapy or delivery method as long as the amount of available drug is enough for the application. Pharmaceutical compositions disclosed herein provide the ability to optimize these factors.

It has been reported that nitrobenzamide compounds have selective cytotoxicity upon malignant cancer cells but not upon nonmalignant cancer cells. See Rice et at., Proc. Natl. Acad. Sci. USA 89:7703-7707 (1992). In one embodiment, the pharmaceutical compositions disclosed herein might exhibit more selective toxicity towards tumor cells than non-tumor cells.

It has been reported that the tumorgenicity of nitrobenzamide and nitrososbenzamide compounds is enhanced when buthionine sulfoximine BSO is co-administered to cancer cells. See Mendeleyev et al., *Biochemical Pharmacol.* 50(5): 705-714 (1995). Buthionine sulfoximine (BSO) inhibits gamma-glutamylcysteine sythetase, a key enzyme in the biosynthesis of glutathione, which is responsible in part for cellular resistance to chemotherapy. See Chen et al., *Chem Biol Interact*. April 24; 111-112:263-75 (1998). Disclosed herein are pharmaceutical compounds useful for treating cancer via the administration of iniparib formulation in combination with BSO.

Poly (ADP-ribose) polymerase (PARP) is an essential enzyme in DNA repair, thus playing a potential role in chemotherapy resistance. Targeting PARP can interrupt DNA repair, thereby enhancing antineoplastic chemotherapeutic agent mediated-, topoisomerase inhibitor-mediated, and growth factor receptor inhibitor, e.g. IGF1R inhibitor-mediated DNA replication and/or repair in cancer cells.

Examples

These examples are provided for illustrative purposes only and not to limit the scope of the claims provided herein.

In iparib or a pharmaceutically acceptable salt, solvate, metabolite, or prodrug thereof is micronized in a spiral jet mill. Feed pressure and grind pressure are adjusted to obtain micronized iniparib or a pharmaceutically acceptable salt, solvate, metabolite, or prodrug thereof with a median particle size from about 15 µm to about 350 µm.

Median particle size of iniparib or a pharmaceutically acceptable salt, solvate, metabolite, or prodrug thereof is measured as follows. A wet dispersion method is employed for the particle size analysis. Water is used as a dispersant. 5 drops of igepal solution (20% v/v) is added to the dispersion unit as a surfactant. The stirrer speed is set to 2500 rpm and a background measurement is acquired. Once the sample has been added to the dispersion unit a measurement delay is employed prior to sample measurement. For the non-micronized and micronized iniparib or a pharmaceutically acceptable salt, solvate, metabolite, or prodrug thereof different measurement delays are employed to ensure adequate dispersion of the compound within the dispersion unit. Two minute and five minute measurement delays are employed for the non-micronized and micronized compound, respectively. For each aliquot of the compound added to the dispersion unit, triplicate particle size measurements are made and the average results are quoted.

Example 1. Solid Oral Formulation of Iniparib

Pharmaceutical composition 1.1: 100.0 g of micronized iniparib or a pharmaceutically acceptable salt, solvate, metabolite, or prodrug thereof with a median particle size from about 20 µm to about 400 µm is mixed with 44.4 g of pregelatinized starch, 33.3 g of microcrystalline cellulose, 4.4 g of polyvinylpyrrolidone, and 4.4 g of sodium starch glycollate. The mixture is blended for about 10 minutes. The resulted pharmaceutical composition is formulated into a suitable dosage form.

Pharmaceutical composition 1.2: 100.0 g of micronized iniparib or a pharmaceutically acceptable salt, solvate, metabolite, or prodrug thereof with a median particle size from about 20 μm to about 400 μm is mixed with 114.0 g of pregelatinized starch, 71.3 g of microcrystalline cellulose, 8.6 g of polyvinylpyrrolidone, and 17.2 g of sodium starch glycollate. The mixture is blended for about 10 minutes. The resulted pharmaceutical composition is formulated into a suitable dosage form.

Pharmaceutical composition 1.3: about 100 g of micronized iniparib or a pharmaceutically acceptable salt, solvate, metabolite, or prodrug thereof with a median particle size from about 20 μm to about 400 μm is mixed with 81.3 g of pregelatinized starch, 50.0 g of microcrystalline cellulose, 6.3 g of polyvinylpyrrolidone, and 5.0 g of sodium starch glycollate. The mixture is blended for about 10 minutes. The resulted pharmaceutical composition is formulated into a suitable dosage form.

Pharmaceutical composition 1.4: about 100 g of micronized iniparib or a pharmaceutically acceptable salt, solvate, metabolite, or prodrug thereof with a median particle size from about 20 μm to about 400 μm is mixed with 78.8 g of pregelatinized starch, 50.0 g of microcrystalline cellulose, 6.3 g of polyvinylpyrrolidone, 5.0 g of sodium starch glycollate, and 2.5 g sodium lauryl sulfate. The mixture is blended for about 10 minutes. The resulted pharmaceutical composition is formulated into a suitable dosage form.

Example 2. Controlled-Release Solid Dosage Form

A controlled-release solid dosage form of iniparib 500 mg tablet is prepared as follows.

| Ingredient | % w/w |
|---|---|
| Iniparib HCl | 94.20 |
| Silicon dioxide | 0.70 |
| Polyvinyl alcohol (PVA)* | 2.00 |
| Atomized glyceryl behenate | 2.30 |
| Magnesium stearate | 0.80 |
| Total | 100.00 |

*The PVA is prepared as a 4% solution (w/w) in purified water. The purified water is not considered as part of the theoretical batch size since it is evaporated during drying of the core in the fluid bed granulator.

All of the iniparib and silicon dioxide is transferred to a V-blender and blended for about 10 minutes. The blended material is then discharged into a fluid bed granulator and granulation is carried out in the presence of the PVA solution.

After drying, the granules are sized by passing the granules through a 0.40 mm screen. The screened granules are then transferred to a V-blender and blended with the atomized glyceryl behenate for about 10 minutes. Finally, the magnesium stearate is added and blending is carried out for about 10 more minutes.

The iniparib tablet cores are then coated with a controlled-release coating formulation. The coating process is carried out in an apparatus equipped with a coating chamber. The mesh size of the bottom screen is 200 m and the size of the spray nozzle is 1 mm.

Coated tablets are dried for about 30 minutes. After application of the coating the tablets are cured in an oven at 62±2° C. for about 2 hours.

The iniparib tablet cores are next coated with the coating formulation to a weight gain of either 14% or 16% w/w by weight of the tablet core and cured in an oven at between about 60° C. to about 75° C. for between about 2 hours to about 15 hours.

The resulted iniparib core coated with a controlled-release layer is further coated with an immediate-release layer comprising 15.0 mg of promethazine hydrochloride.

Example 3. Controlled-Release Matrix of Iniparib

A controlled-release matrix containing iniparib is prepared as follows.

A mixture of 25% iniparib or a pharmaceutically acceptable salt, solvate, metabolite, or prodrug thereof (such as iniparib HCl) is combined with a polymeric matrix such as poly(lactic-co-glycolic acid) polymer (PLGA) and melt extruded using a twin screw extruder (available from American LEISTRITZ Extruder Corp. USA, Somerville, N.J. 08876). Iniparib is fed in a continuous manner to the twin screw extruder from a loss-in-weight feeder (available from K-Iron. International, Inc., Pitman, N.J. 08071). The polymeric matrix is fed in a similar manner. The ratio of the bioactive agent to the polymeric matrix is controlled by the relative mass flow rate of bioactive agent from the first feeder to that of the polymeric matrix from the second feeder. The feeders and extruder are purged with dry air or nitrogen gas to maintain low humidity. The polymeric matrix is melted within the extruder operating at a temperature of 120° C. Iniparib is not melted but is mixed within the molten and flowing polymeric matrix. The extruder forces or pumps the mixed bioactive agent and polymeric matrix through a rectangular shaped orifice or die to shape the material into an extrudate with width of between about 5 mm and about 10 mm and a thickness between about 50 m and about 250 m. After cooling, the extrudate is cut into strips with a desired length and packaged. The individual strips are placed and sealed inside of a sterilization pouch such as foil-foil pouch (available from 445 Sixth Street, NW, Grand Rapids, Mich. 49504 USA).

Example 4. Oral Liquid Formulation of Iniparib

A stable iniparib oral liquid formulation is prepared according to a process comprising mixing a first mixture with a second mixture;
the first mixture comprising:
 (a) a pharmaceutically acceptable salt of iniparib;
 (b) a surfactant; and
 (c) water; and
the second mixture comprising:
 (a) a buffer;
 (b) optionally one or more agents selected from the group consisting of flavoring agents, sweetening agents, suspensions aids, preservatives; and antifoaming agents; and
 (c) water.
The first mixture is obtained by a process comprising adding water to a first container; adding a water soluble salt of iniparib to the first container; adding a surfactant to the first container; and stirring for 15 minutes. The second mixture is obtained by a process comprising adding water to a second container; adding a buffer to a second container; adding a sweetening agent to a second container; adding a flavoring agent to a second container; adding an antifoaming agent to a second container; adding suspension aids to a second container; and stirring for 10 minutes.

A stable iniparib oral liquid formulation is prepared according to a process comprising mixing a first mixture with a second mixture;

the first mixture comprising:
(a) iniparib hydrobromide;
(b) poloxamer 188; and
(c) water; and the second mixture comprising:
(a) a phosphate buffer;
(b) optionally one or more agents selected from the group consisting of flavoring agents, sweetening agents, suspensions aids, preservatives; and antifoaming agents; and
(c) water.

Example 5. Transmucosal Delivery of Iniparib Compositions

Pharmaceutical composition for the nasal transmucosal delivery containing iniparib, or a pharmaceutically acceptable salt, solvate, metabolite, or prodrug thereof is formulated into a suitable form, and administered by spray as a medicine for external use.

For preparation of spray, iniparib or a pharmaceutically acceptable salt, solvate, metabolite, or prodrug thereof (such as iniparib HCl) is dissolved in a solvent (such as water, ethylene glycol, or glycerin), or suspended. The concentration of iniparib or a pharmaceutically acceptable salt, solvate, metabolite, or prodrug thereof in the solution is from about 5 mg/mL to about 50 mg/mL. To the resulted solution, a mucoadhesive agent is added (such as Carbopol 974P). The concentration of the mucoadhesive agent in the resulted mixture is from about 1 mg/mL to about 25 mg/mL. The resulted medicinal solution is filled in a container having a specific spraying device (valve) with a low viscous spraying agent. For this, the medicinal solution is sprayed in the type of smog using pressure. A dose of the pharmaceutical compositions containing iniparib, or a pharmaceutically acceptable salt, solvate, metabolite, or prodrug thereof is 0.1 mg-10 mg/kg/day, and is altered according to the composition used and/or patient's condition.

Example 6. Preparation of a Thermoreversible Gel Iniparib Formulation

| Ingredient | Quantity (mg/g of formulation) |
|---|---|
| Iniparib | 20.0 |
| methylparaben | 1.0 |
| HPMC | 10.0 |
| Poloxamer 407 | 180.0 |
| TRIS HCl buffer (0.1M) | 789.0 |

A 10-g batch of gel formulation containing 2.0% of iniparib is prepared by suspending 1.80 g of Poloxamer 407 (BASF Corp.) in 5.00 g of TRIS HCl buffer (0.1 M) and the components are mixed tinder agitation overnight at 4° C. to ensure complete dissolution. Iniparib (200.0 tug), hydroxvpropylinethylcellulose (100.0 mg), methlviparaben (10 mg) and additional TRIS HCl buffer (0.1 M) (2.89 g) is added and further stirring allowed until dissolution is observed. The mixture is maintained below room temperature until use.

Example 7. Preparation of Liposomal Iniparib Formation

| Ingredient | Quantity (mg/g of cream) |
|---|---|
| Iniparib | 5.0 |
| soya lecithin | 200.0 |
| cholesterol | 20.0 |
| tetraglycol | 100.0 |
| dimethylisosorbide | 50.0 |
| methylparaben | 2.0 |
| propylparaben | 0.2 |
| BHT | 0.1 |
| sodium chloride | 1.0 |
| HPMC | 15.0 |
| sodium hydroxide | 0.6 |
| citric acid | 1.0 |
| purified water, USP | 603.6 |

Heat the soya lecithin, tetraglycol and dimethyl isosorbide to about 70-75° C. Dissolve the iniparib, cholesterol and butylated hydroxytoluene in the heated mixture. Stir until complete dissolution is obtained. Heat about one third of the water to 80-95° C. in a separate vessel and dissolve the preservatives methylparaben and propylparaben in the heated water while stirring. Allow the solution to cool to about 25° C. and then add the disodium edetate, sodium chloride, sodium hydroxide and citric acid. Add the remainder of the water and stir to obtain a complete solution. Transfer the organic mixture into the aqueous mixture by means of a vacuum, while homogenizing the combination with a high-shear mixer until a homogeneous product is obtained. Add the hydroxypropyl methylcellulose into the biphasic mixture by means of a vacuum while homogenizing with a mixer. The homogenizer is a Silverson high-shear mixer operating at approximately 3000 rpm. Single bilayered liposomes are formed. The white lipogel cream is ready for use.

Example 8. Preparation of an Iniparib Nanoparticle Formulation 750 mg (15 mg/ml theoretical) of a diblock copolymer consisting of the combination of a poly(d,l-lactic acid) of mass 30 kD and of a polyethylene glycol of mass 2 kD (PLA-PEG) and 250 mg (5 mg/ml theoretical) of iniparib is dissolved in 20 ml of ethyl acetate (solution A). 175 mg of lecithin E80 and 90 mg of sodium oleate is dispersed in 50 nil of 5% w/v glucose solution (solution B). Solution A is emulsified in solution B with an Ultra-turrax stirrer and the pre-emulsion is then introduced into a Microfluidizer 110 S® type homogenizer for 10 minutes at 10° C. The volume of emulsion recovered is about 70 ml (70 g). The ethyl acetate is removed using a rotary evaporator at reduced pressure (100 mm of mercury) to a suspension volume of about 45 ml (45 g).

Example 9. Preparation of a Mucoadhesive, Thermoreversible Gel Iniparib Formulation

| Ingredient | Quantity (mg/g of formulation) |
|---|---|
| Iniparib | 20.0 |
| methylparaben | 1.0 |
| HPMC | 10.0 |
| Carbopol 934P | 2.0 |

| Ingredient | Quantity (mg/g of formulation) |
|---|---|
| Poloxamer 407 | 180.0 |
| TRIS HCl buffer (0.1M) | 787.0 |

A 10-g batch of mucoadhesive, gel formulation containing 2.0% of iniparib is prepared by suspending 2.0 mg of Carbopol 934P and 1.80 g of Poloxamer 407 (BASF Corp.) in 5.00 g of TRIS HCl buffer (0.1 M) and the components are mixed under agitation overnight at 4° C. to ensure complete dissolution. The iniparib (200.0 mg), hydroxypropylmethylcellulose (100.0 mg), methylparaben (10 mg) and additional TRIS HCl buffer (0.1 M) (2.87 g) are added and further stirring allowed until complete dissolution is observed. The mixture is maintained below room temperature until use.

Example 10. Preparation of a 10% Iniparib 95:5 d,l-PLGA Microsphere Formulation Ninety grams (90 g) of 95:5 d,l-PLGA and 10 g of iniparib are codissolved in 400 g ethyl acetate in an Erlemeyer flask at 52° C. The drug/polymer solution is added to a 2000 ml glass jacketed reactor containing 550 g of 5% aqueous polyvinyl alcohol containing 9.7 g of ethyl acetate. Reactor contents are stirred with an overhead stir motor and the temperature is maintained at 52° C., by a circulating bath. The emulsion size is monitored by light microscopy and the stirring is stopped when the particle size is found to be in the desired size range (less than 300 microns) usually after about 2 minutes. The stir speed is reduced to avoid further size reduction of the sterilized emulsion. After stirring for a total of 4 minutes, the reactor contents are pressure-transferred into 40 liters of water at 12° C. After stirring for 20 minutes, the hardened microspheres are isolated and the product then transferred into 20 liters of water at 12° C. After approximately 3 hours, the second wash is transferred onto a sieve stack composed of 25, 45, 90, 150, and 212 micron openings. The product on the sieves is washed with copious amounts of cold water to separate the different sizes of microspheres. After drying on the sieves overnight, the different fractions are collected and drying is continued tinder vacuum at room temperature. Formulations with other drug levels are prepared by simply adjusting the polymer/drug ratio.

Example 11. Preparation of a 10% Iniparib 65:35 d,l-PLGA Microsphere Formulation Microspheres are produced by the method of Example 10 except that a different biodegradable polymer matrix is utilized. A 65:35 d,l-PLGA polymer is used in place of the 95:5 polymer indicated in Example 10.

Example 12. Preparation of a Mucoadhesive, Cyclodextrin-based Iniparib Formulation

| Ingredient | Quantity (mg/g of formulation) |
|---|---|
| Iniparib | 20.0 |
| HP☐CD | 500 |
| propylene glycol | 50 |
| paraffin oil | 200 |
| trihydroxystearate | 10 |
| cetyl dimethicon copolyol | 30 |
| water | qs ad 1000 |
| phosphate buffer pH 7.4 | qs pH 7.4 |

The cream-type formulation is prepared by solubilizing iniparib with propylene glycol and this solution is added to a suspension of HP☐CD in water. A second system is prepared by mixing paraffin oil, trihydroxystearate and cetyl dimethicon copolyol with warming to 60° C. Upon cooling to room temperature, the lipid system is mixed with the aqueous phase in a homogenizer for 30 minutes.

Example 13. Preparation of a Gel Iniparib Formulation

| Ingredient | Quantity (mg/g of formulation) |
|---|---|
| Iniparib | 20.0 |
| chitosan | 20.0 |
| Glycerophosphate disodium | 80.0 |
| water | 880 |

A 5 ml solution of acetic acid is titrated to a pH of about 4.0. The chitosan is added to achieve a pH of about 5.5. The iniparib is then dissolved in the chitosan solution. This solution is sterilized by filtration. A 5 ml aqueous solution of glycerophosphate disodium is also prepared and sterilized. The two solutions are mixed and within 2 h at 37° C. the desired gel is formed.

Example 14. Preparation of a Gel/Liposome Iniparib Formulation

| Ingredient | Quantity |
|---|---|
| Iniparib | 20.0 mg/g |
| Liposomes | 15 umol/ml |
| Chitosan-Glycerophosphate | 100.0 mg/g |

The liposomes are prepared in the presence of the iniparib by the reversed-phase evaporation method, where lipids in chloroform or chloroform-methanol (2:1, v/v) are deposited on the sides of a tube by evaporation of the organic solvent. The lipid film is redissolved in diethyl ether and the aqueous phase (pH 7.4 300 mOsm/kg) containing 20 mM Hepes and 144 mM NaCl is added. The mixture is sonicated to obtain a homogeneous emulsion, and then the organic solvent is removed under vacuum. The preparation is extruded to obtain the required liposome size and free components removed by size-exclusion chromatography using a Sephadex G-50 column (Amersham Pharmacia Biotech, Uppsala, Sweden).

To prepare the chitosan-glycerophosphate formulation, a 5 ml solution of acetic acid is titrated to a pH of about 4.0. The chitosan is added to achieve a pH of about 5.5. This solution is sterilized by Filtration, A 5 ml aqueous solution of glycerophosphate disodium is also prepared and sterilized. The two solutions are mixed and within 2 h at 37° C., and the desired gel is formed. The chitosan-glycerophosphate solution is gently mixed with the liposomes at room temperature, Embodiment 1: an oral dosage form comprising an immediate-release top layer and a controlled-release core, wherein said immediate-release layer comprises at least one of the stimulant, antihistamine, or antiemetic; and the controlled-release layer comprising a therapeutically effective amount of a formulation, comprising:
  (i) iniparib or a pharmaceutically acceptable salt, solvate, metabolite, or prodrug thereof;
  (ii) at least one pharmaceutically acceptable excipient; and
  (iii) optionally one or more agents selected from the group consisting of surfactants, preservatives, flavoring agents, sweetening agents, and antifoaming agents;
  wherein median particle size of iniparib or a pharmaceutically acceptable salt, solvate, metabolite, or prodrug thereof is from about 20 μm to about 400 μm; and
wherein the formulation is stable at about 5±5° C. to about 25±5° C. for at least 12 months.

Embodiment 2: an oral dosage form comprising an immediate-release top layer and a controlled-release core, wherein said immediate-release layer comprises at least one of the stimulant, antihistamine, or antiemetic; and the controlled-release layer comprising a therapeutically effective amount of a formulation, comprising:
  (i) a pharmaceutically acceptable salt of iniparib or a solvate, metabolite, or prodrug thereof;
  (ii) a buffer;
  (iii) a surfactant;
  (iv) water; and
  (v) optionally one or more agents selected from the group consisting of preservatives, flavoring agents, sweetening agents, antifoaming agent, and suspensions aids;
  wherein said formulation is an oral liquid formulation, and
  wherein said formulation is stable at about 5±5° C. to about 25±5° C. for at least 6 months.

Embodiment 3: the dosage form of embodiment 1 or 2, wherein the stimulant is selected from the group consisting of aminophylline, caffeine, dyphlline, oxitriphylline, theophhylline, amphetamine, benzphetamine, dextroamphetamine, diethylpropion, mazindol, methamphetamine, methylphenidate, dexmethylphenidate, pemoline, sibutramine, modafinil, atomoxetine, phendimetrizine, phenteramine, adrafinil, phenylpropanolamine, psuedoephedrine, synephrine, amphetaminil, furfenorex, or a combination thereof.

Embodiment 4: the dosage form of embodiment 1 or 2, wherein the antiemetic is selected from the group consisting of aprepitant, dronabinol, perphenazine, palonosetron, trimethobenzamide, metoclopromide, domperidone, prochlorperazine, promethazine, chlorpromazine, trimethobenzamide, ondansetron, granisetron, hydroxyzine, acetylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxypemdyl, pipamazine, scopolamine, sulpiride, tetrahydrocannabinol, thiethylperazine, thioproperazine, tropisetron, droperidol, haloperidol, prochloperazine, metoclopramide, diphenhydramine, *cannabis*, midazolam, lorazepam, hyoscine, dexamethasone, emetrol, propofol and mixtures thereof.

Embodiment 5: the dosage form of embodiment 1 or 2, wherein the antihistamine is selected from the group consisting of 2-(m-fluorophenyl)-histamine, chlorpheniramine, mepyramine, terfenadine, astemizole, triprolidine, ethanolamines carbinoxamine, diphenhydramine, doxylamine, pyrilamine, tripelennamine, hydroxyzine, fexofenadine, brompheniramine chlorpheniramine, cyproheptadine, loratadine, cetirizine, dimaprit, impromidine, amthamine, cimetidine, ranitidine, nizatidine, famotidine, R-alpha-methylhistamine, imetit, immepip, thioperamide, iodophenpropit, clobenpropit, clobenpropit, imetit, clozapine, thioperamide, azelastine, brompheniramine, carbinoxamine, cetrizine, chlorpheniramine, clemastine, cyclizine, cyproheptadine, desloratidine, dimenhydrinate, diphenhydramine, emedastine, fexofenadine, ketotifen, levocabastine, loratadine, meclizine, olopatadine, phenindamine, promethazine, or a combination thereof.

Embodiment 6: the dosage form of any of embodiments 1-5, wherein said dosage form comprises an additional controlled-release layer comprising a therapeutically effective amount of an anticancer agent.

Embodiment 7: the dosage form of embodiment 6, wherein the anticancer agent is selected from the group consisting of carboplatin, gefitinib, gemcitabine, irinotecan, paclitaxel, picropodophyllin, topotecan, temozolomide, or a combination thereof.

Embodiment 8: a controlled-release iniparib formulation comprising a controlled-release matrix and from about 30 mg to about 400 mg of iniparib or a pharmaceutically acceptable salt, solvate, or prodrug thereof, wherein a median particle size of iniparib or a pharmaceutically acceptable salt, solvate, metabolite, or prodrug thereof is from about 20 μm to about 400 μm; and wherein said formulation provides a maximum mean blood concentration of iniparib of between about 200 ng/ml and about 6000 ng/ml upon oral administration to a subject in need thereof.

Embodiment 9: the controlled-release iniparib formulation of embodiment 8, wherein said formulation provides a maximum mean blood concentration of 4-iodo-3-aminobenzoic acid of between about 4 ng/ml and about 60 ng/ml upon oral administration to a subject in need thereof.

Embodiment 10: the controlled-release iniparib formulation of embodiment 8, wherein said formulation provides a maximum mean blood concentration of 4-iodo-3-aminobenzamide of between about 1 ng/ml and about 15 ng/ml upon oral administration to a subject in need thereof.

Embodiment 11: the controlled-release iniparib formulation of embodiment 8, wherein said formulation comprises at least about 30 mg of iniparib and wherein said formulation provides a maximum blood concentration of iniparib of at least about 400 ng/ml after oral administration to a subject in need thereof.

Embodiment 12: the controlled-release iniparib formulation of embodiment 8, wherein said formulation comprises at least about 30 mg of iniparib and wherein said formulation provides a maximum blood concentration of 4-iodo-3-aminobenzoic acid of at least about 8 ng/ml after oral administration to a subject in need thereof.

Embodiment 13: the controlled-release iniparib formulation of embodiment 8, wherein said formulation comprises at least about 30 mg of iniparib and wherein said formulation provides a maximum blood concentration of 4-iodo-3-aminobenzamide of at least about 2 ng/ml after oral administration to a subject in need thereof.

Embodiment 14: the controlled-release iniparib formulation of embodiment 8, wherein said formulation comprises at least about 30 mg of iniparib and wherein said formulation is repeatedly administered to a subject in need thereof about every 24 hours through steady state conditions.

Embodiment 15: the controlled-release iniparib formulation of embodiment 8, wherein said formulation comprises at least about 30 mg of iniparib and wherein said formulation is repeatedly administered to a subject in need thereof about twice a week through steady state conditions.

Embodiment 16: the controlled-release iniparib formulation of embodiment 8, wherein said formulation comprises at least about 100 mg of iniparib and wherein said formulation provides a maximum blood concentration of iniparib of at least about 400 ng/ml after oral administration to a subject in need thereof.

Embodiment 17: the controlled-release iniparib formulation of embodiment 8, wherein said formulation comprises at least about 100 mg of iniparib and wherein said formulation provides a maximum blood concentration of 4-iodo-3-aminobenzoic acid of at least about 8 ng/ml after oral administration to a subject in need thereof.

Embodiment 18: the controlled-release iniparib formulation of embodiment 8, wherein said formulation comprises at least about 100 mg of iniparib and wherein said formulation provides a maximum blood concentration of 4-iodo-3-aminobenzamide of at least about 2 ng/ml after oral administration to a subject in need thereof.

Embodiment 19: the controlled-release iniparib formulation of embodiment 8, wherein said formulation comprises at least about 100 mg of iniparib and wherein said formulation is repeatedly administered to a subject in need thereof about every 24 hours through steady state conditions.

Embodiment 20: the controlled-release iniparib formulation of embodiment 8, wherein said formulation comprises at least about 100 mg of iniparib and wherein said formulation is repeatedly administered to a subject in need thereof about twice a week through steady state conditions.

Embodiment 21: the controlled-release iniparib formulation of embodiment 8, wherein said formulation comprises at least about 30 mg of iniparib and wherein multiple doses of said formulation are administered to a subject in need thereof to provide a maximum mean blood concentration of iniparib of between about 200 ng/ml and about 6000 ng/ml upon oral administration to the subject in need thereof.

Embodiment 22: the controlled-release iniparib formulation of embodiment 8, wherein said formulation comprises at least about 100 mg of iniparib and wherein multiple doses of said formulation are administered to a subject in need thereof to provide a maximum mean blood concentration of iniparib of between about 200 ng/ml and about 6000 ng/ml upon oral administration to the subject in need thereof.

Embodiment 23: a liquid formulation comprising:
(i) a pharmaceutically acceptable salt of iniparib or a solvate, metabolite, or prodrug thereof;
(ii) a buffer;
(iii) a surfactant;
(iv) water; and
(v) optionally one or more agents selected from the group consisting of preservatives, flavoring agents, sweetening agents, antifoaming agent, and suspensions aids;
wherein said formulation is an oral liquid formulation, and
wherein said formulation is stable at about 5±5° C. to about 25±5° C. for at least 6 months.

Embodiment 24: the formulation of embodiment 23, wherein the metabolite of iniparib is selected from the group consisting of 4-iodo-3-nitrosobenzamide, 3-(hydroxyamino)-4-iodobenzamide, 3-hydroxy-4-iodobenzamide, 4-(methylthio)-3-nitrobenzamide, and N5-(3-((4-carbamoyl-2-nitrophenyl)thio)-1-((carboxymethyl)amino)-1-oxopropan-2-yl)glutamine Embodiment 25: the formulation of embodiment 23, wherein said pharmaceutically acceptable salt of iniparib is a salt selected from the group consisting of hydrochloride, hydrobromide, maleate, mesylate, tosylate, fumarate, tartrate, sulfate, and sulfonates Embodiment 26: the formulation of embodiment 25, wherein the molar ratio of iniparib moiety to anion is within the range from about 0.5:1 to about 1.5:1.

Embodiment 27: the formulation of embodiment 26, wherein said molar ratio of iniparib moiety to anion is about 1:1.

Embodiment 28: the formulation of any one of embodiments 23-27, wherein said salt form is substantially free of bound water and organic solvent.

Embodiment 29: the formulation of any one of embodiments 23-28, wherein said salt form is selected from the group consisting of iniparib hydrogentartrate, iniparib hydrochloride, iniparib hydrobromide, iniparib mesylate, iniparib tosylate, and iniparib sulfate.

Embodiment 30: the formulation of embodiment 29, wherein said salt form is iniparib hydrochloride.

Embodiment 31: the formulation of embodiment 29, wherein said salt form is iniparib hydrobromide.

Embodiment 32: the formulation of any one of embodiments 23-31, wherein said salt is amorphous salt form.

Embodiment 33: the formulation of any one of embodiments 23-31, wherein said salt is crystalline salt form.

Embodiment 34: the formulation of any one of embodiments 23-33, wherein the surfactant is poloxamer 188.

Embodiment 35: the formulation of embodiment 34, wherein the amount of poloxamer 188 is from about 1 mg/mL to about 15 mg/mL.

Embodiment 36: the formulation of any one of embodiments 23-33, wherein the surfactant is sodium lauryl sulfate.

Embodiment 37: the formulation of embodiment 36, wherein the amount of sodium lauryl sulfate is from about 0.1 mg/mL to about 2 mg/mL.

Embodiment 38: the formulation of any one of embodiments 23-37, wherein the oral liquid formulation comprises a preservative.

Embodiment 39: the formulation of embodiment 38, wherein the preservative is selected from the group consisting of sodium benzoate, a paraben or paraben salt, and combinations thereof.

Embodiment 40: the formulation of embodiment 38 or 39, wherein the amount of preservative is about 0.1 mg/mL to about 2 mg/mL.

Embodiment 41: the formulation of any one of embodiments 23-40, wherein the buffer comprises an acetate buffer.

Embodiment 42: the formulation of embodiment 41, wherein the acetate buffer concentration is about 3 mM to about 15 mM.

Embodiment 43: the formulation of any one of embodiments 23-40, wherein the buffer comprises a phosphate buffer.

Embodiment 44: the formulation of embodiment 43, wherein the phosphate buffer concentration is about 3 mM to about 15 mM.

Embodiment 45: the formulation of any one of embodiments 23-44, wherein the oral liquid formulation comprises an antifoaming agent.

Embodiment 46: the formulation of embodiment 45, wherein the antifoaming agent is simethicone.

Embodiment 47: the formulation of any one of embodiments 23-46, wherein the amount of the antifoaming agent is about 0.1 mg/mL to about 2 mg/mL.

Embodiment 48: the formulation of any one of embodiments 23-47, wherein the oral liquid formulation comprises a suspension aid.

Embodiment 49: the formulation of embodiment 48, wherein the suspension aid comprises silicon dioxide, hydroxypropyl methylcellulose, methylcellulose, microcrystalline cellulose, polyvinylpyrrolidone, or combinations thereof.

Embodiment 50: the formulation of embodiment 49, wherein the suspension aid is silicon dioxide.

Embodiment 51: the formulation of embodiment 49, wherein the amount of silicon dioxide is about 0.1 mg/mL to about 5 mg/mL.

Embodiment 52: the formulation of embodiment 49, wherein the suspension aid is hydroxypropyl methylcellulose.

Embodiment 53: the formulation of embodiment 52, wherein the amount of hydroxypropyl methylcellulose is about 3 mg/ml to about 10 mg/ml.

Embodiment 54: the formulation of embodiment 49, wherein the suspension aid is a combination of polyvinylpyrrolidone and hydroxypropyl methylcellulose.

Embodiment 55: the formulation of embodiment 53, wherein the amount of polyvinylpyrrolidone is about 0.5 mg/mL to about 3 mg/mL and the amount of hydroxypropyl methylcellulose is about 3 mg/mL to about 10 mg/mL.

Embodiment 56: the formulation of any one of embodiments 23-55, wherein the formulation comprises a flavoring agent.

Embodiment 57: the formulation of any one of embodiments 23-56, wherein the oral liquid formulation comprises a sweetener.

Embodiment 58: the formulation of embodiment 57, wherein the sweetener is sucralose or xylitol.

Embodiment 59: the formulation of any one of embodiments 23-58, wherein the oral liquid formulation is in the form of a suspension.

Embodiment 60: the formulation of any one of embodiments 23-59, wherein the pH of the oral liquid formulation is between about 4 and about 8.

Embodiment 61: the formulation of embodiment 60, wherein the pH is between about 6 and about 7.

Embodiment 62: the formulation of embodiment 60, wherein the pH is between about 7 and about 8.

Embodiment 63: the formulation of any of embodiments 23-62, wherein the amount of the pharmaceutically acceptable salt of iniparib corresponds to about 0.5 mg/mL to about 20 mg/mL of iniparib as a free base.

Embodiment 64: the formulation of any of embodiments 23-63, wherein the formulation is stable at about 25±5° C. for at least 6 months.

Embodiment 65: the formulation of any of embodiments 23-63, wherein the formulation is stable at about 5±5° C. for at least 6 months.

Embodiment 66: the formulation of any of embodiments 23-63, wherein the formulation is stable at about 25±5° C. for at least 12 months.

Embodiment 67: the formulation of any of embodiments 23-63, wherein the formulation is stable at about 5±5° C. for at least 12 months.

Embodiment 68: the formulation of any of embodiments 23-63, wherein the formulation is stable at about 25±5° C. for at least 24 months.

Embodiment 69: the formulation of any of embodiments 23-63, wherein the formulation is stable at about 5±5° C. for at least 24 months.

Embodiment 70: an aqueous composition comprising a pharmaceutically acceptable salt of iniparib or a solvate, metabolite, or prodrug thereof, a pharmaceutically acceptable delivery vehicle, and a mucoadhesive agent, wherein the aqueous composition is formulated for transmucosal administration.

Embodiment 71: the composition of embodiment 70, wherein the delivery vehicle comprises water, purified water, saline, liposome, mineral oil, alcohol, or a combination thereof.

Embodiment 72: the composition of embodiment 70 or 71, wherein the mucoadhesive agent comprises hydroxypropyl-methylcellulose, monomeric alpha cyanoacrylate, polyacrylic acid, poly methacrylate derivatives, chitosan, hyaluronic acid, xanthan gum, or a combination thereof.

Embodiment 73: the composition of any one of embodiments 70-72, wherein the composition further comprises an effective amount of a vasoconstrictor.

Embodiment 74: the composition of embodiment 73, wherein the vasoconstrictor comprises epinephrine, phenylephrine, methoxamine, norepinephrine, zolmitriptan, tetrahydrozaline, naphazoline, or a combination thereof.

Embodiment 75: the composition of any one of embodiments 70-74, wherein the composition further comprises an effective amount of a corticosteroid, an antihistamine, an anticholinergic, or a combination thereof.

Embodiment 76: the composition of any one of embodiments 70-75, wherein said composition is in a form selected from a spray, aerosol, mist, nebulae, ointment, cream, gel, paste, salve, solution, suspension, tincture, patch, and atomized vapor.

Embodiment 77: the composition of any one of embodiments 70-76, wherein the composition is formulated as a nasal spray or an inhalation solution.

Embodiment 78: a method of treating cancer in a subject in need thereof comprising administering to the subject in need thereof a therapeutically effective amount of:
- (a) iniparib, or a pharmaceutically acceptable salt, solvate, metabolite, or prodrug thereof formulated as:
  - (A1) an oral solid formulation comprising:
    - (i) iniparib or a pharmaceutically acceptable salt, solvate, metabolite, or prodrug thereof;
    - (ii) at least one pharmaceutically acceptable excipient; and
    - (iii) optionally one or more agents selected from the group consisting of surfactants, preservatives, flavoring agents, sweetening agents, and antifoaming agents;
    - wherein median particle size of iniparib or a pharmaceutically acceptable salt, solvate, metabolite, or prodrug thereof is from about 20 µm to about 400 µm; and wherein the formulation is stable at about 5±5° C. to about 25±5° C. for at least 12 months;
  - (A2) an oral dosage form comprising an immediate-release top layer and a controlled-release core, wherein said immediate-release layer comprises at least one of the stimulant, antihistamine, or antiemetic; and the controlled-release layer comprising a therapeutically effective amount of a formulation, comprising:
    - (i) iniparib or a pharmaceutically acceptable salt, solvate, metabolite, or prodrug thereof;
    - (ii) at least one pharm aceutically acceptable excipient; and
    - (iii) optionally one or more agents selected from the group consisting of surfactants, preservatives, flavoring agents, sweetening agents, and antifoaming agents;
    - wherein median particle size of iniparib or a pharmaceutically acceptable salt, solvate, metabolite, or prodrug thereof is from about 20 μm to about 400 μm; and wherein the formulation is stable at about 5±5° C. to about 25±5° C. for at least 12 months;
(A3) an oral dosage form comprising an immediate-release top layer and a controlled-release core, wherein said immediate-release layer comprises at least one of the stimulant, antihistamine, or antiemetic; and the controlled-release layer comprising a therapeutically effective amount of a formulation, comprising:
(i) a pharmaceutically acceptable salt of iniparib or a solvate, metabolite, or prodrug thereof;
(ii) a buffer;
(iii) a surfactant;
(iv) water; and
(v) optionally one or more agents selected from the group consisting of preservatives, flavoring agents, sweetening agents, antifoaming agent, and suspensions aids;
wherein said formulation is an oral liquid formulation, and
wherein said formulation is stable at about 5±5° C. to about 25±5° C. for at least 6 months;
(A4) a controlled-release iniparib formulation comprising a controlled-release matrix and from about 30 mg to about 400 mg of iniparib or a pharmaceutically acceptable salt, solvate, or prodrug thereof, wherein a median particle size of iniparib or a pharmaceutically acceptable salt, solvate, metabolite, or prodrug thereof is from about 20 μm to about 400 μm; and wherein said formulation provides a maximum mean blood concentration of iniparib of between about 200 ng/ml and about 6000 ng/ml upon oral administration to a subject in need thereof; or
(A5) an oral liquid formulation comprising
(i) a pharmaceutically acceptable salt of iniparib or a solvate, metabolite, or prodrug thereof;
(ii) a buffer;
(iii) a surfactant;
(iv) water; and
(v) optionally one or more agents selected from the group consisting of preservatives, flavoring agents, sweetening agents, antifoaming agent, and suspensions aids;
wherein said formulation is an oral liquid formulation, and
wherein said formulation is stable at about 5±5° C. to about 25±5° C. for at least 6 months;
(A6) an aqueous composition comprising a pharmaceutically acceptable salt of iniparib or a solvate, metabolite, or prodrug thereof, a pharmaceutically acceptable delivery vehicle, and a mucoadhesive agent, wherein the aqueous composition is formulated for transmucosal administration;
(b) about 0 mg/m$^2$ to about 90 mg/m$^2$ of temozolomide; and
(c) optionally radiation.

Embodiment 79: the method of embodiment 78, wherein cancer is selected from the group consisting of breast cancer, colon cancer, glioblastoma multiforme, lung cancer, melanoma, ovarian cancer, prostate cancer, and transformed stem cells cancer.

Embodiment 80: the method of embodiment 78 or 79, wherein about 6 mg/kg to about 9 mg/kg of iniparib or a salt, solvate, metabolite, or prodrug thereof is administered to the subject.

Embodiment 81: the method of embodiment 78 or 79, wherein about 7 mg/kg to about 8.6 mg/kg of iniparib or a salt, solvate, metabolite, or prodrug thereof is administered to the subject.

Embodiment 82: the method of embodiment 78 or 79, wherein about 8 mg/kg to about 8.6 mg/kg of iniparib or a salt, solvate, metabolite, or prodrug thereof is administered to the subject.

Embodiment 83: the method of embodiment 78 or 79, wherein about 8 mg/kg of iniparib or a salt, solvate, metabolite, or prodrug thereof is administered to the subject.

Embodiment 84: the method of any one of the embodiments 78-83, wherein the iniparib or a salt, solvate, metabolite, or prodrug thereof is administered to the subject once per day.

Embodiment 85: the method of any one of the embodiments 78-84, wherein the iniparib or a salt, solvate, metabolite, or prodrug thereof is administered to the subject for about twice a week.

Embodiment 86: the method of any one of the embodiments 78-85, wherein the iniparib or a salt, solvate, metabolite, or prodrug thereof is administered to the subject for about four, five or six weeks.

Embodiment 87: the method of any one of the embodiments 78-85, wherein the iniparib or a salt, solvate, metabolite, or prodrug thereof is administered to the subject for about six weeks.

Embodiment 88: the method of any one of the embodiments 78-87, wherein about 70 mg/m$^2$ to about 80 mg/m$^2$ of temozolomide is administered to the subject.

Embodiment 89: the method of any one of the embodiments 78-87, wherein about 75 mg/m$^2$ of temozolomide is administered to the subject.

Embodiment 90: the method of any one of the embodiments 78-87, wherein about 0 mg/m$^2$ to about 70 mg/m$^2$ of temozolomide is administered to the subject.

Embodiment 91: the method of any one of the embodiments 78-87, wherein about 5 mg/m$^2$ of temozolomide is administered to the subject.

Embodiment 92: the method of any one of the embodiments 78-87, wherein about 10 mg/m$^2$ of temozolomide is administered to the subject.

Embodiment 93: the method of any one of the embodiments 78-87, wherein about 15 mg/m$^2$ of temozolomide is administered to the subject.

Embodiment 94: the method of any one of the embodiments 78-87, wherein about 20 mg/m$^2$ of temozolomide is administered to the subject.

Embodiment 95: the method of any one of the embodiments 78-87, wherein temozolomide is not administered to the subject.

Embodiment 96: the method of any one of the embodiments 78-94, wherein temozolomide is administered to the subject daily.

Embodiment 97: the method of any one of the embodiments 78-94 or 96, wherein temozolomide is administered to the subject for about four, five or six weeks.

Embodiment 98: the method of any one of the embodiments 78-94 or 96, wherein temozolomide is administered to the subject for about six weeks.

Embodiment 99: the method of any one of the embodiments 78-98, wherein about 60 Gy of radiation is administered to the subject over the course of about four, five, or six weeks.

Embodiment 100: the method of any one of the embodiments 78-98, wherein about 60 Gy of radiation is administered to the subject over the course of about six weeks.

Embodiment 101: the method of any one of the embodiments 78-100, wherein upon completion of about six weeks of treatment with a combination of iniparib or a salt, solvate, metabolite, or prodrug thereof, temozolomide and radiation, the subject receives a treatment break of about four weeks.

Embodiment 102: the method of any one of the embodiments 78-101, further comprising a maintenance regimen.

Embodiment 103: the method of embodiment 102, wherein the maintenance regimen comprises about 8.6 mg/kg of iniparib or a salt, solvate, metabolite, or prodrug thereof, and about 150 mg/m$^2$ to about 200 mg/m$^2$ of temozolomide.

Embodiment 104: the method of embodiment 103, wherein the iniparib or a salt, solvate, metabolite, or prodrug thereof is administered to the subject once per day.

Embodiment 105: the method of embodiment 103 or 104, wherein the iniparib or a salt, solvate, metabolite, or prodrug thereof is administered to the subject for about twice a week.

Embodiment 106: the method of any one of the embodiments 103-105, wherein the iniparib or a salt, solvate, metabolite, or prodrug thereof is administered to the subject for about 1-6 cycles.

Embodiment 107: the method of any one of the embodiments 103-106, wherein the temozolomide is administered to the subject on days 1-5 of each cycle.

Embodiment 108: the method of any one of the embodiments 78-107, wherein the temozolomide is administered to the subject for about 1-6 cycles.

Embodiment 109: the method of any one of the embodiments 78-108, wherein the subject is an adult.

Embodiment 110: the method of any one of the embodiments 78-108, wherein the subject is elderly.

Embodiment 111: the method of any one of the embodiments 78-108, wherein the subject is a child.

Embodiment 112: the method of any one of embodiments 78-111, wherein iniparib, or a pharmaceutically acceptable salt, solvate, metabolite, or prodrug thereof is administered to the subject in a fasted state.

Embodiment 113: the method of any one of embodiments 78-111, wherein iniparib, or a pharmaceutically acceptable salt, solvate, metabolite, or prodrug thereof is administered to the subject in a fed state.

Embodiment 114: the method of embodiments 78 or 79, wherein iniparib, or a pharmaceutically acceptable salt, solvate, metabolite, or prodrug thereof is administered in combination with an additional agent selected from the group consisting of anticancer agents, stimulants, antiemetics, antihistamine, or a combination thereof.

Embodiment 115: the method of embodiment 114, wherein the anticancer agent is selected from the group consisting of gemcitabine, carboplatin, paclitaxel, irinotecan, topotecan, temozolomide, picropodophyllin, and gefitinib.

Embodiment 116: the method of embodiment 114, wherein the stimulant is selected from the group consisting of aminophylline, caffeine, dyphlline, oxitriphylline, theophhylline, amphetamine, benzphetamine, dextroamphetamine, diethylpropion, mazindol, methamphetamine, methylphenidate, dexmethylphenidate, pemoline, sibutramine, modafinil, atomoxetine, phendimetrizine, phenteramine, adrafinil, phenylpropanolamine, psuedoephedrine, synephrine, amphetaminil, furfenorex, or a combination thereof.

Embodiment 117: the method of embodiment 114, wherein the antiemetic is selected from the group consisting of aprepitant, dronabinol, perphenazine, palonosetron, trimethobenzamide, metoclopromide, domperidone, prochlorperazine, promethazine, chlorpromazine, trimethobenzamide, ondansetron, granisetron, hydroxyzine, acetylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxyperndyl, pipamazine, scopolamine, sulpiride, tetrahydrocannabinol, thiethylperazine, thioproperazine, tropisetron, droperidol, haloperidol, prochloperazine, metoclopramide, diphenhydramine, cannabis, midazolam, lorazepam, hyoscine, dexamethasone, emetrol, propofol and mixtures thereof.

Embodiment 118: the method of embodiment 114, wherein the antihistamine is selected from the group consisting of 2-(m-fluorophenyl)-histamine, chlorpheniramine, mepyramine, terfenadine, astemizole, triprolidine, ethanolamines carbinoxamine, diphenhydramine, doxylamine, pyrilamine, tripelennamine, hydroxyzine, fexofenadine, brompheniramine chlorpheniramine, cyproheptadine, loratadine, cetirizine, dimaprit, impromidine, amthamine, cimetidine, ranitidine, nizatidine, famotidine, R-alpha-methylhistamine, imetit, immepip, thioperamide, iodophenpropit, clobenpropit, clobenpropit, imetit, clozapine, thioperamide, azelastine, brompheniramine, carbinoxamine, cetrizine, chlorpheniramine, clemastine, cyclizine, cyproheptadine, desloratidine, dimenhydrinate, diphenhydramine, emedastine, fexofenadine, ketotifen, levocabastine, loratadine, meclizine, olopatadine, phenindamine, promethazine, or a combination thereof.

While preferred embodiments have been shown and described herein, it will be obvious to those skilled in the art that such embodiments are provided by way of example only. Numerous variations, changes, and substitutions will now occur to those skilled in the art without departing from this disclosure. It should be understood that various alternatives to the embodiments described herein might be employed in practicing current disclosure.

What is claimed is:

1. An oral dosage formulation, comprising:
   (i) iniparib or a pharmaceutically acceptable salt, solvate, metabolite, or prodrug thereof;
   (ii) at least one pharmaceutically acceptable excipient; and
   (iii) optionally one or more agents selected from the group consisting of surfactants, preservatives, flavoring agents, sweetening agents, and antifoaming agents;
   wherein a median particle size of iniparib or the pharmaceutically acceptable salt, solvate, metabolite, or prodrug thereof is from about 20 μm to about 400 μm; and
   wherein the formulation is stable at about 5±5° C. to about 25±5° C. for at least 12 months.

2. The formulation of claim 1, wherein the metabolite of iniparib is selected from the group consisting of: 4-iodo-3-nitrosobenzamide, 3-(hydroxyamino)-4-iodobenzamide, 3-hydroxy-4-iodobenzamide, 4-(methylthio)-3-nitrobenzamide, and N5-(3-((4-carbamoyl-2-nitrophenyl)thio)-1-((carboxymethyl)amino)-1-oxopropan-2-yl)glutamine.

3. The formulation of claim 1, wherein the pharmaceutically acceptable excipient is selected from the group consisting of fillers, binders, suspending agents, disintegrants, lubricants, and combinations thereof.

4. The formulation of claim 3, wherein the oral dosage formulation comprises a filler, optionally from about 20% to about 40% by weight.

5. The formulation of claim 3, wherein the oral dosage formulation comprises a binder, optionally from about 15% to about 25% by weight.

6. The formulation of claim 3, wherein the oral dosage formulation comprises a suspending agent, optionally from about 1% to about 4% by weight.

7. The formulation of claim 3, wherein the oral dosage formulation comprises a disintegrant, optionally from about 2% to about 6% by weight.

8. The formulation of claim 3, wherein the oral dosage formulation comprises a lubricant, optionally from about 1% to about 3% by weight.

9. The formulation of claim 1, wherein the oral dosage formulation comprises a surfactant.

10. The formulation of claim 9, wherein the surfactant is sodium lauryl sulfate, optionally from about 0.5% to about 2% by weight.

11. The formulation of claim 9, wherein the surfactant is poloxamer 188, optionally from about 7% to about 15% by weight.

12. The formulation of claim 9, wherein the surfactant is polysorbate 80, optionally from about 0.5% to about 2% by weight.

13. The formulation of claim 1, wherein said median particle size of iniparib or a pharmaceutically acceptable salt, solvate, metabolite, or prodrug thereof is about 400 µm, 300 µm or more, 200 µm or more, 100 µm or more, 50 µm or more, or 20 µm or more.

14. The formulation of claim 1, wherein iniparib or a pharmaceutically acceptable salt, solvate, metabolite, or prodrug thereof is present in an amount of at least about 10 mg.

15. The formulation of claim 1, wherein the amount of iniparib or a pharmaceutically acceptable salt, solvate, metabolite, or prodrug thereof is about 10 mg, about 20 mg, about 30 mg, about 33.3 mg, about 40 mg, about 50 mg, about 66.6 mg, about 75 mg, about 100 mg, about 150 mg, or about 200 mg.

16. The formulation of claim 1, wherein the oral dosage formulation comprises a preservative.

17. The formulation of claim 1, wherein the oral dosage formulation comprises an antifoaming agent or a flavoring agent.

18. The formulation of claim 1, wherein the formulation is:
    (a) stable at about 25±5° C. for at least 12 months;
    (b) stable at about 5±5° C. for at least 12 months;
    (c) stable at about 25±5° C. for at least 24 months; or
    (d) stable at about 5±5° C. for at least 24 months.

19. A controlled-release iniparib formulation comprising a controlled-release matrix and from about 30 mg to about 400 mg of iniparib or a pharmaceutically acceptable salt, solvate, or prodrug thereof, wherein a median particle size of iniparib or the pharmaceutically acceptable salt, solvate, metabolite, or prodrug thereof is from about 20 µm to about 400 µm; and
    wherein said formulation provides a maximum mean blood concentration of iniparib of between about 200 ng/ml and about 6000 ng/ml upon oral administration to a subject in need thereof.

20. A controlled-release formulation, comprising:
    (i) iniparib or a pharmaceutically acceptable salt, solvate, metabolite, or prodrug thereof, wherein a median particle size of iniparib or the pharmaceutically acceptable salt, solvate, metabolite, or prodrug thereof is from about 20 µm to about 400 µm;
    (ii) at least one pharmaceutically acceptable excipient; and
    (iii) optionally one or more agents selected from the group consisting of surfactants, preservatives, flavoring agents, sweetening agents, and antifoaming agents;
wherein the controlled release formulation comprises an additional controlled-release layer comprising an anticancer agent, wherein the anticancer agent is temozolomide.

* * * * *